(12) United States Patent
Kaneko

(10) Patent No.: US 8,989,353 B2
(45) Date of Patent: Mar. 24, 2015

(54) GRID FOR RADIATION IMAGING AND METHOD FOR PRODUCING THE SAME

(75) Inventor: Yasuhisa Kaneko, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 428 days.

(21) Appl. No.: 13/521,725

(22) PCT Filed: Mar. 18, 2011

(86) PCT No.: PCT/JP2011/057497
§ 371 (c)(1),
(2), (4) Date: Jul. 11, 2012

(87) PCT Pub. No.: WO2011/122506

PCT Pub. Date: Oct. 6, 2011

(65) Prior Publication Data

US 2012/0307976 A1   Dec. 6, 2012

(30) Foreign Application Priority Data

| Mar. 30, 2010 | (JP) | 2010-077903 |
| Mar. 30, 2010 | (JP) | 2010-077904 |
| May 18, 2010 | (JP) | 2010-114322 |
| May 18, 2010 | (JP) | 2010-114323 |
| Jun. 29, 2010 | (JP) | 2010-147802 |
| Jun. 29, 2010 | (JP) | 2010-147803 |
| Sep. 30, 2010 | (JP) | 2010-221542 |
| Jan. 27, 2011 | (JP) | 2011-015505 |

(51) Int. Cl.
*H01L 31/18* (2006.01)
*C25D 5/02* (2006.01)
(Continued)

(52) U.S. Cl.
CPC *G21K 1/06* (2013.01); *G21K 1/025* (2013.01); *C25D 3/00* (2013.01);
(Continued)

(58) Field of Classification Search
CPC ........ A61B 6/484; A61B 6/4291; G21K 1/06; G21K 2201/06; G21K 2201/067; G21K 2207/005

USPC ............ 378/62, 85, 87, 145, 157; 216/13, 18, 216/24; 252/582, 282; 156/60; 342/368; 385/3, 37

See application file for complete search history.

(56) References Cited

U.S. PATENT DOCUMENTS

| 7,453,981 B2 * | 11/2008 | Baumann et al. ................ 378/62 |
| 7,579,588 B2 * | 8/2009 | Naya et al. ...................... 250/288 |
| 2007/0183560 A1 * | 8/2007 | Popescu et al. ................... 378/5 |
| 2010/0278297 A1 | 11/2010 | Börner et al. |

FOREIGN PATENT DOCUMENTS

| JP | 2001-349992 A | 12/2001 |
| JP | 2006-259264 A | 9/2006 |
| JP | 4608679 B | 1/2011 |

OTHER PUBLICATIONS

Chinese Office Action dated Jul. 25, 2014 with an English translation thereof.

(Continued)

*Primary Examiner* — Jack Berman
*Assistant Examiner* — Kevin Chung
(74) *Attorney, Agent, or Firm* — McGinn IP Law Group, PLLC

(57) ABSTRACT

A conductive substrate (18) and an etching substrate (20) are bonded to each other. An etch mask (25) is formed on the etching substrate (20) using a photolithography technique. On the etching substrate (20), grooves (20a) and X-ray transmitting sections (14b) are formed by dry etching using Bosch process. The grooves (20a) are filled with Au (27) by an electroplating method using the conductive substrate (18) as an electrode. Thus, X-ray absorbing sections (14a) are formed.

20 Claims, 52 Drawing Sheets

(51) Int. Cl.
 *G21K 1/06* (2006.01)
 *G21K 1/02* (2006.01)
 *C25D 3/00* (2006.01)
 *A61B 6/00* (2006.01)

(52) U.S. Cl.
 CPC .......... *G21K 2207/005* (2013.01); *A61B 6/484* (2013.01); *G21K 2201/06* (2013.01); *G21K 2201/067* (2013.01); *A61B 6/4092* (2013.01); *A61B 6/4291* (2013.01)
 USPC ................ 378/154; 378/145; 378/87; 378/62

(56) References Cited

OTHER PUBLICATIONS

International Search Report in PCT/JP2011/057497 dated Jun. 14, 2011 (English Translation Thereof).

C. David et al., "Differential X-ray phase contrast imaging using a shearing interferometer", Applied Physics Letters, vol. 81, No. 17, Oct. 2002, pp. 3287.

Hector Canabal et al., "Improved phase-shifting method for automatic processing of moiré deflectograms", Applied Optics, vol. 37, No. 26, Sep. 1998, p. 6227.

* cited by examiner

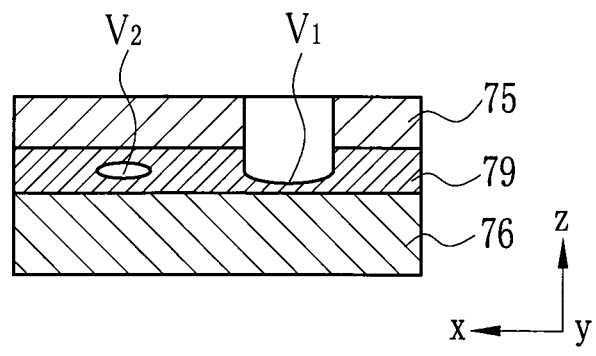
FIG. 20A
FIG. 20B
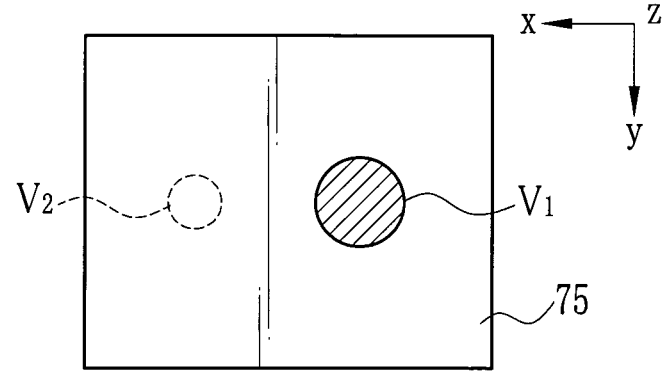
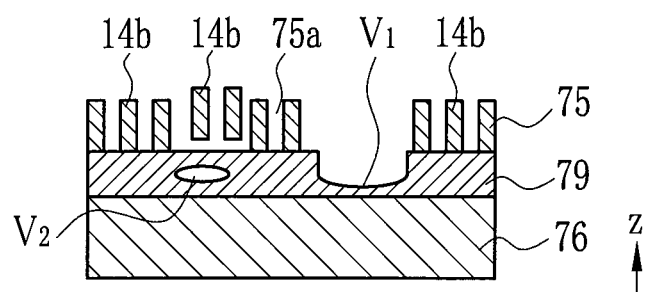
FIG. 21A
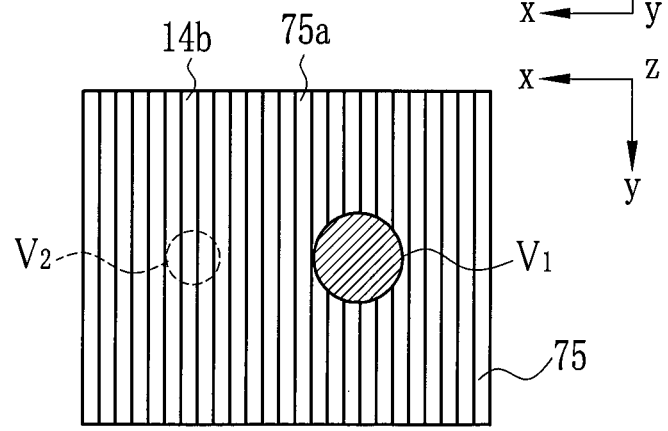
FIG. 21B

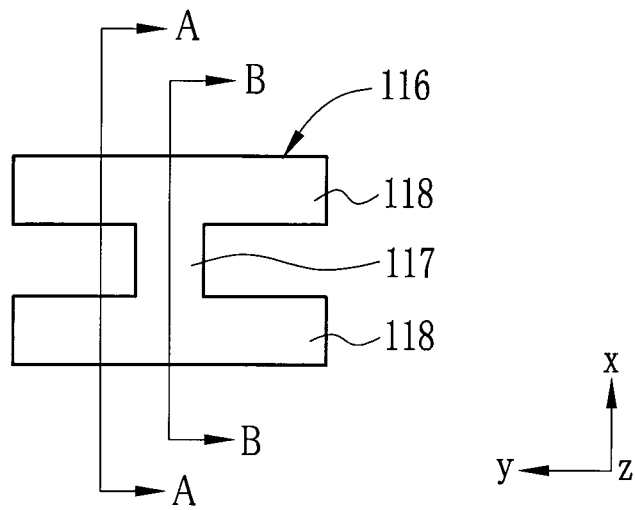
FIG. 36
CROSS-SECTION TAKEN ALONG LINE A-A
FIG. 37A
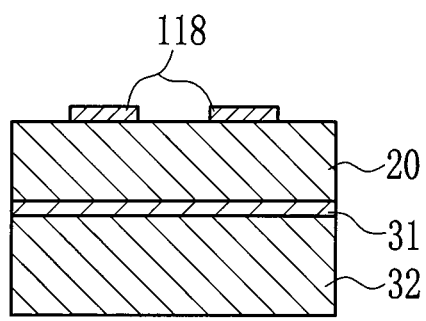
CROSS-SECTION TAKEN ALONG LINE B-B
FIG. 37B
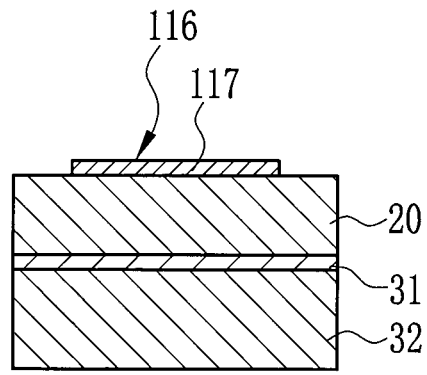
FIG. 37C
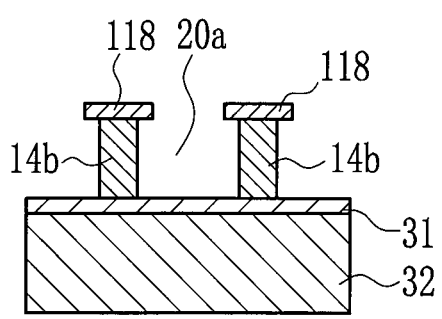
FIG. 37D
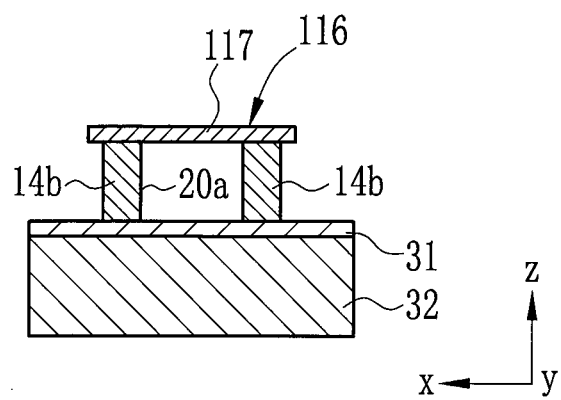

CROSS-SECTION TAKEN ALONG LINE A-A

CROSS-SECTION TAKEN ALONG LINE B-B

CROSS-SECTION TAKEN
ALONG LINE A-A

CROSS-SECTION TAKEN
ALONG LINE B-B

CROSS-SECTION TAKEN ALONG LINE A-A

CROSS-SECTION TAKEN ALONG LINE B-B

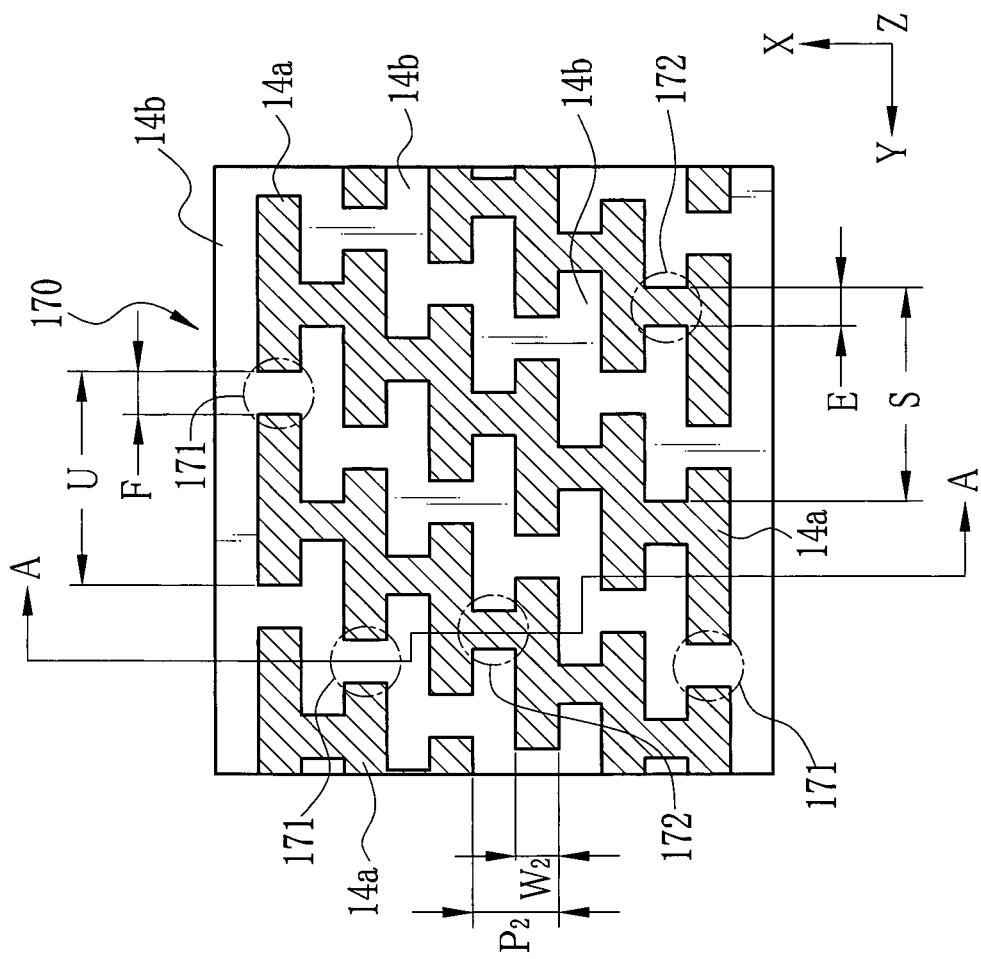
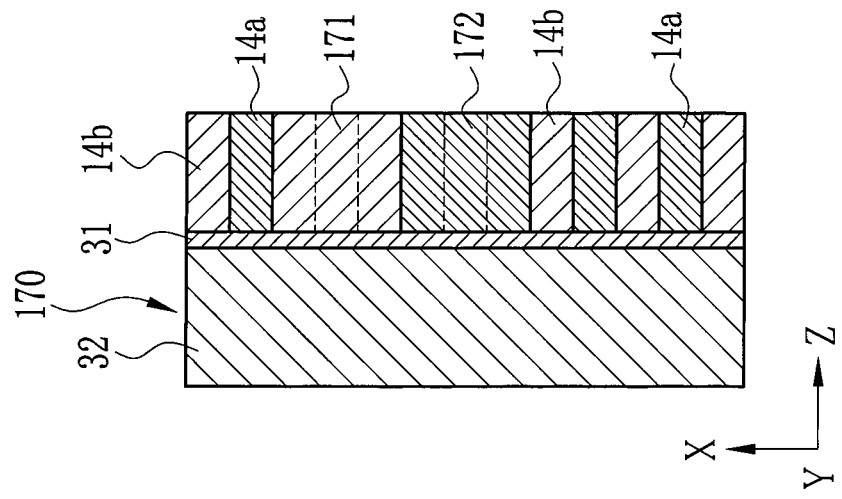

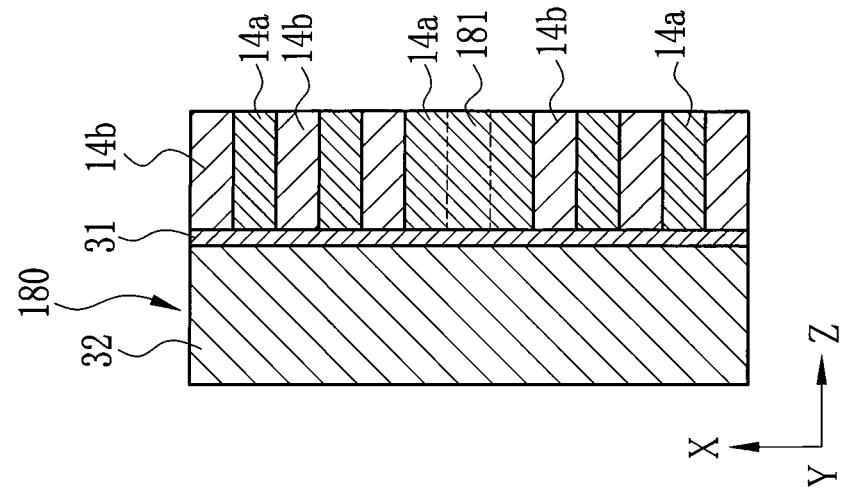
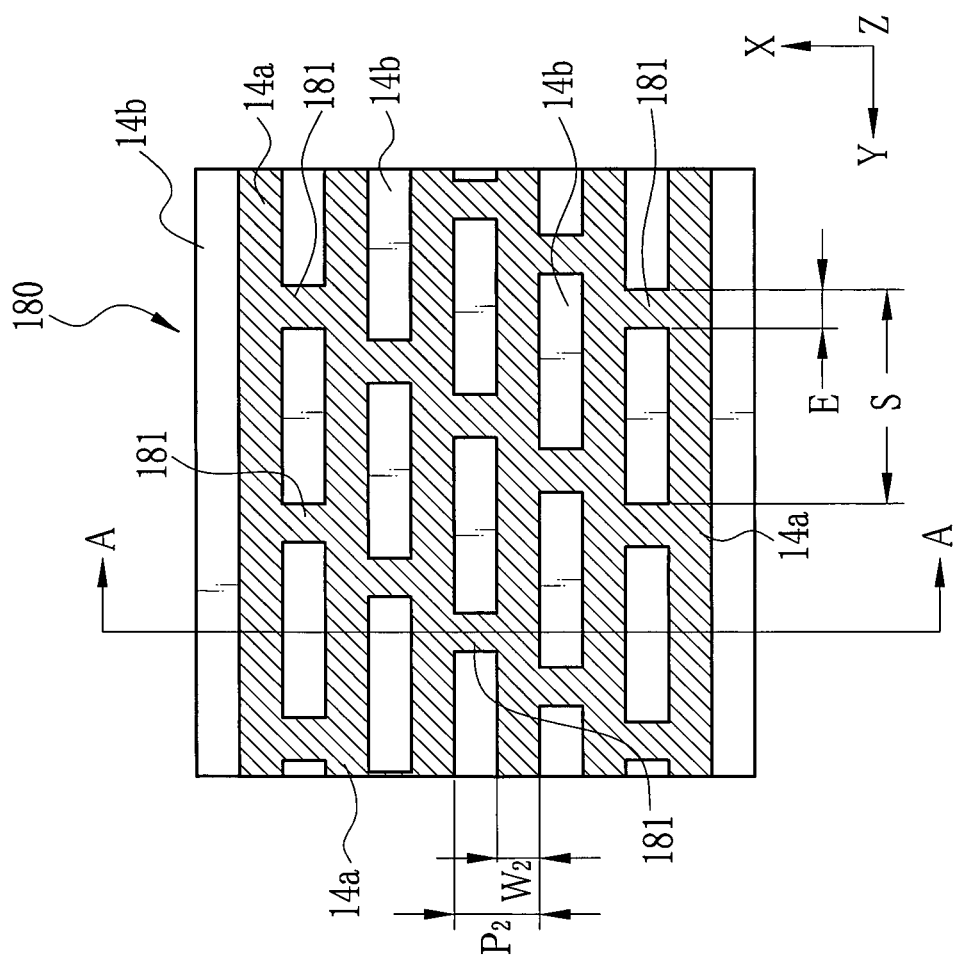

GRID FOR RADIATION IMAGING AND METHOD FOR PRODUCING THE SAME

TECHNICAL FIELD

The present invention relates to a grid for radiation imaging and a method for producing the same.

BACKGROUND ART

It is known that X-ray changes its intensity and phase by interaction between the X-ray and an object when the X-ray is incident on the object. The phase of the X-ray interacts with the object more strongly than the intensity of the X-ray does. Researches have been conducted actively on X-ray phase imaging that uses the above property of the X-ray to get a high contrast image (hereinafter referred to as phase contrast image) of an object with low X-ray absorption properties based on the phase change (angular change) of the X-ray caused by the object.

An X-ray imaging system using the Talbot effect caused by two transmission-type diffraction gratings (grids) is devised as one type of X-ray phase imaging (for example, Japanese Patent No. 4608679 and C. David et al., "Differential X-ray phase contrast imaging using a shearing interferometer", Applied Physics Letters, Vol. 81, No. 17, October 2002, page 3287). In this X-ray imaging system, a first grid is disposed behind an object when viewed from an X-ray source, and a second grid is disposed downstream of the first grid by the Talbot length. Behind the second grid, an X-ray image detector for detecting the X-ray to generate an image is disposed. Each of the first and second grids has a stripe pattern of X-ray absorbing sections and X-ray transmitting sections extending in one direction and the absorbing sections and the X-ray transmitting sections are alternately arranged in a direction orthogonal to the extending direction. The Talbot length is a distance at which the X-ray passed through the first grid forms a self image (fringe image) due to the Talbot effect. The fringe image formed by the Talbot effect is modulated by an interaction (phase change) between the object and the X-ray.

In the above X-ray imaging system, moiré fringes generated by the superposition (intensity modulation) of the self image of the first grid and the second grid are detected using a fringe scanning method. Phase information of the object is obtained from changes in moiré fringes caused by the object. In the fringe scanning method, images are captured while the second grid is translationally moved in a direction substantially parallel to the plane of the first grid and substantially vertical to a grid direction of the first grid at a scanning pitch that is one of equally-divided parts of a grid pitch, and then angular distribution (differential image of the phase shift) of the X-ray refracted by the object is obtained from a change in each pixel value obtained by the X-ray image detector. Based on the angular distribution, the phase contrast image of the object is obtained. The phase scanning method is used in an imaging apparatus using laser light (for example, see Hector Canabal et al., "Improved phase-shifting method for automatic processing of moiré deflectograms", Applied Optics, Vol. 37, No. 26, September 1998, page 6227.)

The first and second grids require high X-ray absorption properties. In particular, the second grid requires higher X-ray absorption properties than the first grid to surely provide intensity modulation to the fringe image. For this reason, the X-ray absorbing sections of the first and second grids are formed with gold (Au) with a large atomic weight. The X-ray absorbing section of the second grid requires a large thickness in an X-ray traveling direction relative to its width, that is, a so-called high aspect ratio. The aspect ratio is a value obtained by dividing the thickness of the X-ray absorbing section by the width of the X-ray absorbing section. The above-described second grid has a microstructure. For example, the pitch between the X-ray absorbing sections is several μm, and the thickness of the X-ray absorbing section is several tens to several hundreds of μm in the X-ray traveling direction.

In the Japanese Patent No. 4608679, methods for producing first and second grids are disclosed. In one of the producing methods, grooves are formed using photolithography on a photosensitive polymer layer provided on a metal seed layer on a substrate. Au is deposited in the grooves by electroplating using the metal seed layer as an electrode. In another producing method, on one of faces of a plate-like silicon layer with the thickness of 50 μm, a seed layer is made of titanium or silicon using vapor deposition. The Au is deposited in the grooves, formed by etching the plate-like silicon layer, by electroplating using the seed layer as the electrode.

U.S. Patent Application Publication No. 2010/0278297 discloses that, as a conventional technique, a grating with grating webs and grating gaps alternately and periodically arranged is provided with filler beams for connecting the adjacent grating webs to provide stability to a grid structure. The filler beams are provided randomly along an extending direction of the grating gaps. The grating webs correspond to the X-ray absorbing sections, and the grating gaps correspond to the X-ray transmitting sections. The U.S. Patent Application Publication No. 2010/0278297 discloses that randomly provided filler beams generate capillary force acting in the grating gaps to bend the grating webs, and that an interval between the filler beams needs to satisfy a predetermined geometric condition in the extending direction of the grating gaps to prevent the grating webs from bending.

In the method for producing the grid disclosed in the Japanese Patent No. 4608679, a photosensitive polymer layer is used to form the X-ray absorbing section. This method is susceptible to the influence of the photosensitive polymer in processing accuracy, so the grid cannot be produced with high accuracy. The grooves are formed through the synchrotron radiation exposure with high directivity and development. Because polymer is soft, grid patterns such as plate-like patterns standing upright on a substrate are likely to be deformed by sticking (a phenomenon in which adjacent patterns stick to each other) caused by swinging or vibration of a solution during the development or surface tension of water during drying. Thus, it is difficult to maintain the uniformity in width and height of the grid with high accuracy. Because the Au has higher rigidity than the polymer, the polymer is likely to be deformed depending on the growth of the Au plating. This significantly degrades the performance of the grid. In addition, there are few domestic facilities capable of performing synchrotron radiation exposure. The exposure takes a long time, resulting in a low throughput, and thus it is not suitable for manufacture. Instead of using the photosensitive polymer layer, a silicon layer may be formed on the substrate. However, it is technically difficult to form the silicon layer by coating similar to that for the photosensitive polymer layer because it is necessary to melt the silicon at a temperature of at least 1400° C.

In another producing method disclosed in Japanese Patent No. 4608679, groove sections are formed by etching the thin-plate silicon layer with the thickness of 50 μm. Normally, the lower limit of the thickness of the silicon substrate is of the order of 200 μm to allow ease of handling including transfer to the etching device. Even if a titanium layer or a silicon layer is formed using the vapor deposition, the thickness of the formed layer is of the order of 1 µm, so the layer does not reinforce the plate-like silicon layer. Accordingly, it is unrealistic to form the grooves on the 50 µm plate-like silicon layer by etching. The titanium or silicon layer with the thickness of the order of 1 µm may be in a state of floating inside the groove section of the plate-like silicon layer. It is easily expected that the titanium or silicon layer comes off in the subsequent steps, for example, in the electroplating step. Thus, it is difficult to perform the electroplating inside the grooves.

In the U.S. Patent Application Publication No. 2010/0278297, the filler beams are effective for reinforcing the structure of the grating webs because the filler beams connect the grating webs corresponding to the X-ray absorbing sections. The filler beams, however, are not effective in preventing the photosensitive polymer layers from sticking when grating webs are formed using a method disclosed in, for example, Japanese Patent No. 4608679.

An object of the present invention is to provide a grid having X-ray absorbing sections with a high aspect ratio and a method for producing the grid with high accuracy.

DISCLOSURE OF INVENTION

In order to achieve the above objects and other objects, the grid for the radiation imaging of the present invention includes a plurality of radiation absorbing sections, a plurality of radiation transmitting sections, and a plurality of transmitting-section bridging portions for coupling the radiation transmitting sections. The radiation absorbing sections and the radiation transmitting sections extend in an extending direction. The radiation absorbing sections and the radiation transmitting sections are alternately arranged in an arranging direction orthogonal to the extending direction.

It is preferable that each of the transmitting-section bridging portions couples the two or more radiation transmitting sections in the arranging direction.

The transmitting-section bridging portions may be arranged in a staggered arrangement. The transmitting-section bridging portions may be arranged in a slanting direction relative to the arranging direction. The transmitting-section bridging portions adjacent in the arranging direction may have a random interval in the extending direction.

An arrangement pitch of the transmitting-section bridging portions adjacent in the extending direction may be random. The arrangement pitch of the transmitting-section bridging portions adjacent in the extending direction may take a value distributed within a range relative to a central value. An arrangement pitch of the transmitting-section bridging portions adjacent in the extending direction may take a prime number. An arrangement pitch of the transmitting-section bridging portions in the extending direction may be five or more times as wide as a width of the radiation absorbing section in the arranging direction.

The transmitting-section bridging portion may be arranged between the radiation transmitting sections. In this case, the transmitting-section bridging portion may be provided integrally with the radiation transmitting section or separately from the radiation transmitting section. The transmitting-section bridging portion may be formed through the radiation absorbing section and the radiation transmitting section in the arranging direction. It is preferable that a width of the transmitting-section bridging portion in an X-ray transmission direction orthogonal to the extending direction and the arranging direction is smaller than a width of the radiation transmitting section.

The transmitting-section bridging portion may be provided to couple the radiation transmitting sections across the radiation absorbing section.

The transmitting-section bridging portion may be composed of a coupling portion and a reinforcing member. The coupling portion couples end portions of the radiation transmitting sections in a radiation transmitting direction orthogonal to the extending direction and the arranging direction and the reinforcing member reinforces the coupling portion.

Another grid for radiation imaging of the present invention may be provided with a plurality of absorbing-section bridging portions for coupling the radiation absorbing sections.

Further another grid for radiation imaging of the present invention may be composed of a radiation absorbing section and a radiation transmitting section made of a semiconductor of one conductivity type doped with an impurity.

On one of faces of a grid layer composed of the radiation absorbing section and the radiation transmitting section, a semiconductor substrate may be bonded. The semiconductor substrate has a conductivity type opposite to the conductivity type of the radiation transmitting section by doping of another impurity. The semiconductor substrate of the opposite conductivity type may be made of a conductive thin-layer made of the semiconductor of the opposite conductivity type and a support substrate. The semiconductor of the one conductivity type may be made of an n-type semiconductor.

Another grid for radiation imaging may include a semiconductor substrate of one conductivity type doped with an impurity and a radiation absorbing section provided on the semiconductor substrate. The semiconductor substrate may be made of a p-type semiconductor.

Further another grid for radiation imaging of the present invention may be composed of a grid layer having a radiation absorbing section and a radiation transmitting section, a support layer bonded to the grid layer, and a plurality of depression portions provided on at least one of bonding surfaces of the grid layer and the support layer.

It is preferable that the size of each of the depression portions is equal to or smaller than a pixel size of a radiation image detector for detecting radiation passed through the grid for radiation imaging. Each of the depression portions may be formed from a linear depression extending in the arranging direction.

Still another grid for radiation imaging may be provided with a radiation absorbing section for absorbing radiation, a radiation transmitting section for passing the radiation, and an anchor layer having a rough supporting surface for supporting the radiation absorbing section and the radiation transmitting section.

Another grid for radiation imaging has a grid layer having a radiation absorbing section and a radiation transmitting section, and a support layer for supporting the grid layer. The grid layer and the support layer are bonded to a curved surface provided on a radiation-transmissive holding member and bent. In the case where the support layer is made of an inorganic material, it is preferable that a total thickness of the grid layer and the support layer is less than 200 µm. The support layer may be made of an organic material.

The radiation absorbing sections and the radiation transmitting sections may be extended in the extending direction, and may be alternately arranged in the arranging direction orthogonal to the extending direction. One of the radiation absorbing sections and the radiation transmitting sections may be arranged in cross-like shape, and the other of the radiation absorbing sections and the radiation transmitting sections may be surrounded by the radiation absorbing sections or the radiation transmitting sections arranged in the cross-like shape.

The grid for radiation imaging is used as a first grid in a radiation imaging system composed of the first grid for passing radiation emitted from a radiation source to form a first periodic pattern, an intensity modulator for providing intensity modulation to the first periodic pattern at one of relative positions out of phase with the first periodic pattern, a radiation image detector for detecting a second periodic pattern generated at the relative position by the intensity modulator, and a processing section for imaging phase information based on at least one of the first and second periodic patterns detected by the radiation image detector.

The above radiation imaging system may be composed of a second grid and a scanning section. In the second grid a grid structure composed of a portion passing the first periodic pattern and a portion absorbing the first periodic pattern is arranged periodically. The scanning section moves one of first and second grids at a predetermined pitch in a periodic direction of the grid structures of the first and second grids. When each of the positions moved by the scanning section corresponds to the relative position, any of the above grids for radiation imaging may be used as the second grid.

When the above radiation imaging system has a third grid that shields the radiation emitted from the radiation source area-selectively to form a plurality of linear light sources, any of the above grids for radiation imaging may be used as the third grid.

A method for producing a grid for radiation imaging of the present invention is provided with a bonding step, an etching step, and a plating step. In the bonding step, a radiation-transmissive first substrate and an electrically conductive and radiation-transmissive second substrate are bonded. In the etching step, the first substrate is etched through an etch mask to form grooves and a plurality of radiation transmitting sections disposed between the grooves. In the plating step, the grooves are plated by filling of a radiation absorbing material to form a plurality of radiation absorbing sections by an electroplating method using the second substrate as an electrode. It is preferable that deep dry etching is used for the etching.

It is preferable that the second substrate has substantially the same thermal expansion coefficient as the first substrate. The second substrate may be composed of a conductive thin-layer used as the electrode and a support substrate provided with the conductive thin-layer.

The second substrate may be made of a semiconductor, a same material as the first substrate. The second substrate may be composed of the semiconductor used as the electrode and a support substrate made of an insulator. Further, the first substrate may be made of a semiconductor of one conductivity type doped with an impurity, and the second substrate may be made of a semiconductor of a conductivity type opposite to the one conductivity type, doped with another impurity. The semiconductor of one conductivity type may of an n-type semiconductor.

It is preferable that at least a surface of the first substrate has an insulation property after the etching step. It is preferable that the first substrate has the specific resistance equal to or larger than 100 Ω·cm. An insulating layer may be formed on a part or an entire of the surface of the first substrate after the etching step. It is preferable that the insulating layer is hydrophilic. The specific resistance may be increased by ion implantation to the first substrate after the etching step.

The first substrate may be removed by a predetermined thickness from at least one of faces of the first substrate after the plating step. The second substrate may be removed, when the first substrate is removed by the predetermined thickness from the face to which the second substrate is bonded. The first substrate may be removed by the predetermined thickness from the face to which the second substrate is bonded after the first substrate is removed by the predetermined thickness from and a protective layer may be formed on the face not bonded to the second substrate.

Etching may be performed to the first substrate after the plating step to remove the radiation transmitting sections between the radiation absorbing sections.

A plurality of depression portions may be formed on at least one of bonding surfaces of the first and second substrates before the bonding step. The bonding surface of the first substrate may be made into a rough surface before the bonding step. A radiation-transmissive and electrically conductive anchor layer may be formed on the rough surface. The anchor layer may be polished to improve smoothness of the anchor layer.

When the radiation absorbing sections and the radiation transmitting sections extend in the extending direction and are alternately arranged in an arranging direction orthogonal to the extending direction, a transmitting-section bridging portion for coupling the radiation transmitting sections in the arranging direction may be formed before the plating method. In this case, the etch mask with a plurality of line patterns extending in the extending direction and arranged in the arranging direction and a plurality of bridge patterns for coupling the line patterns in the arranging direction may be provided. The transmitting-section bridging portion may be formed in the groove by etching the first substrate through the etch mask.

The bridge pattern may be made thinner than the mask pattern, and the transmitting-section bridging portion may be formed on a bottom portion of the groove using a difference in etching rates between the mask pattern and the bridge pattern.

The etch mask may be provided on the first substrate and have a plurality of line patterns extending in the extending direction and arranged in the arranging direction and the transmitting-section bridging portion may be composed of bridge patterns provided on the etch mask so as to couple the line patterns in the arranging direction.

The method may include a step of forming a plurality of bridge masks constituting the transmitting-section bridging portions in the arranging direction on the first substrate, a step for etching the first substrate through the bridge mask to a predetermined depth, a step for forming the etch mask provided with a plurality of line patterns extending in the extending direction and arranged in the arranging direction and a plurality of bridge patterns for coupling the line patterns and covering the bridge masks on the first substrate after the etching, and a step for etching the first substrate through the etch mask to form the transmitting-section bridging portions. Each of the transmitting-section bridging portions is composed of the bridge mask, the bridge pattern, and a coupling portion for coupling the radiation transmitting sections under the bridge mask.

The method may further include a step for forming a plurality of transmitting-section bridging portions extending in the arranging direction and arranged in the extending direction on the first substrate, a step for embedding the transmitting-section bridging portions inside the first substrate by forming a layer on a surface of the first substrate on which the transmitting-section bridging portions are formed, or by bonding substrates to increase thickness of the first substrate, and a step for etching the first substrate through the etch mask to form the grooves and the radiation transmitting sections. The transmitting-section bridging portions are formed through the grooves.

It is preferable that a width of the transmitting-section bridging portion in the extending direction has a dimension with which the first substrate under the transmitting-section bridging portion is removable by side etching during the etching of the first substrate.

The method may further include a step of forming an absorbing-section bridging portion for coupling the radiation absorbing sections in the arranging direction.

The method may include a step of emitting a first examination light passing through the support substrate and the conductive thin-layer and examining an etching state of the first substrate based on the first examination light passed through the grooves, and a step of emitting second examination light passing the support substrate, the conductive thin-layer, and the first substrate after the plating step and examining a filling state of the radiation absorbing material based on the second examination light passed through the first substrate.

It is preferable that mathematical expressions (1) and (2) are satisfied where $\lambda e$ denotes an absorption wavelength of the first substrate, and $\lambda d$ denotes an absorption wavelength of the conductive thin-layer, and $\lambda s$ denotes an absorption wavelength of the support substrate, and $\lambda m1$ denotes a wavelength of the first examination light, and $\lambda m2$ denotes a wavelength of the second examination light.

$$\lambda d, \lambda s < \lambda m1 < \lambda e \quad (1)$$

$$\lambda d, \lambda s, \lambda e < \lambda m2 \quad (2)$$

It is preferable that the first examination light is visible light with the wavelength $\lambda m1$ from 0.4 μm to 0.7 μm, and the second examination light is infrared light with the wavelength $\lambda m2$ of equal to or longer than 0.7 μm. It is preferable that the conductive thin-layer is a transparent conductive layer of ITO, IZO, or ZnO, or a metal thin-layer of Au, Pb, Pt, Ni, Cr, or Ti with a thickness equal to or smaller than 500 Å, or the transparent conductive thin-layer provided with the metal thin-layer on at least one of surfaces. The support substrate is made of glass.

The method may include a step of bending the grid by bonding the grid to a curved surface provided in a radiation-transmissive holding member. When the second substrate is made of an inorganic material, it is preferable that a total thickness of the first substrate and the second substrate is less than 200 μm. The second substrate may be composed of an organic material and a conductive thin-layer provided on the organic material.

When the second substrate is composed of a conductive thin-layer and a support substrate provided with the conductive thin-layer, the support substrate may be composed of a reinforcing substrate having rigidity against bending during the etching step and the plating step and an organic material layer formed on the reinforcing substrate. It is preferable to remove or thin the reinforcing substrate after the plating step.

According to the method for producing the grid for radiation imaging of the present invention, the second substrate functioning as the seed layer is provided to embed the radiation absorbing material in the grooves using electroplating. Thus, the radiation absorbing material is embedded in the grooves appropriately. Thereby, the present invention is excellently applied to mass-production and makes it easy to form the radiation absorbing sections. The second substrate functions as an etching stop layer when the first substrate is etched. Thereby, the in-plane uniformity in the depths of the grooves improves. Thus, the grid with excellent in-plane uniformity in radiation transmittance is produced.

In the etching step, the deep dry etching is used. Thereby, grooves with the high aspect ratio are formed. Because the thermal expansion coefficient of the second substrate is substantially the same as that of the first substrate, thermal stress during the bonding and deformation of the grid due to the heat during the use are prevented. Because the second substrate is composed of the conductive thin-layer and the support substrate, a highly radiation-transmissive material can be selected for the support substrate. Thus, the grid performance improves.

Because the first and second substrates are made of the semiconductor of the same material, the bondability between the first and second substrates improves while maintaining the function as the seed layer. Thus, the formation of voids between the first and second substrates is prevented. Because the first and second substrates are made of semiconductors of different conductivity types, the first and second substrates are connected in reverse bias. Thus, the grooves are appropriately filled with the radiation absorbing material using electroplating.

Because insulation is provided to at least on the surface of the first substrate, grooves are appropriately filled with the radiation absorbing material using electroplating. Because an insulating layer is provided with hydrophilic property when the insulating layer is formed to provide insulation to the second substrate, the plating liquid flows well during the electroplating.

By removing the first substrate or the second substrate after the completion of the grid, the radiation transmission properties of the grid is improved. The filling defects of the radiation absorbing material, which likely to occur on the opening side and the bottom side of the groove, are removed. Thus, the grid performance improves.

Depression portions are provided on the bonding surfaces of the first and second substrates to disperse and include the voids generated on the bonding surfaces. Thereby, the radiation absorbing sections and the radiation transmitting sections are prevented from coming off or distortion due to the voids. An anchor layer for supporting the radiation absorbing sections and the radiation transmitting sections prevent the radiation absorbing sections and the radiation transmitting sections form coming off.

A transmitting-section bridging portion for coupling the radiation transmitting sections are provided. Thereby, sticking is prevented. The sticking is a phenomenon in which the radiation transmitting section falls down.

The etching step is examined using the first examination light that passes through the support substrate and the conductive thin-layer. Thereby, the second substrate of a microstructure with the high aspect ratio is appropriately examined without the interference of scattered light line the microscope observation method. The electroplating step is examined using the second examination light that passes through the support substrate, the conductive thin-layer, and the second substrate, the examination is performed at low cost unlike the X-ray transmission observation because expensive facilities such as radiation source with micro focal size are not required. A wide observation field for examination improves the throughput.

The grid may be bent, so it is easy to form the grid of a converging structure.

According to the grid for the radiation imaging of the present invention, bridging portions are provided to couple the radiation transmitting sections. Thereby, the strength of the grid is increased.

The semiconductor is used for the radiation transmitting sections and the substrate to be bonded to the grid layer. Thereby, diffusion of the radiation absorbing material such as Au or the like is prevented. Thus, the reduction of the grid performance due to the diffusion of the radiation absorbing material is prevented.

The depression portions are provided between the grid layer and the support layer that supports the grid layer. A contact area between the grid layer and the support layer reduces. Thereby, loads applied to the bonding surfaces during the bonding increase. Thus, high bonding strength is obtained. The anchor layer for supporting the radiation absorbing sections and the radiation transmitting sections prevents the radiation absorbing sections and radiation transmitting sections from coming off.

The grid is bonded to a holding member with a curved surface, which makes it easy to form the grid of a converging structure. The present invention is not limited to the grid of a stripe pattern with the linear radiation absorbing sections and radiation transmitting sections alternately arranged. The present invention is applicable to a grid in which the radiation absorbing sections or the radiation transmitting sections are arranged in cross-like shapes. Thus, an optimum grid structure is obtained in accordance with the use of the grid.

In addition, the grid of the present invention can be used as one of the first to third grids used in the radiation imaging system. Thus, the radiation imaging system is capable of taking phase contrast images with high image quality.

BRIEF DESCRIPTION OF DRAWINGS

FIG. 20A is a cross-sectional view showing that the etching substrate has been come off from the void in the $10^{th}$ embodiment;

FIG. 20B is a plan view showing that the etching substrate has been come off from the void in the $10^{th}$ embodiment;

FIG. 21A is cross-sectional view showing that the X-ray transmitting section has been come off from the void in the $10^{th}$ embodiment;

FIG. 21B is a plan view showing that the X-ray transmitting section has been come off from the void, in the $10^{th}$ embodiment;

FIG. 36 is a plan view showing an etch mask used for producing the transmitting-section bridge members of the 14th embodiment;

FIGS. 37A to 37D are cross-sectional views showing steps for producing the transmitting-section bridge members of the 14th embodiment;

FIG. 57A is a plan view of a second grid having transmitting-section bridge members and absorbing-section bridge members in a $19^{th}$ embodiment;

FIG. 57B is a cross-sectional view of a second grid of the $19^{th}$ embodiment;

FIG. 63A is a plan view of a second grid provided only with absorbing-section bridge members in a $20^{th}$ embodiment;

FIG. 63B is a cross-sectional view taken along a line A-A in FIG. 63A;

BEST MODE FOR CARRYING OUT THE INVENTION

First Embodiment

Figure 1:
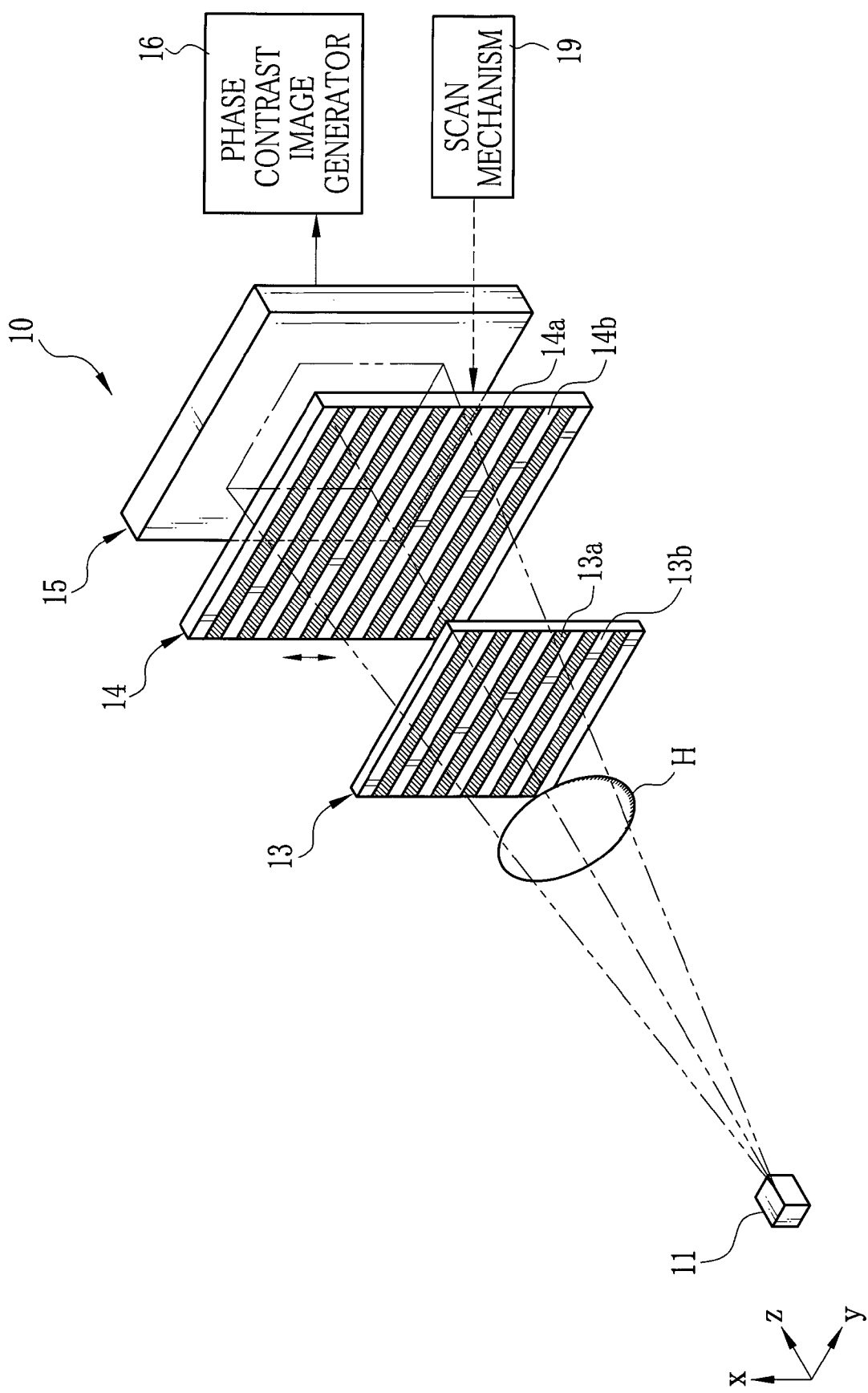
FIG. 1 is a schematic diagram showing an imaging system of a first embodiment.

FIG. 1 is a conceptual view showing an X-ray imaging system 10 of a first embodiment. The X-ray imaging system 10 is provided with an X-ray source 11, a first grid 13, a second grid 14, and an X-ray image detector 15. The X-ray source 11 has, for example, a rotating-anode type X-ray tube and a collimator for restricting an X-ray emission field. The X-ray source 11 emits X-ray to an object H. The first grid 13 and the second grid 14 are absorption grids. The first and second grids 13 and 14 are arranged to oppose the X-ray source 11 in a z direction that is a direction of X-ray emission.

The X-ray source 11 and the first grid 13 are spaced apart enough to place the object H. A distance between the first and second grids 13 and 14 is equal to or less than a minimum Talbot length. The X-ray imaging system 10 of this embodiment does not use the Talbot effect. Instead, the X-ray imaging system 10 projects the X-ray to take a phase contrast image.

The X-ray image detector 15 is, for example, a flat panel detector (FPD) using a semiconductor circuit. The X-ray image detector 15 is disposed behind the second grid 14. The X-ray image detector 15 is connected to a phase contrast image generator 16 for generating the phase contrast image from image data detected by the X-ray image detector 15.

The first grid 13 is provided with a plurality of X-ray absorbing sections 13a and a plurality of X-ray transmitting sections 13b both extending in a y direction that is a direction in a plane orthogonal to the z direction. The X-ray absorbing sections 13a and the X-ray transmitting sections 13b are alternately arranged in an x direction orthogonal to the z direction and the y direction to form a grid with a stripe pattern. The second grid 14, as with the first grid 13, is provided with a plurality of X-ray absorbing sections 14a and a plurality of X-ray transmitting sections 14b extending in the y direction. The X-ray absorbing sections 14a and the X-ray transmitting sections 14b are arranged alternately in the x direction.

The second grid 14 and a scan mechanism 19 constitute an intensity modulator of the present invention. The scan mechanism 19 translationally moves the second grid 14 in a grid pitch direction (the x direction) at an integral submultiple of a scan pitch (for example, one fifth of the scan pitch) of the second grid 14 at the time a phase contrast image is taken.

A configuration of the grid is described using the second grid 14 as an example. The first grid 13 has the same or similar configuration to the second grid 14 except the width and the pitch of the X-ray absorbing sections 13a in the x direction and the thickness of the X-ray absorbing sections 13a in the z direction, so the detailed description of the first grid 13 is omitted.

Figure 2B:
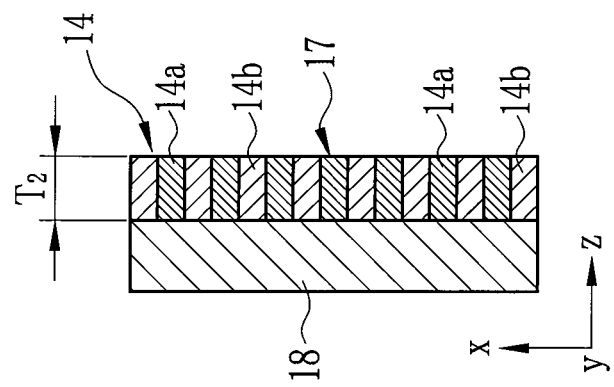
FIG. 2B is a cross-sectional view showing a second grid of the first embodiment.
Figure 2A:
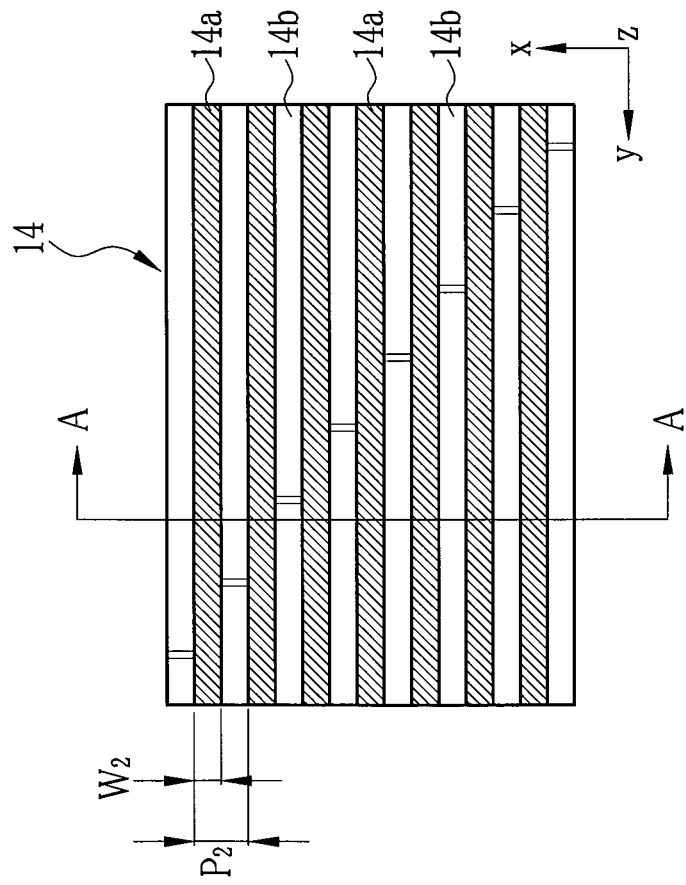
FIG. 2A is a plan view showing a second grid of the first embodiment.

FIG. 2A is a plan view showing the second grid 14 viewed from the X-ray image detector 15 side. FIG. 2B shows a cross-section taken along a line A-A in FIG. 2A. The second grid 14 is composed of a grid layer 17 and a conductive substrate (second substrate) 18 for supporting the grid layer 17. The grid layer 17 is composed of a plurality of X-ray absorbing sections 14a and a plurality of X-ray transmitting sections 14b. The X-ray absorbing sections 14a are made of metal having X-ray absorption properties, for example, gold, platinum, or the like. The X-ray transmitting sections 14b are made of an X-ray transmissive material such as silicon. The conductive substrate 18 is made of a metal substrate having conductivity necessary for producing the second grid 14, X-ray transmission properties not impairing grid performance of the grid layer 17, and rigidity to support the grid layer 17.

A width W2 and an arrangement pitch P2 of the X-ray absorbing sections 14a in the x direction are determined in accordance with a distance between the X-ray source 11 and the first grid 13, a distance between the first grid 13 and the second grid 14, a pitch of the X-ray absorbing sections 13a in the first grid 13, or the like. For example, the width W2 is approximately from 2 µm to 20 µm. The pitch P2 is approximately from 4 µm to 40 µm, that is, twice as much as the width W2. The thickness T2 of the X-ray absorbing section 14a in the z direction is, for example, approximately from 100 µm to 200 µm in consideration of vignetting of cone-beam X-ray emitted from the X-ray source 11. In this embodiment, the second grid 14 has, for example, the width W2 of 2.5 µm, the pitch P2 of 5 µm, and the thickness T2 of 100 µm.

Next, an operation of the X-ray imaging system 10 is described. A phase of the X-ray emitted from the X-ray source 11 is changed as the X-ray passes through the object H. The X-ray passed through the first grid 13 forms a fringe image that carries transmission phase information of the object H determined by a refractive index of the object H and a transmission optical path length.

Intensity of the fringe image is changed or modulated by the second grid 14 and detected using, for example, a fringe scanning method. In the fringe scanning method, the X-ray source 11 emits the X-ray to the object and images are captured for two or more times using the X-ray image detector 15 while the second grid 14 is translationally moved in an x direction along the grid surface about an X-ray focal point relative to the first grid 13 at a scanning pitch, which is one of equally-divided parts (for example, five equally-divided parts) of a grid pitch. Then, a phase differential image (corresponding to angular distribution of the X-ray refracted by the object) is obtained from a phase shift value (a difference in phases at the presence and absence of the object H) of the pixel data obtained from each pixel in the X-ray image detector 15. The phase differential image is integrated in the fringe-scanning direction. Thereby, a phase contrast image of the object is obtained.

Figure 3A:
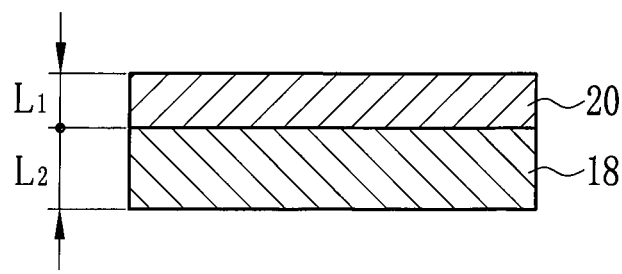
FIGS. 3A to 3F are explanatory views showing steps for producing the second grid of the first embodiment.

Next, a method for producing the second grid 14 is described. The first grid 13 is produced in the same manner as the second grid 14, so detailed description of the first grid 13 is omitted. FIGS. 3A to 3F show steps for producing the second grid 14. FIGS. 3A to 3F are cross-sections taken along an xz plane defined by the x-direction and z direction shown in FIGS. 1 and 2. As shown in FIG. 3A, in a first step, an etching substrate (first substrate) 20 and a conductive substrate 18 are joined or bonded to each other. The etching substrate 20 constitutes the X-ray transmitting sections 14b of the grid layer 17.

A material of the etching substrate 20 needs to have low X-ray absorption properties, high strength, and easy processability. For example, silicon (Si) is preferable. GaAs, Ge or quartz may be used. The thickness L1 of the etching substrate 20 is, for example, from 20 µm to 150 µm, and corresponds to the thickness T2 of the above-described X-ray absorbing section 14a in the z direction.

The conductive substrate 18 is preferably made of metal material having conductivity and low X-ray absorption properties, for example, Mg, Al, Ti, V, Cr, Mn, Fe, Co, Ni, Cu, Zn, their alloys, SUS, or the like. It is more preferable to use the conductive substrate 18 with a small difference in thermal expansion coefficient from the etching substrate 20, for example, kovar, inver, or the like. Thereby, thermal stress caused by heat during the bonding of the etching substrate 20 and the conductive substrate 18 and distortion of the second grid 14 caused by a temperature rise during the X-ray emission are prevented.

The thickness L2 of the conductive substrate 18 is larger than the thickness of the etching substrate 20 to ensure the strength of the second grid 14. The thickness L2 of the conductive substrate 18 is, for example, of the order of 100 µm to 700 µm. The total thickness of the etching substrate 20 and the conductive substrate 18 is made equal to or larger than 200 µm, for the sake of easy handling. The conductive substrate 18 may have the thickness larger than required, and be polished to the required thickness after the bonding.

To bond the etching substrate 20 and the conductive substrate 18, diffusion bonding with the application of heat and pressure, and normal-temperature bonding performed in a high vacuum to activate surfaces, or the like may be used. The etching substrate 20 and the conductive substrate 18 may be bonded using a material melted by heat such as In and AuSn.

Figure 3B:
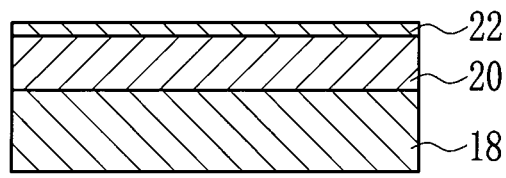

In a next step, an etch mask is formed on a top face of the etching substrate 20 using a general photolithography technique. As shown in FIG. 3B, a resist layer 22 is formed on the top face of the etching substrate 20. For example, the resist layer 22 is formed through a step for applying a liquid resist to the etching substrate 20 using an application method such as spin coating, and a step for prebaking or the like to evaporate or an organic solvent from the applied liquid resist.

Figure 3C:
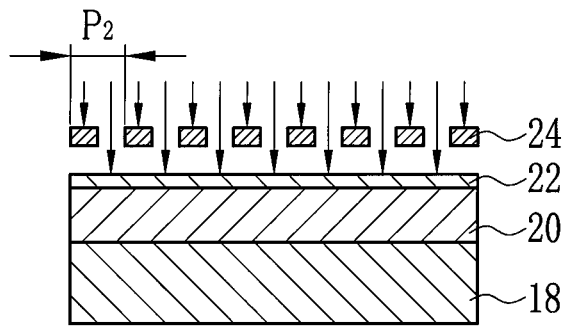
Figure 3D:
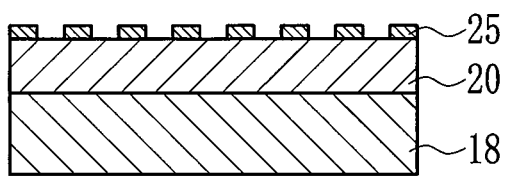

As shown in FIG. 3C, light such as UV rays is emitted to the resist layer 22 through an exposure mask 24 with a stripe pattern at the pitch P2 of several μm. Then, as shown in FIG. 3D, portions of the resist layer 22 exposed to the light are removed using a developing solution. Thereby, an etch mask 25 with the stripe pattern composed of line patterns extending in the y direction and arranged in the x direction is formed on the etching substrate 20. A width of each line pattern of the etch mask 25 is, for example, 2.5 μm. A width of each opening of the etch mask 25 is, for example, 2.5 μm. A known aligner or a known stepper is used for the photolithography. The above resist layer 22 is a positive resist. Alternatively, a negative resist that remains on the surface wherever it is exposed may be used. $SiO_2$, metal, or the like may be applied to the etching substrate 20 and then etched to form the etch mask instead of using the etch mask made of the resist layer.

Figure 3E:
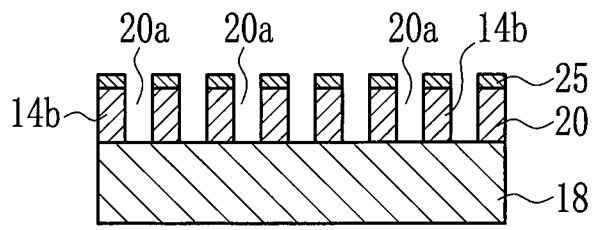

As shown in FIG. 3E, in a next step, a plurality of grooves 20a and a plurality of the X-ray transmitting sections 14b are formed on the etching substrate 20 using dry etching through the etch mask 25. The grooves 20a extend in the y direction and are arranged in the x direction. Each of the X-ray transmitting sections 14b is provided between the grooves 20a. Deep dry etching capable of forming grooves with a high aspect ratio is used. For example, a so-called Bosch process is used for the deep dry etching. In the Bosch process, etching and formation of a protective layer are alternately repeated.

In the Bosch process, for example, $SF_6$ gas is used for etching the silicon and $C_4F_8$ gas is used for forming a protective layer. When the $SF_6$ gas is used for etching, the etching advances both in depth and side directions. This hinders the formation of a deep hole or a groove. In the Bosch process, on the other hand, after the etching is performed for a certain time, the $C_4F_8$ gas is used instead of the $SF_6$ gas to deposit CFn polymer, generated with plasma, to form a layer inside the etched groove. Then again, the $SF_6$ gas is used to advance the etching. Because the etching rate for the side walls is lower than the etching rate for the bottom of the groove, only the bottom of the groove is etched. By alternately using the $SF_6$ gas and the $C_4F_8$ gas repeatedly, a deep groove with a high aspect ratio is formed.

Examples of etching conditions in the above-described Bosch process are as follows. Gas pressure is from 1 Pa to 10 Pa. A duration time for each of the $SF_6$ gas and the $C_4F_8$ gas is of the order of 5 seconds to 10 seconds. The power is 600 w. Under these conditions, the etching rate is, for example, 2 μm/minute, and the depth of the groove is 100 μm. To perform the etching using the Bosch process, it is important to generate high density plasma. There are various methods for producing the high density plasma including ICP (Inductively Coupled Plasma) and helicon wave.

Alternatively, a cryo process may be employed instead of the Bosch process to perform deep dry etching. In the cryo process, a substrate to be etched is cooled to −100° C. or below, and then the substrate is dry-etched using the $SF_6$ gas. It is difficult to etch a shape with a high aspect ratio using a normal dry etching method because the etching proceeds isotropically due to chemical reactions. In the cryo process, the temperature of the substrate to be etched is lowered to suppress chemical etching, allowing the etching of the shape with the high aspect ratio.

The dry etching is continued until the conductive substrate 18 is exposed from the bottom of the groove 20a. The etching rate in the conductive substrate 18 made of a metal plate is slower than that in the etching substrate 20 made of silicon, so the conductive substrate 18 functions as an etching stop layer. This improves uniformity in the depths of the grooves eventually, even if there is in-plane nonuniformity in the depths of the grooves due to a difference in the etching rates. Here, the Bosch process is used. Alternatively, anisotropic etching, for example, wet-etching utilizing orientations of silicon monocrystal may be used.

Figure 3F:
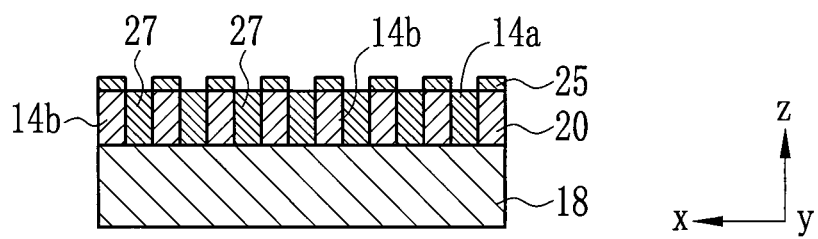

As shown in FIG. 3F, in the next step, the grooves 20a are filled with gold (Au) 27 by the electroplating method using the conductive substrate 18 as the seed layer to form the X-ray absorbing section 14a. To perform the electroplating, a current terminal is attached to the conductive substrate 18. For example, when the outer size of the conductive substrate 18 is made slightly larger than the size of the etching substrate 20, an outer region of the conductive substrate 18 is exposed to the outside even if the conductive substrate 18 and the etching substrate 20 are bonded together. The current terminal is attached to the exposed outer region of the conductive substrate 18.

The joint substrate composed of the etching substrate 20 and the conductive substrate 18 is immersed in plating liquid. An electrode (anode) is placed in a position opposing the joint substrate. Bypassing a current between the conductive substrate 18 and the electrode, metal ions in the plating liquid are deposited on the pattern-processed substrate. Thereby, the grooves 20a are filled with the Au 27. For the electroplating of the Au 27, for example, in cyan gold plating bath, $KAu(CN)_2$ is used as the plating liquid. By adding $KH_2PO_4$, KOH as a pH buffer agent to the plating liquid, pH is adjusted to a range from 6 to 8. The temperature of the plating liquid is set to a range from 25° C. to 70° C. Current density is set to a range from 0.2 $A/cm^2$ to 1 $A/cm^2$. Ti plated with Pt is used as an anode material. These conditions of the Au plating are examples. Other types of Au plating may be performed using different plating liquid or in different conditions.

After the X-ray absorbing sections 14a have been formed, as shown in FIG. 2B, the etch mask 25 is removed from the X-ray transmitting sections 14b. Thereby, the second grid 14 is formed. The second grid 14 is composed of the grid layer 17 and the conductive substrate 18. In this embodiment, the etching substrate 20 is made of silicon. This prevents the etching substrates 20 from sticking and distortion during the electroplating. Thus, a grid with high strength and high accuracy is produced. The conductive substrate 18 made of a metal plate is used as the seed layer for the electroplating. This prevents the seed layer from coming off during the electroplating. Additionally, the second grid 14 can be reinforced by the conductive substrate 18. The conductive substrate 18 has a thermal expansion coefficient substantially the same as that of the etching substrate 20. Accordingly, residual stress due to heat at the time of bonding the conductive substrate 18 and the etching substrate 20 does not occur.

Hereinafter, other embodiments of the present invention are described. In the following embodiments, the same numerals are assigned to the same parts as those in the configurations already described and the descriptions thereof are omitted. In each of the following embodiments, the first grid has the same or similar configuration to the second grid except the grid pitch, thickness, or the like, and is produced by the same production method as the second grid, so detailed descriptions of the first grid are omitted.

Second Embodiment

Figure 4A:
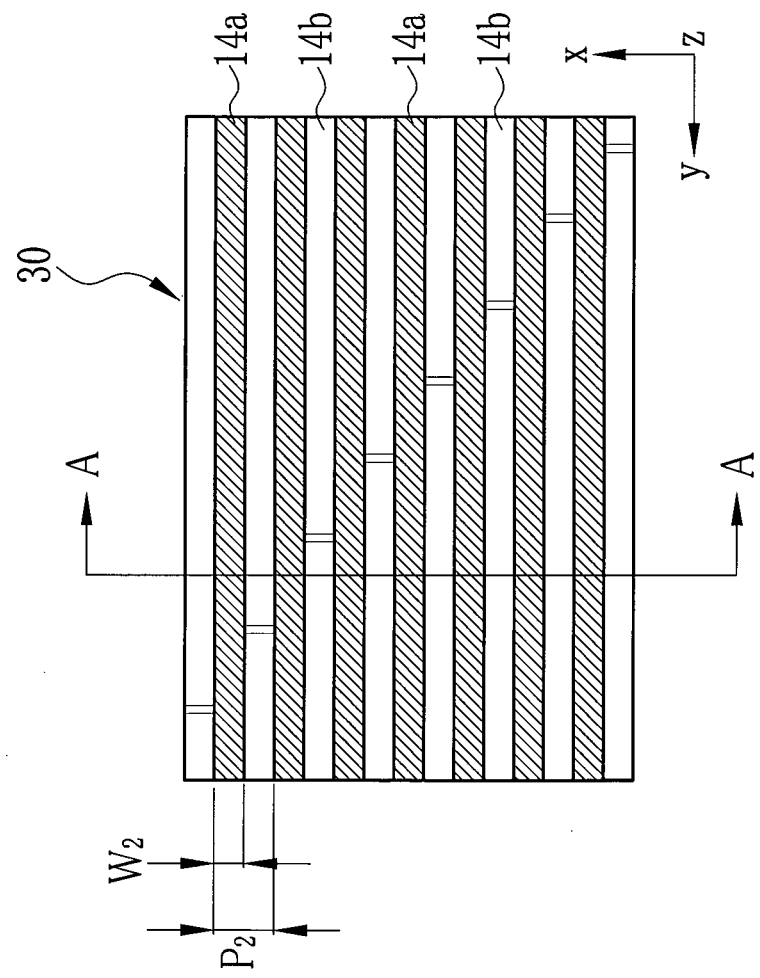
FIG. 4A is a plan view showing a second grid of a second embodiment.
Figure 4B:
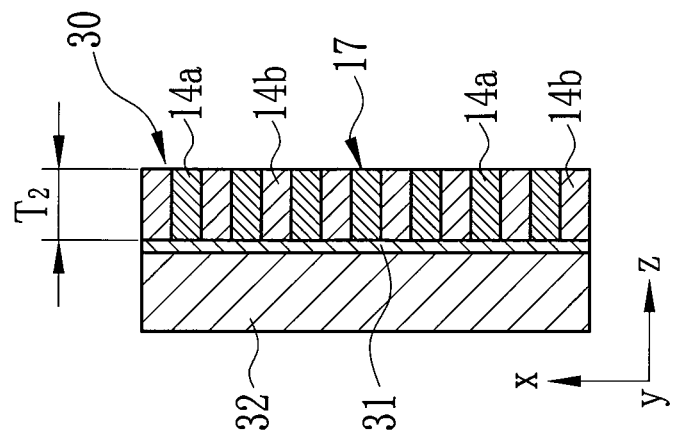
FIG. 4B is a cross-sectional view showing the second grid of the second embodiment.

In the first embodiment, the conductive substrate 18 made of a metal plate is used as the support layer for the grid layer 17 and as the seed layer for electroplating. Alternatively, a substrate composed of a plurality of layers may be used as the conductive substrate 18. FIG. 4A is a plan view showing a second grid 30 of this embodiment viewed from the X-ray image detector 15 side. FIG. 4B is a cross-section taken along a line A-A in FIG. 4A.

The second grid 30 is composed of the grid layer 17, a conductive thin-layer 31, and a support substrate 32. The grid layer 17 is composed of a plurality of the X-ray absorbing sections 14a and a plurality of the X-ray transmitting sections 14b. Each of the conductive thin-layer 31 and the support substrate 32 has X-ray transmission properties which do not interfere with the grid performance of the grid layer 17. The conductive thin-layer 31 is used as the seed layer for the electroplating during the production of the second grid 30. The support substrate 32 has sufficient rigidity to support the grid layer 17.

Instead of the second grid 14 of the first embodiment, the second grid 30 is used in the X-ray imaging system 10. As with the first embodiment, the X-ray imaging system 10 performs imaging for two or more times while the second grid 30 is moved translationally in the x direction. In each imaging step, the X-ray source 11 emits the X-ray to the object H. The second grid 30 changes or modulates the intensity of the fringe image of the object H generated by the first grid 13. The X-ray image detector 15 detects the fringe image with the intensity modulated by the second grid 30. The X-ray imaging system 10 obtains a phase differential image from a phase shift value of pixel data of each pixel in the X-ray image detector 15. The phase differential image is integrated along a fringe scanning direction. Thereby, a phase contrast image of the object H is generated. Thus, the second grid 30 of this embodiment can be used for the imaging of the phase contrast image in the same manner as in the first embodiment.

Figure 5A:
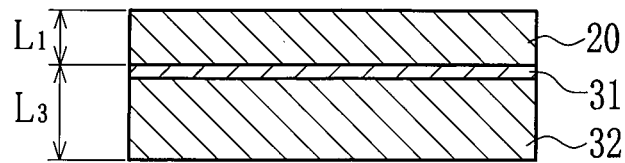
FIGS. 5A to 5F are explanatory views showing steps for producing the second grid of the second embodiment.

Next, a method for producing the second grid 30 is described. FIGS. 5A to 5F show steps for producing the second grid 30. Each of FIGS. 5A to 5F is a cross-section taken along an xz plane in FIG. 4. As shown in FIG. 5A, in a first step, the etching substrate 20 and the support substrate 32 formed with the conductive thin-layer 31 on its top face are bonded together. It is preferable that the conductive thin-layer 31 is, for example, a metal layer made of Au or Ni, or a metal layer composed of Al, Ti, Cr, Cu, Ag, Ta, W, Pb, Pd, Pt, or the like, or a metal layer made of their alloy. The conductive thin-layer 31 may be provided on the etching substrate 20. The conductive thin-layer 31 may be provided on each of the etching substrate 20 and the support substrate 32. Because the conductive thin-layer 31 has the thickness of the order of several μm, it does not affect the X-ray transmission properties even if a material with high X-ray absorption properties such as Au is used.

As with the conductive substrate 18 of the first embodiment, the support substrate 32 is made of a material with low X-ray absorption properties. The support substrate 32, however, does not require conductivity because the conductive thin-layer 31 is used as the seed layer. The material of the support substrate 32 preferably has a small difference in thermal expansion coefficient from the etching substrate 20. For the material of the support substrate 32, for example, borosilicate glass, soda-lime glass, quartz, alumina, GaAs, Ge, and the like are preferable. Further, silicon, also used as the material of the etching substrate 20, is preferable. Examples of the borosilicate glass include Pyrex (registered trademark) glass and TEMPAX (registered trademark) glass. The material with a small difference in thermal expansion coefficient from the etching substrate 20 is used as the material of the support substrate 32 in order to prevent distortion due to the thermal stress during the bonding and during the use. As with the thickness of the conductive substrate 18 of the first embodiment, the thickness L3 of the support substrate 32 including the conductive thin-layer 31 is larger than the thickness of the etching substrate 20, for example, of the order of 100 μm to 700 μm. The support substrate 32 may be made thicker than required before the bonding. The support substrate 32 may be polished to a predetermined value after the bonding.

To bond the etching substrate 20 and the support substrate 32, the diffusion bonding or the normal-temperature bonding may be used. In the diffusion bonding, the bonding is performed with the application of heat and pressure. In the normal-temperature bonding, surfaces are activated in a high vacuum and then bonded together. In addition, anodic bonding performed with the application of an electric field and heat in a vacuum or a method for bonding the substrates through a material such as In, AuSn, or the like, which melts with the application of heat, may be used. To perform the diffusion bonding of the conductive thin-layer 31 made of Au, the etching substrate 20 made of silicon, and the support substrate 32 made of silicon, for example, a bonding device capable of applying the temperature of 300° C. to 400° C. and the pressure of 5 kN to 40 kN is used. The time required for the diffusion bonding using this bonding device is of the order of 10 minutes.

Figure 5B:
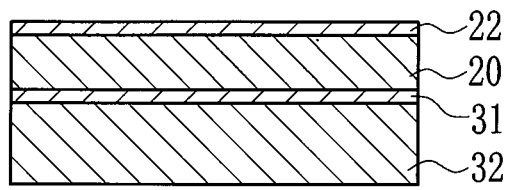
Figure 5C:
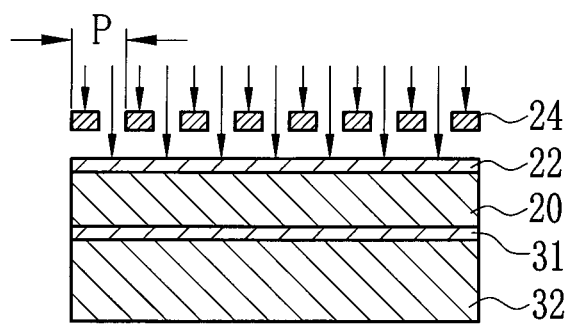
Figure 5D:
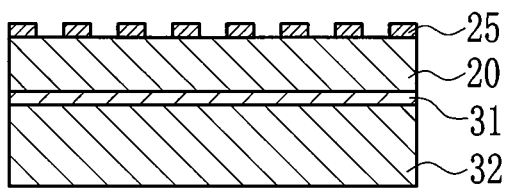
Figure 5E:
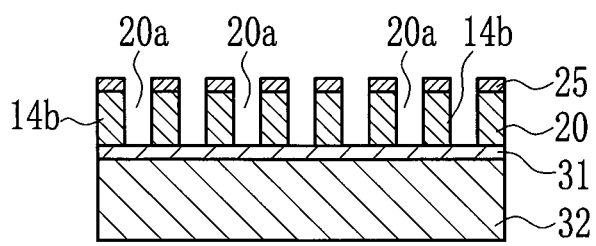
Figure 5F:
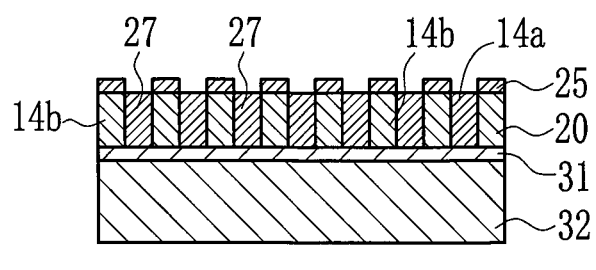

After the bonding of the etching substrate 20 and the support substrate 32, the steps the same as those described in the first embodiment are performed. First, as shown in FIGS. 5B to 5D, the etch mask 25 is formed on the etching substrate 20. Next, as shown in FIG. 5E, the grooves 20a and the X-ray transmitting sections 14b are formed on the etching substrate 20 using the Bosch process for dry etching. As shown in FIG. 5F, the grooves 20a are filled with the Au 27 using the electroplating. Thus, the X-ray absorbing sections 14a are formed.

According to this embodiment, the second grid 30 having a high aspect ratio is produced using the conductive thin-layer 31 and the support substrate 32 in the same manner as the first embodiment. Unlike the conductive substrate 18 of the first embodiment, the support substrate 32 does not require conductivity, providing greater flexibility in selecting a material with lower X-ray absorption properties.

Third Embodiment

Figure 6G:
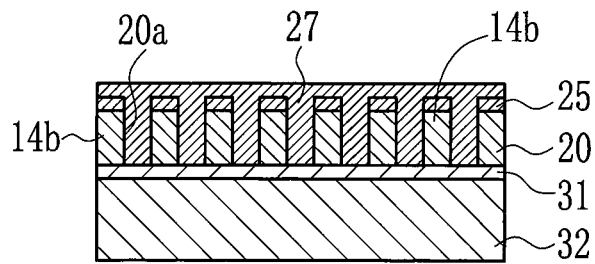
FIGS. 6G to 6J are explanatory views showing a method for producing a second grid of a third embodiment.
Figure 6H:
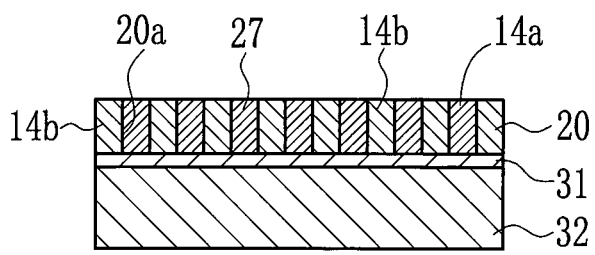

In the above embodiments, the grooves 20a are filled with the Au 27 by the electroplating method. Due to the in-plane distribution of the Au in the grooves 20a, however, the grooves 20a may be filled unevenly with the Au 27. To solve this problem, in this embodiment, as shown in a step of FIG. 6G performed after the step of FIG. 5F, the electroplating is performed such that the Au overflows the grooves 20a to cover the entire top face of the etching substrate 20. After the electroplating, as shown in FIG. 6H, the top face of the etching substrate 20 is polished. Thereby, the Au 27 and the etch mask 25 extending out of the grooves 20a are removed.

In the dry etching using the Bosch process, periodical recesses called scallops appear noticeably on the top face, which increase variations in width dimensions of the grooves 20a. Polishing the top face of the etching substrate 20 eliminates the scallops. The thickness of the etching substrate 20 to be polished to eliminate the scallops is, for example, equal to or larger than 5 µm.

Figure 6I:
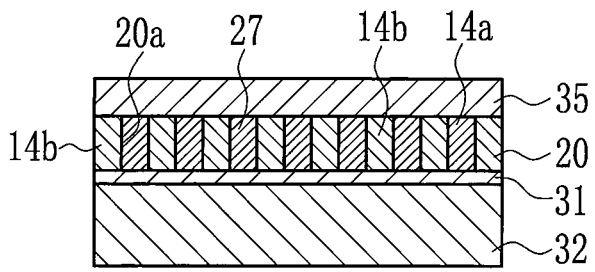
Figure 6J:
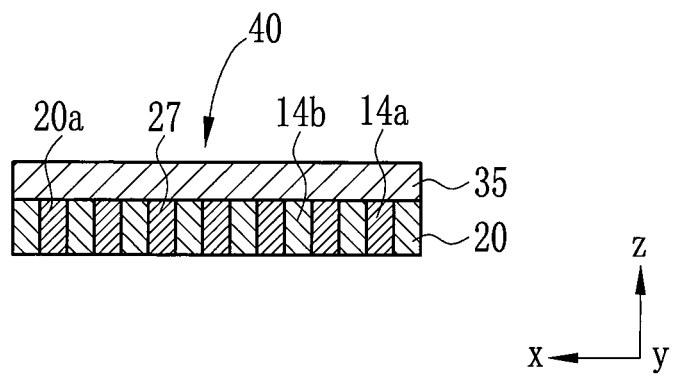

Because the above-described scallops also appear on the bottom face of the etching substrate 20 (though the scallops on the bottom face are less apparent than those in the top face), it is also preferable to polish the bottom face of the etching substrate 20. In this case, to ensure the ease of handling of the grid after being completed, it is preferable to provide a protective layer 35 on the top face of the etching substrate 20 as shown in FIG. 6I. As shown in FIG. 6J, the support substrate 32 and the conductive thin-layer 31 are polished and removed. The bottom face of the etching substrate 20 is polished so as to eliminate the scallops on the bottom face. For materials of the protective layer 35, organic materials with low X-ray absorption properties are preferable, for example, acryl, novolak resin, polyimide, parylene, and the like. Thereby, a second grid 40 thinner than that in the second embodiment is obtained.

Figure 7:
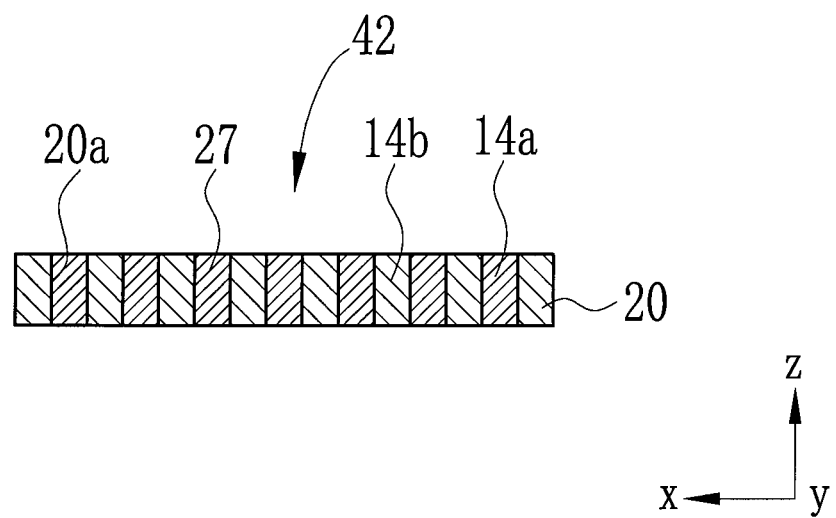
FIG. 7 is a cross-sectional view showing the second grid from which a conductive substrate has been removed after electroplating in the third embodiment.
Figure 8:
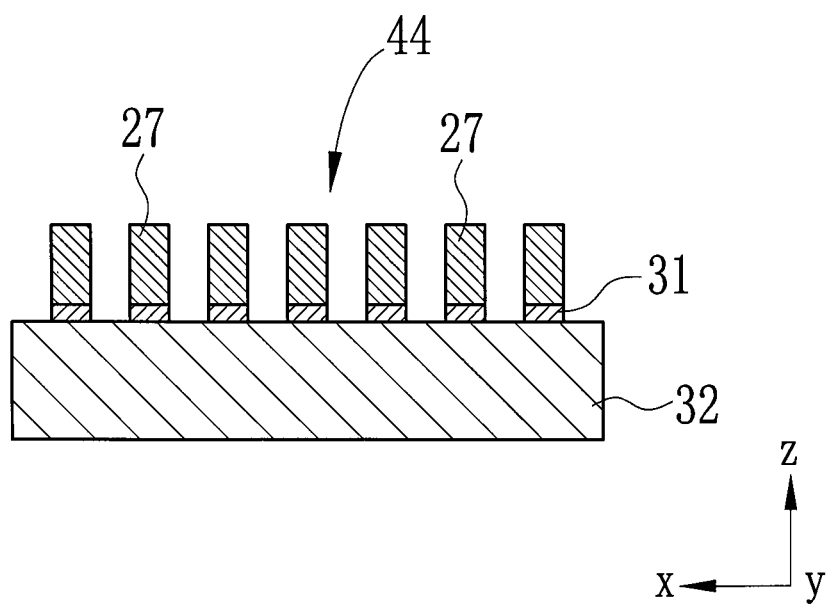
FIG. 8 is a cross-sectional view showing a second grid from which an X-ray transmitting section has been removed after the electroplating in the third embodiment.

Like a second grid 42 shown in FIG. 7, the protective layer 35 may be removed after the bottom face of the etching substrate 20 is polished. Like a second grid 44 shown in FIG. 8, after the electroplating, the X-ray transmitting sections 14b between the X-ray absorbing sections 14a may be removed by etching using the X-ray absorbing sections 14a as masks. Removing the support substrate 32 or the X-ray transmitting sections 14b increases the X-ray transmission properties by an amount corresponding to the support substrate 32 or the X-ray transmitting sections 14b. As shown in FIG. 7, when the thickness of the etching substrate 20 is equal to or larger than 100 µm after the removal of the support substrate 32, the etching substrate 20 maintains required rigidity of the substrate.

Fourth Embodiment

In the above embodiments, the etching substrate 20 (second substrate) is made of silicon. When the silicon has conductivity, however, the etching substrate 20 functions as the seed layer during the electroplating. This may cause insufficient filling of the Au 27 inside the groove 20a. When amounts of the Au 27 in the grooves 20a vary, the X-ray absorption properties of the grid become nonuniform, and thereby the grid performance is reduced.

Figure 9A:
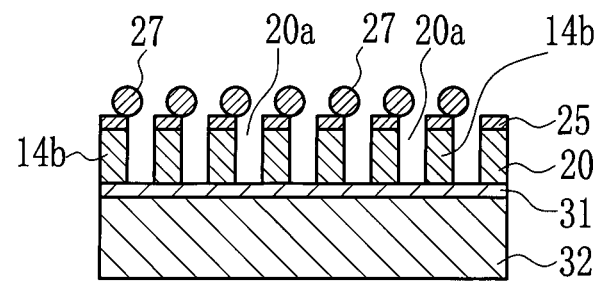
FIGS. 9A and 9B are cross-sectional views showing an electroplating failure occurred when the conductivity of the etching substrate is high.
Figure 9B:
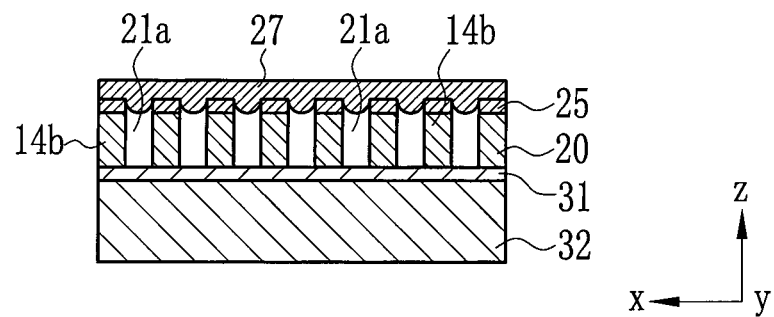
Figure 10A:
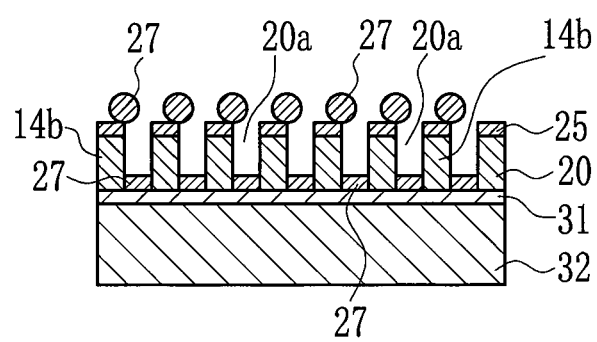
FIGS. 10A and 10B are cross-sectional views showing an electroplating failure occurred when the conductivity of the etching substrate is relatively low.
Figure 10B:
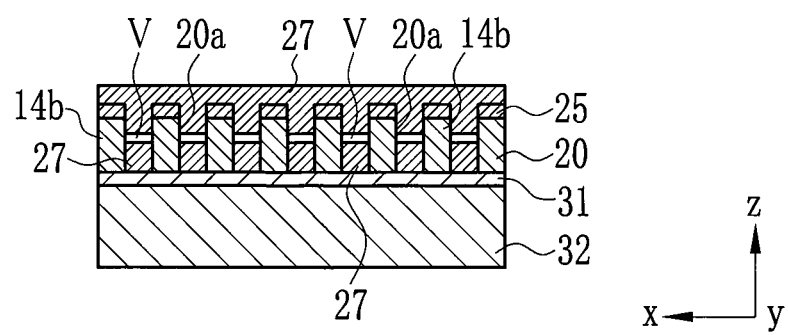

For example, as shown in FIG. 9A, when the etching substrate 20 has conductivity, the electroplating of the Au 27 starts not from the conductive thin-layer 31 side below the etching substrate 20 but from the top face of the etching substrate 20. Then, as shown in FIG. 9B, the electroplating started from the top face of the etching substrate 20 proceeds in the lateral direction and in the upward direction without filling the bottom portions of the grooves 20a. On the other hand, as shown in FIG. 10A, when the conductivity of the etching substrate 20 is relatively low, the electroplating starts from the conductive thin-layer 31 side and from the top face of the etching substrate 20 at the same time. As a result, as shown in FIG. 10B, a void V is formed in a middle portion of each of the grooves 20a.

Figure 11:
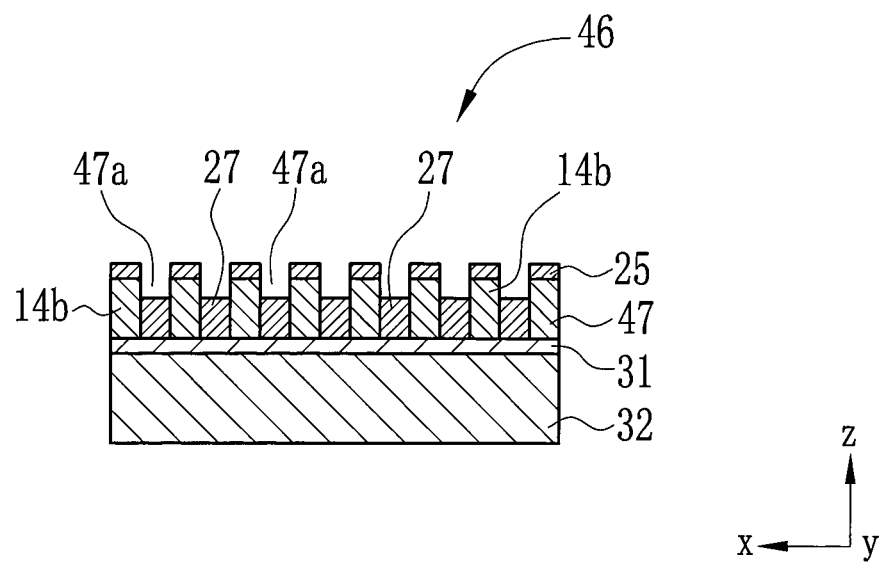
FIG. 11 is a cross-sectional view showing the electroplating performed in a fourth embodiment using the etching substrate having a specific resistance equal to or larger than 100 $\Omega$·cm.

To solve the above problems, as shown in FIG. 11, a second grid 46 of this embodiment employs an etching substrate 47 made of nonconductive silicon or silicon with the specific resistance equal to or larger than 100 Ω·cm. In this case, the electroplating is not affected by the conductivity of the etching substrate 47. Thereby, grooves 47a of the etching substrate 47 are filled with the Au 27 from the conductive thin-layer 31 side. Because the silicon with the specific resistance equal to or larger than 100 Ω·cm is high-purity silicon that contains no impurities, the X-ray transmission properties of the X-ray transmitting sections 14b is improved.

Fifth Embodiment

Figure 12:
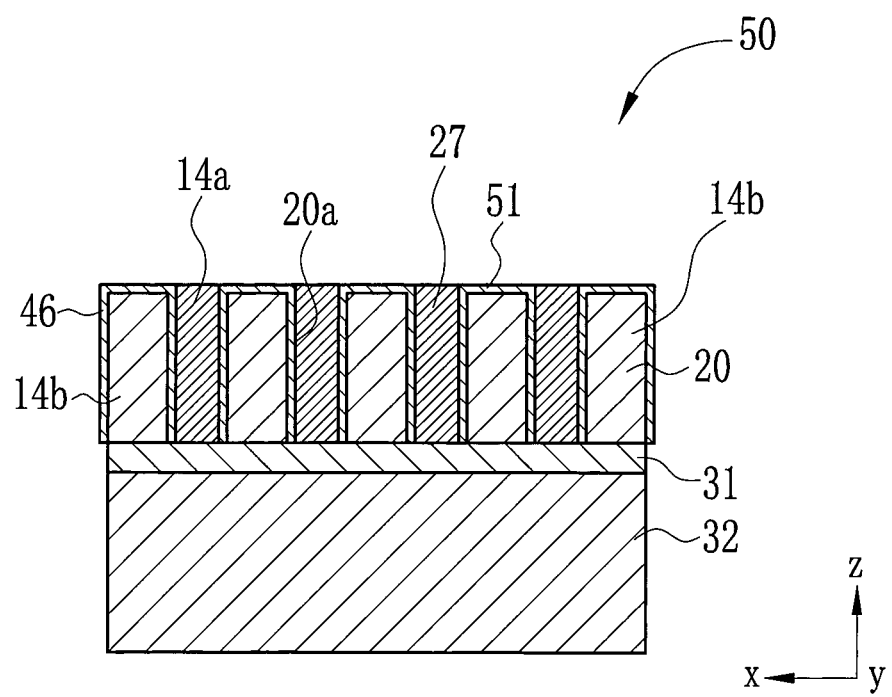
FIG. 12 is a cross-sectional view showing the etching substrate with an insulating layer formed on its surface in a fifth embodiment.

In the fourth embodiment, silicon with the specific resistance equal to or larger than 100 Ω·cm is used for producing the etching substrate. Instead, like a second grid 50 of this embodiment shown in FIG. 12, an insulating layer 51 may be formed on the surface of the etching substrate 20 to increase the specific resistance of the etching substrate 20. To provide the insulating layer 51 on the entire surface of the etching substrate 20, for example, an insulating material such as $SiO_2$ or $Si_3N_4$ is applied or deposited onto the surface of the etching substrate 20 by plasma CVD. Alternatively, an electric current may be applied to the conductive thin-layer 31 in a solution to anodize the surface of the etching substrate 20. To provide the insulating layer 51 on a part of the surface of the etching substrate 20, for example, $SiO_2$ may be deposited using sputtering, vapor deposition, or the like.

To flow the plating liquid in the grooves 20a smoothly, it is preferable that the surfaces of the grooves 20a are lypophilic to the plating liquid. Particularly, many of the plating liquids are water solutions, so it is preferable that the surfaces of the grooves 20a are hydrophilic. Normally, hydrophilic property is reduced only by leaving the grooves in the air due to deposition of oil from the air. To improve the hydrophilic property, ashing of oil is performed using O2 plasma. The effect, however, is insufficient when the grooves 20a are deep. For this reason, it is more preferable to use an insulating material with both the insulating and hydrophilic properties, for example, $TiO_2$ or ZnO, or at least one of those to form the insulating layer 51 formed on the surface of the etching substrate 20. In particular, it is known that $TiO_2$ increases its hydrophilic property by application of UV rays, so it is more preferable for the material of the insulating layer 51. The insulating layer 51 may not necessarily cover the entire surface of the etching substrate 20, and may cover only a part of the surface thereof.

The insulating layer 51 may be formed using an ion implantation device for doping the silicon. The ion implantation device performs ion implantation to the etching substrate 20 at a predetermined angle to damage the surface of the etching substrate 20 to reduce the conductivity. Thereby, the insulating layer 51 is formed. For example, the ion implantation is performed at an angle of ion beam emission of 1° relative to the depth direction of the groove 20a of the etching substrate 20 while the etching substrate 20 is rotated. Hydrogen is used as an ion source with the ion beam energy of 300 keV. The width is of the order of 3 µm. Thereby, the insulating layer 51 is formed on the entire surface of the etching substrate 20. The second grid 50 produced according to this embodiment has the insulating grooves 51 on the inner walls of the grooves 20a. Thereby, the diffusion of the Au 27 into the etching substrate 20 is suppressed.

Sixth Embodiment

In the second embodiment and the like, the diffusion bonding is performed at a low temperature of the order of 400° C. to bond the etching substrate 20 made of silicon and the conductive thin-layer 31 made of the Au. It is known, however, the diffusion bonding causes voids at the interface between the etching substrate 20 and the conductive thin-layer 31 due to unevenness caused by the deposition of the Au, and the low bonding temperature resulting in insufficient removal of residues (dust or the like) from the surface, and coagulation of the Au by diffusion. When the voids are formed between the etching substrate 20 and the conductive thin-layer 31, the grid layer 17 is likely to come off from the conductive thin-layer 31, and thereby causing image defects. This significantly affects the quality of the grid. To solve this problem, in this embodiment, the conductive substrate or the conductive thin-layer is made of the semiconductor of the same material as the etching substrate. Hereinafter, this embodiment is detailed.

Figure 13A:
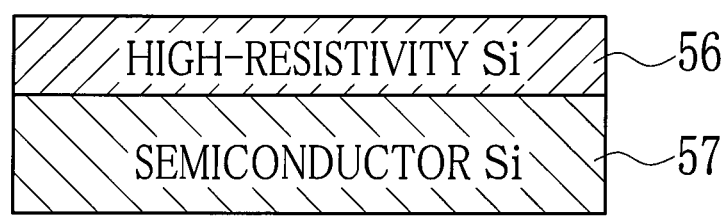
FIGS. 13A and 13B are cross-sectional views showing the conductive substrate made of semiconductor silicon of the sixth embodiment.

As shown in FIG. 13A, as with the first embodiment, a second grid 55 (see FIG. 13B) is composed of an etching substrate 56 and a conductive substrate 57. Both the etching substrate 56 and the conductive substrate 57 are made of silicon. The conductive substrate 57 is semiconductor silicon doped with one or more impurities so that the conductive substrate 57 functions as the seed layer. An amount of the one or more impurities doped is, for example, of the order of $1 \times 10^{18}$ cm$^{-3}$. Substances with low X-ray absorption properties, namely, elements with a small atomic number are preferable as impurities to be doped. As with the fourth embodiment, the etching substrate 56 is made of high-resistivity silicon having the specific resistance higher than the conductive substrate 57, for example, equal to or larger than 100 Ω·cm. In this embodiment, the semiconductor is defined to have the resistivity within a range from $10^{-4}$ to $10^{12}$ Ω·cm. The conductor (metal) is defined to have the resistivity equal to or smaller than $10^{-4}$ Ω·cm.

For the bonding of the etching substrate 56 and the conductive substrate 57, for example, common direct bonding is used for bonding the silicon. In this direct bonding, the surfaces of the etching substrate 56 and the conductive substrate 57 are processed with a chemical agent such as acid and pure water, and then the surfaces are put together and heat-processed. Thus, the surfaces are tightly bonded to each other. The heat-process for the direct bonding is performed at high temperature, for example, of the order of 1000° C. Excellent flatness of the silicon and reduction in the residues substantially reduces the occurrence of voids.

Figure 13B:
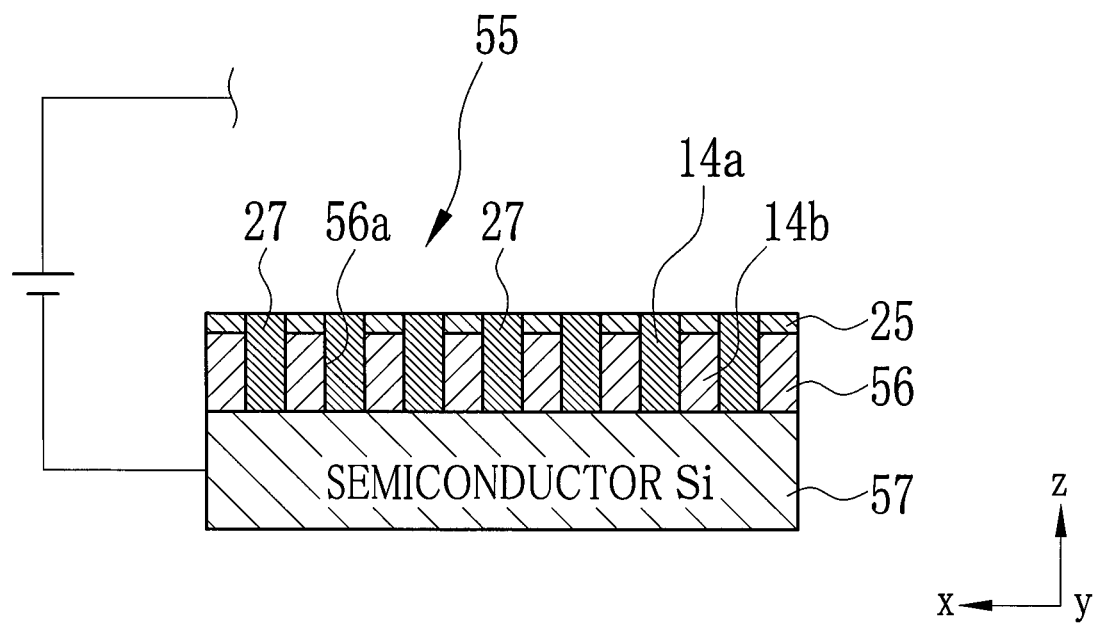

Etching steps for forming grooves 56a in the etching substrate 56 are the same as those described in the first embodiment as shown in FIGS. 3B to 3E, so detailed descriptions are omitted. As shown in FIG. 13B, in the electroplating step, the conductive substrate 57 is used as the seed layer. As with the first embodiment, the Au 27 is filled in the grooves 56a. As described above, the surface of the conductive substrate 57 does not have unevenness caused by the bonding. Accordingly, the occurrence of voids due to the unevenness is reduced. Because the etching substrate 56 uses high-resistivity silicon, the filling of the Au 27, as shown in FIG. 9, does not start from the top face of the etching substrate 56. Thus, the image defect due to the voids in the grooves 56a is prevented.

In this embodiment, the etching substrate 56 is made of the high-resistivity silicon. As with the fifth embodiment, the surface of the etching substrate may be insulated or provided with the insulating layer such as SiO$_2$. Further, when a current terminal for plating is formed or attached to the conductive substrate 57, a current barrier, which hinders the current flow, may be formed between the current terminal and the conductive substrate 57 of the semiconductor. In this case, for example, metal to provide ohmic contact is deposited on an area of the conductive substrate 57, to which the current terminal is formed, using vapor deposition of the like, and then heat treatment is applied thereto. When the conductive substrate 57 with the p-type conductivity is used, for example, Al, Cu, Pt, or the like may be deposited using vapor deposition, and the heat treatment at several hundreds degrees centigrade may be performed. Thus, a terminal providing the ohmic contact is formed.

Seventh Embodiment

Figure 14:
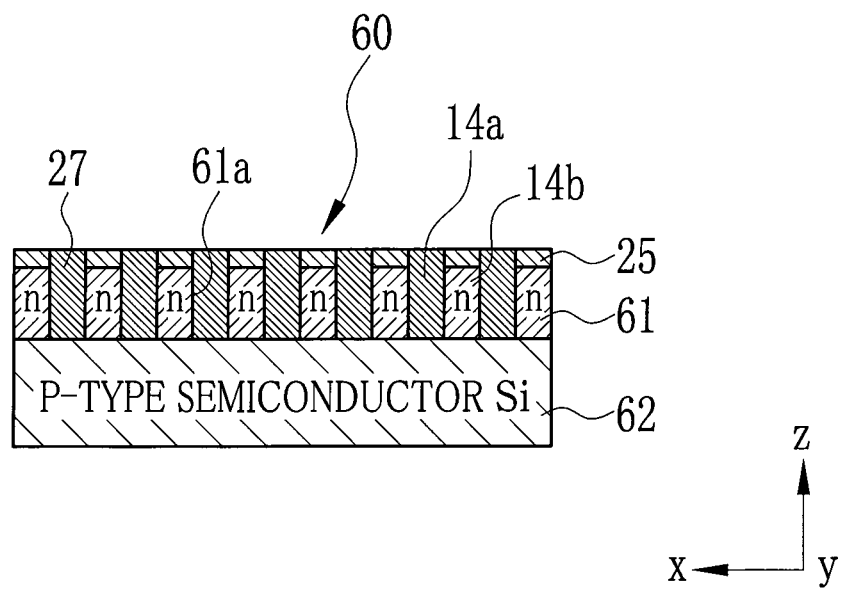
FIG. 14 is a cross-sectional view showing a conductive substrate made of a p-type semiconductor and an etching substrate made of an n-type semiconductor in a seventh embodiment.

Like a second grid 60 of this embodiment shown in FIG. 14, a silicon etching substrate 61 may be composed of a semiconductor substrate of one conductivity type (n-type semiconductor), and a silicon conductive substrate 62 may be composed of a semiconductor substrate of opposite conductivity type (p-type semiconductor). Thereby, the etching substrate 61 and the conductive substrate 62 are connected in reverse bias, which blocks a current flow from the conductive substrate 62 to the etching substrate 61. This prevents the plating from advancing from the top face side of the etching substrate 61. To convert the etching substrate 61 and the conductive substrate 62 into semiconductors, the amount of the one or more impurities to be doped is, for example, equal to or larger than $1 \times 10^{16}$ cm$^{-3}$. The specific resistance after the doping may be, for example, equal to or smaller than 100 Ω·cm. Substances with low X-ray absorption properties, namely, elements with a small atomic number are preferable as impurities to be doped. In the case of using an electroplating method that makes the conductive substrate 62 anodic, the polarity of the etching substrate 61 and the conductive substrate 62 may be reversed.

In the first and second grids, the Au 27 may be diffused into the etching substrate and the conductive substrate when the X-ray emission evolves heat to the Au 27. When the Au 27 is diffused into the etching substrate and the conductive substrate, the X-ray absorption properties of the Au 27 and the X-ray transmission properties of the etching substrate and the conductive substrate are reduced. In this embodiment, however, n-type semiconductor silicon doped with one or more impurities is used for the etching substrate 61, and p-type semiconductor silicon doped with one or more impurities is used for the conductive substrate 62, suppressing the diffusion of the Au 27 compared to the silicon with no doping. Thus, the reduction in the grid performance due to the heat of the Au 27 is prevented.

Eighth Embodiment

Figure 15:
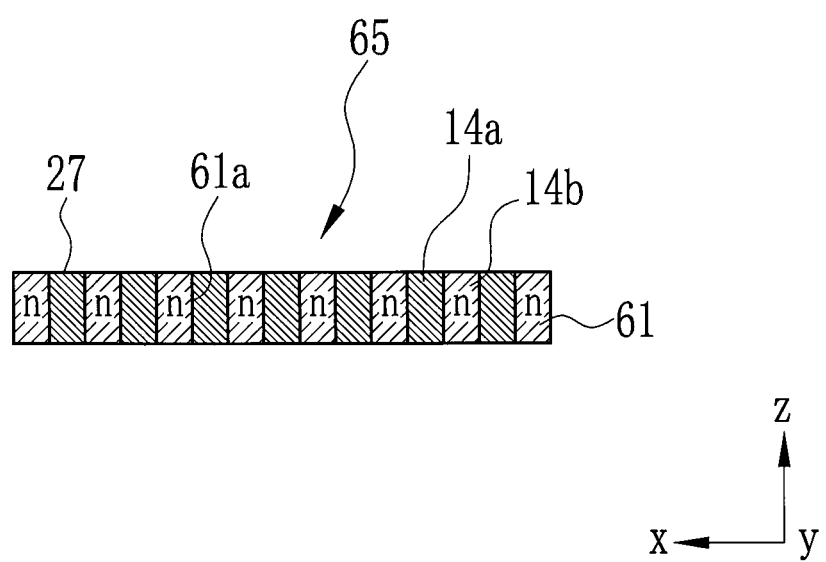
FIG. 15 is a cross-sectional view showing a second grid from which the conductive substrate has been removed after the electroplating in eighth embodiment.
Figure 16:
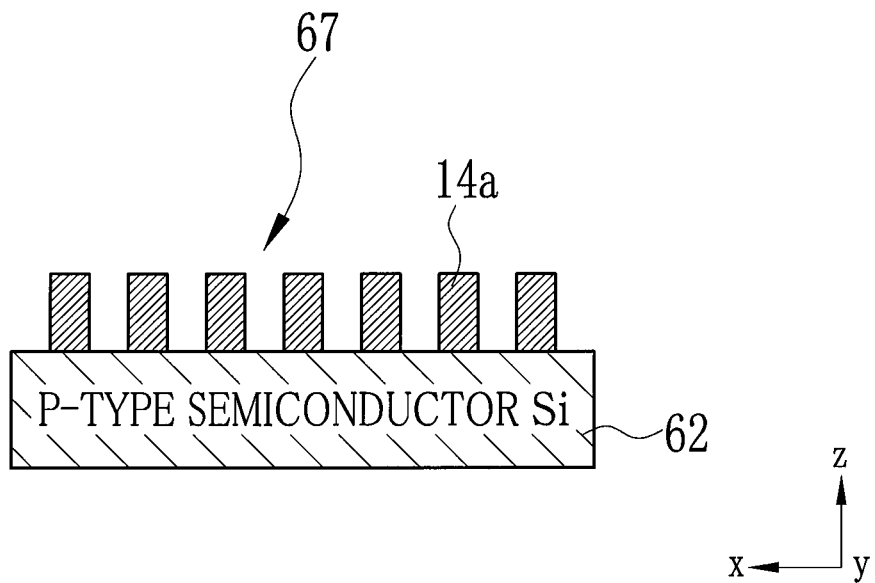
FIG. 16 is a cross-sectional view showing the second grid from which the X-ray transmitting section has been removed after the electroplating in the eighth embodiment.

As shown in FIG. 15, the conductive substrate 62 is removed from the second grid 60 of the seventh embodiment to form a second grid 65 composed of the X-ray absorbing sections 14a and the X-ray transmitting sections 14b of an n-type semiconductor. As shown in FIG. 16, the second grid 60 of the seventh embodiment may be etched using the X-ray absorbing section 14a as a mask to remove the X-ray transmitting section 14b between the X-ray absorbing sections 14a. Thereby, a second grid 67 composed of the conductive substrate 62 of the p-type semiconductor and the X-ray absorbing sections 14a is formed. The X-ray transmission properties are improved by an amount corresponding to the etching substrate 61 or the conductive substrate 62. Because the semiconductor doped with one or more impurities suppresses diffusion of the Au 27, deterioration in properties of the grid is prevented.

Ninth Embodiment

Figure 17:
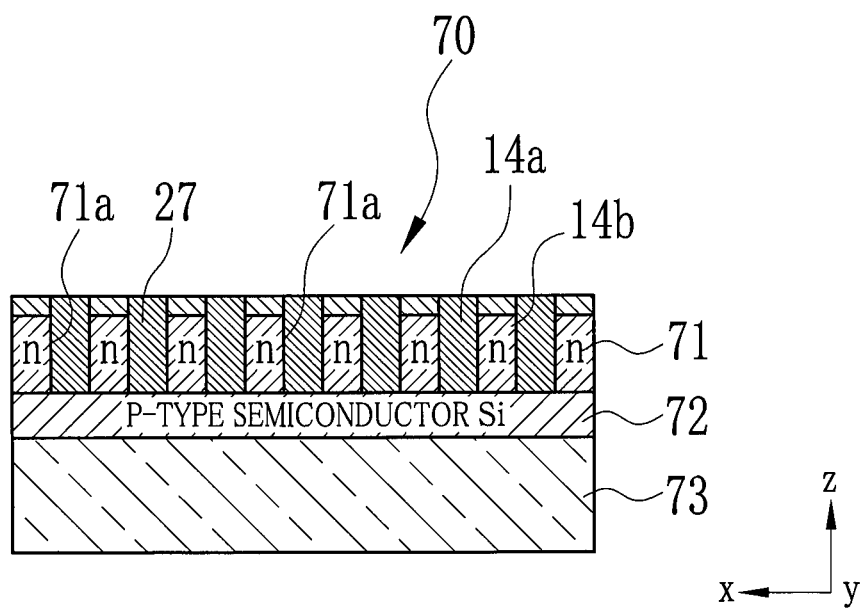
FIG. 17 is a cross-sectional view showing a conductive thin-layer made of the p-type semiconductor and an etching substrate made of an n-type semiconductor in a ninth embodiment.

In the seventh embodiment, the grid with the conductive substrate is described by way of example. Like a second grid 70 shown in FIG. 17, an etching substrate 71 is made of the n-type conductor silicon and a conductive thin-layer 72 is made of the p-type conductor silicon. A support substrate 73 may be made of an insulating material such as glass. Thereby, the p-type and n-type semiconductors provide prevention effect of the Au 27 diffusion even if the conductive thin-layer is used. As with the sixth embodiment, the etching substrate 71 may be made of high-resistivity silicon, and the conductive thin-layer 72 may be made of semiconductor silicon. As with the eighth embodiment, the conductive thin-layer 72, the support substrate 73, or the X-ray transmitting sections 14b may be removed after the plating step.

In the sixth to ninth embodiments, the semiconductor silicon is used. Any of Ge, GaAs, InP, GaP, SiC, or IGZO semiconductor silicon doped with one or more impurities may be used. An organic semiconductor such as pentacene or perfluorophthalocyanine may be used.

10$^{th}$ Embodiment

Figure 18:
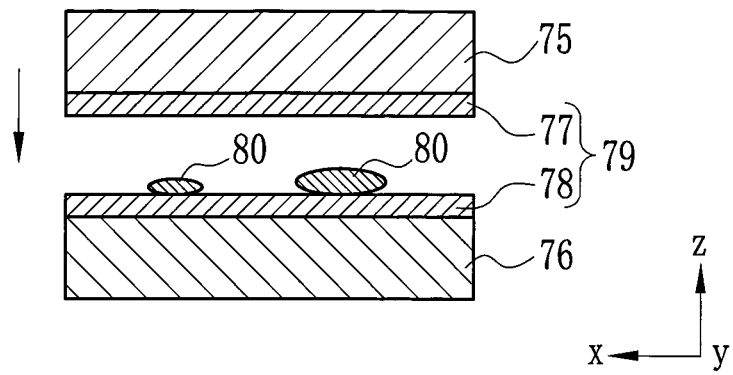
FIG. 18 is a cross-sectional view showing the etching substrate and the support substrate with their bonding surfaces provided with the conductive thin-layers in a $10^{th}$ embodiment.

In the above second embodiment, the conductive thin-layer 31 is provided on the support substrate 32. As shown in FIG. 18, a first conductive thin-layer 77 may be formed on a bonding surface of an etching substrate 75. A second conductive thin-layer 78 may be formed on a bonding surface of a support substrate 76. The first and second conductive thin-layers 77 and 78 may be bonded together to form a seed layer 79. The first and second conductive thin-layers 77 and 78 may be bonded together using diffusion bonding, normal-temperature bonding, or anodic bonding in the same manner as the above embodiments.

Figure 19A:
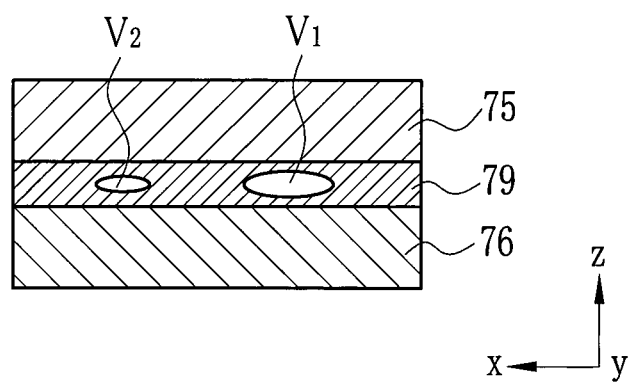
FIG. 19A is a cross-sectional view showing voids in the joint conductive thin-layers in the $10^{th}$ embodiment.
Figure 19B:
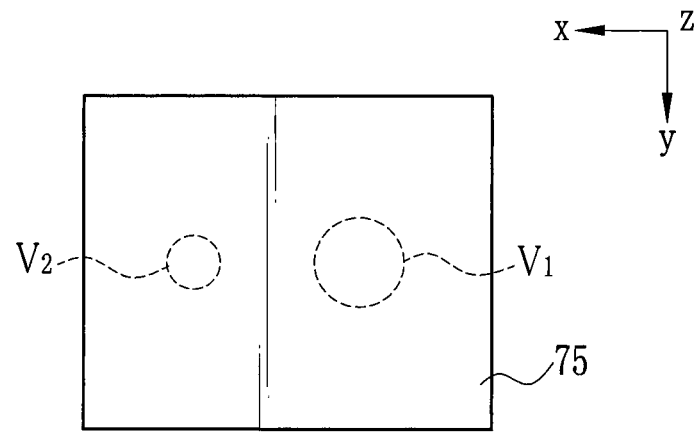
FIG. 19B is a plan view showing voids in the joint conductive thin-layers in the $10^{th}$ embodiment.

At the time of bonding the etching substrate 75 and the support substrate 76, dust may remain on the first conductive thin-layer 77 or the second conductive thin-layer 78. The surfaces of the first and second conductive thin-layers 77 and 78 may be uneven or gas absorbed by the first and second conductive thin-layers 77 and 78 may be released by the heat generated by the bonding. As shown in FIG. 18, if foreign matter 80 such as dust or gas exists between the first conductive thin-layer 77 and the second conductive thin-layer 78, or the surface of the first or second conductive thin-layer 77 or 78 is uneven at the time of bonding the etching substrate 75 and the support substrate 76, voids V1 and V2 may be formed inside the seed layer 79 as shown in FIG. 19A and its plan view, FIG. 19B. The voids V1 and V2 may be in the size of the order of 1 mm to 10 mm, which is extremely larger than the grid pitch of several μm.

Figure 22:
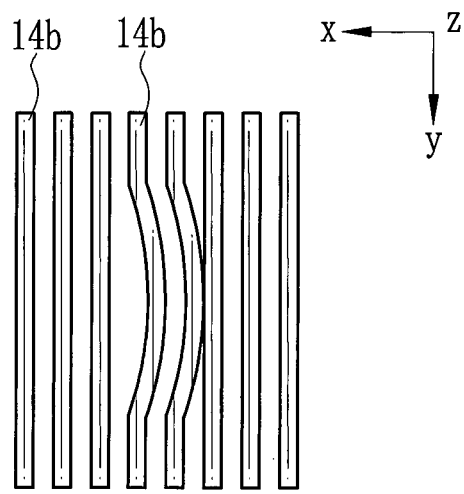
FIG. 22 is a plan view showing that the X-ray transmitting sections which have been come off from the void are distorted in the $10^{th}$ embodiment.

When the etching substrate 75 is polished to make it thinner in a state that the voids V1 and V2 are formed in the seed layer 79, for example, the etching substrate 75 may come off from the void V1 as shown in FIGS. 20A and 20B. Even if the etching substrate 75 does not come off from the void V2 during the polishing, the X-ray transmitting sections 14b above the void V2 may be separated from the seed layer 79 due to stress caused by the void V2 when grooves 75a and the X-ray transmitting sections 14b are formed on the etching substrate 75 as shown in FIGS. 21A and 21B. FIG. 22 is a plan view in which a portion including the void V2 shown in FIG. 21B is enlarged. The separation from the seed layer 79 distorts the X-ray transmitting sections 14b. A defect of the grid caused by the voids V1 and V2 often reaches a millimeter level, causing the grid to be unusable (production failure). As a result, production yields decrease.

Figure 23A:
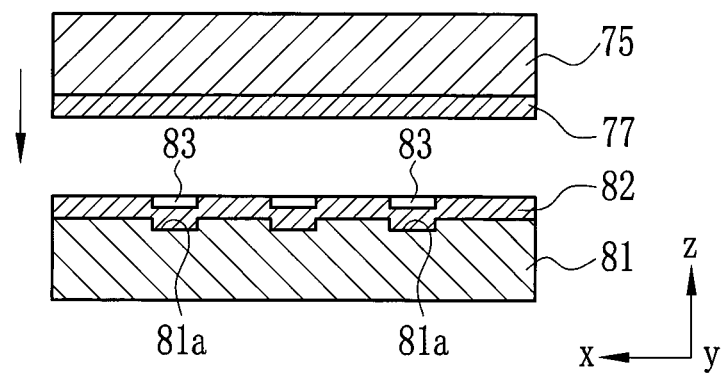
FIG. 23A is a cross-sectional view showing the conductive thin-layer with a plurality of concave portions in the $10^{th}$ embodiment.
Figure 23B:
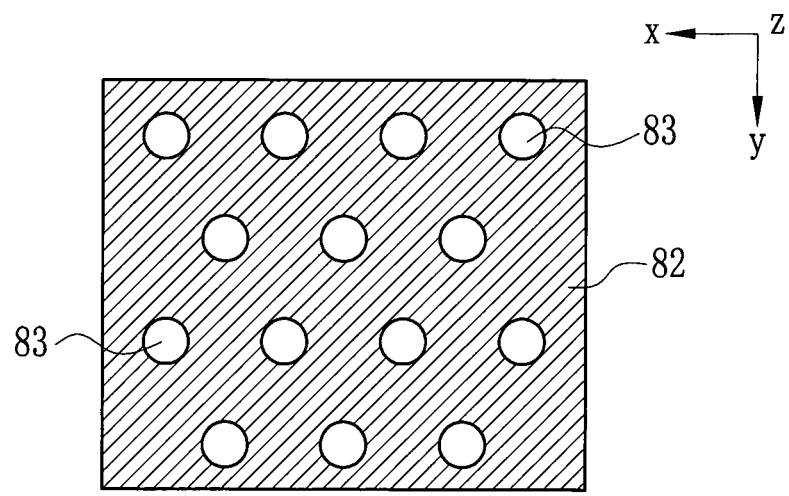
FIG. 23B is a plan view showing the conductive thin-layer with a plurality of concave portions in the $10^{th}$ embodiment.

To solve the above problem, in this embodiment, as shown in FIG. 23, a plurality of depression portions 83 with micro-size are formed on a second conductive thin-layer 82 of a support substrate 81. In consideration of influence to a phase contrast image, it is preferable that each of the depression portions 83 is equal to or smaller than a pixel size (for example, 150 μm per side) in x and y directions of the X-ray image detector. For example, it is preferable that each depression portion 83 is 50 μm in diameter and 0 μm to 10 μm in depth. An interval between the depression portions 83 is preferably equal to or larger than 500 μm, for example.

According to this embodiment, voids formed between the first conductive thin-layer 77 and the second conductive thin-layer 82 are dispersed and included in a plurality of the depression portions 83. Thus, the voids at the millimeter level do not occur. Coming off of the etching substrate 75 and distortion of the X-ray transmitting sections 14b due to the large voids are prevented. The depression portions 83 reduce a contact area between the first conductive thin-layer 77 and the second conductive thin-layer 82. Thereby, loads applied to the contact area during the bonding increase. As a result, bonding strength increases.

Figure 24:
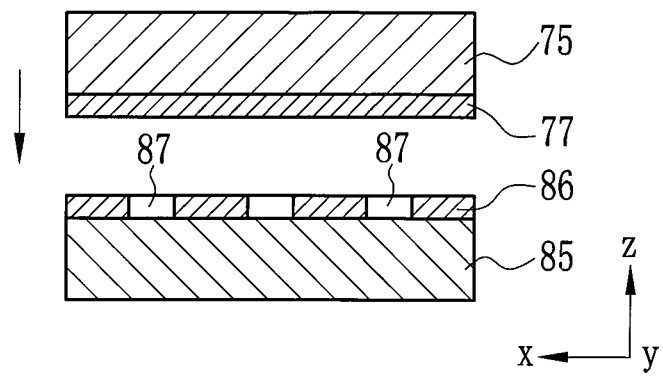
FIG. 24 is a cross-sectional view with another configuration of concave portions in the $10^{th}$ embodiment.

To form the depression portions 83, a plurality of depressions 81a are formed by etching in the support substrate 81 using an etch mask (not shown). A conductive thin-layer 82 of Au or the like is formed on the support substrate 81 by vapor deposition or the like. As shown in FIG. 24, a conductive thin-layer 86 deposited on a support substrate 85 may be etched using the etch mask to form a plurality of depression portions 87. It is preferable that the diameter, the depth, and the interval of the depression portions 87 are substantially the same as the above depression portions 83.

11th Embodiment

Figure 25:
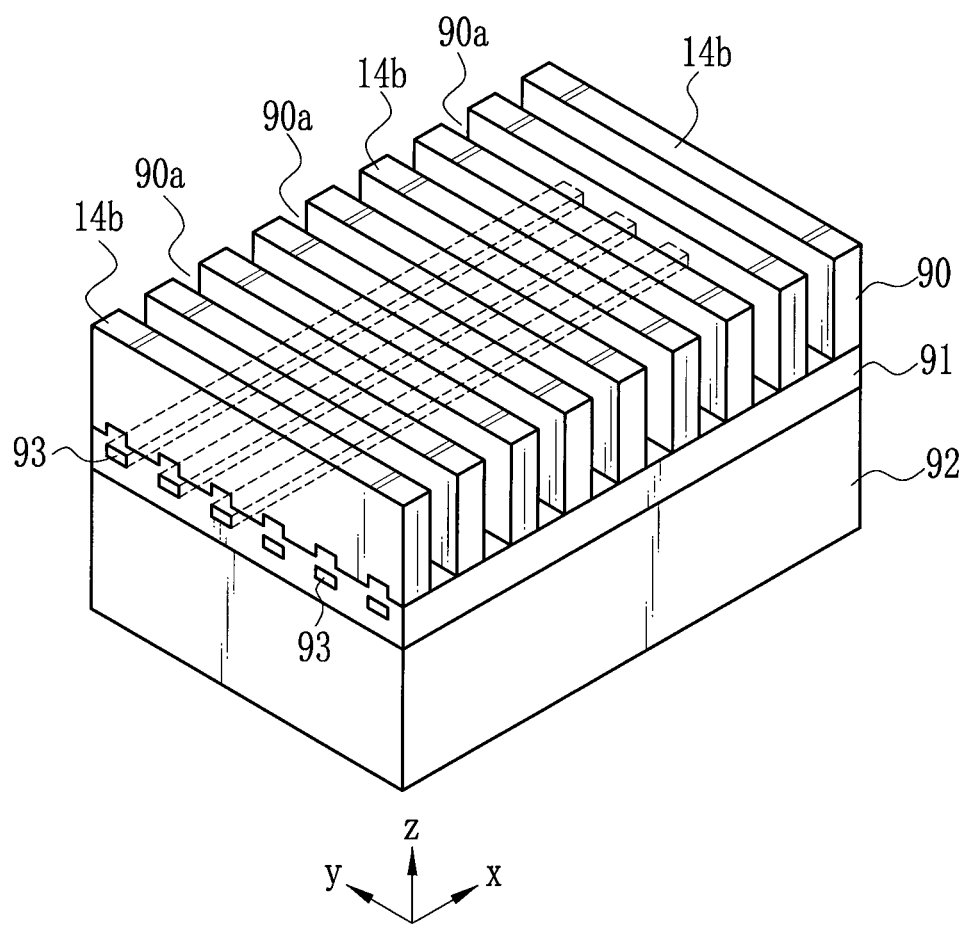
FIG. 25 is a perspective view showing linear concave portions provided in a seed layer in an $11^{th}$ embodiment.

In FIG. 25, an etching substrate 90, a seed layer 91, and a support substrate 92 form a layer structure. Grooves 90a and the X-ray transmitting sections 14b are formed on the etching substrate 90. In this embodiment, instead of the circular depression portions 83 of the 10$^{th}$ embodiment, a plurality of linear depression portions 93 are provided along the arranging direction (x direction) of the X-ray transmitting sections 14b.

Figure 26A:
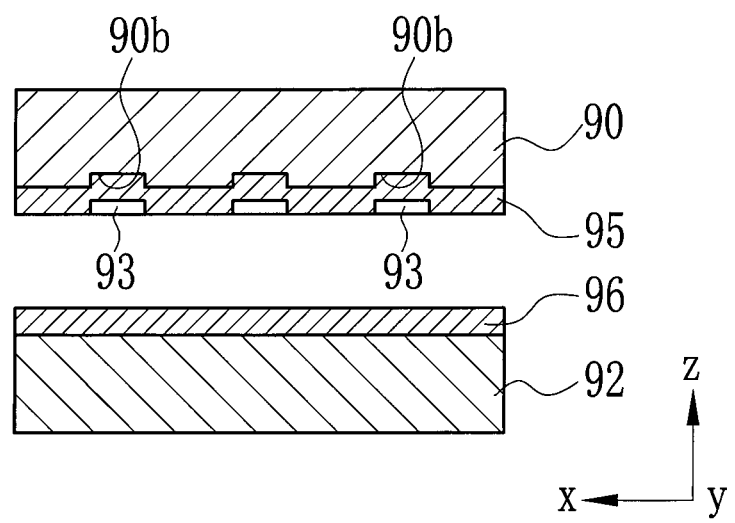
FIG. 26A is a cross-sectional view showing a plurality of linear concave portions provided in the conductive thin-layer in the $11^{th}$ embodiment.
Figure 26B:
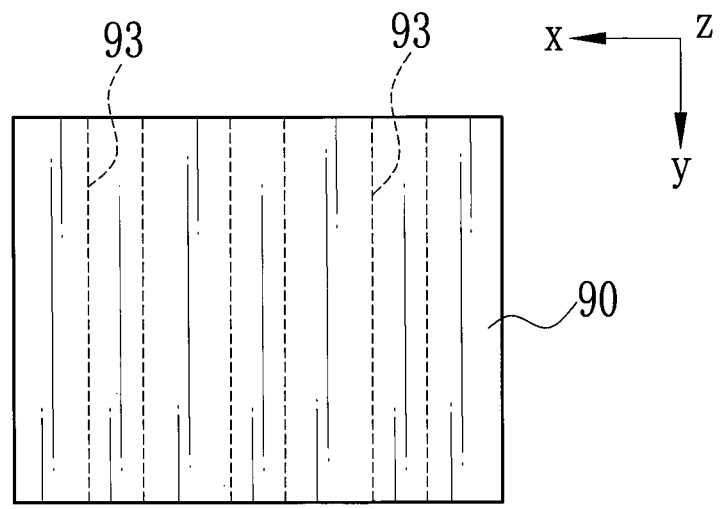
FIG. 26B is a plan view showing a plurality of linear concave portions provided in the conductive thin-layer in the $11^{th}$ embodiment.

As shown in FIG. 26A and its plan view, FIG. 26B, to form the depression portions 93, a plurality of depressions 90b are formed by etching using an etch mask (not shown) on the etching substrate 90. A first conductive thin-layer 95 of Au is formed on a plane provided with the depressions 90b on the etching substrate 90 by vapor deposition or the like. The seed layer 91 is composed of the first conductive thin-layer 95 and a second conductive thin-layer 96 provided on the support substrate 92.

Figure 27A:
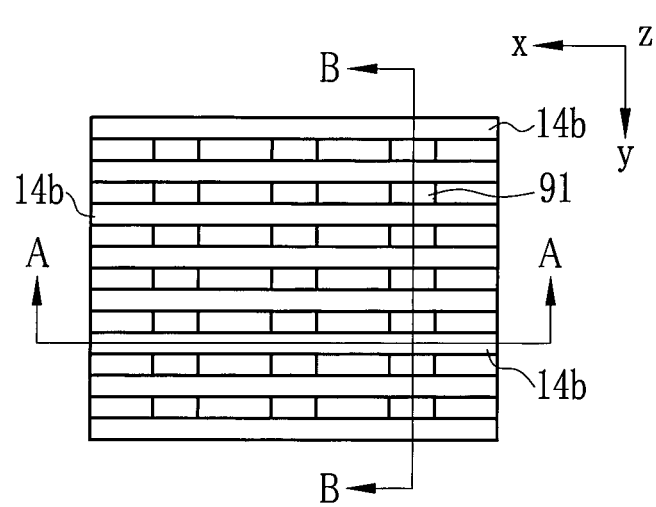
FIG. 27A is a plan view showing a seed layer provided with a plurality of linear concave portions in the $11^{th}$ embodiment.
Figure 27C:
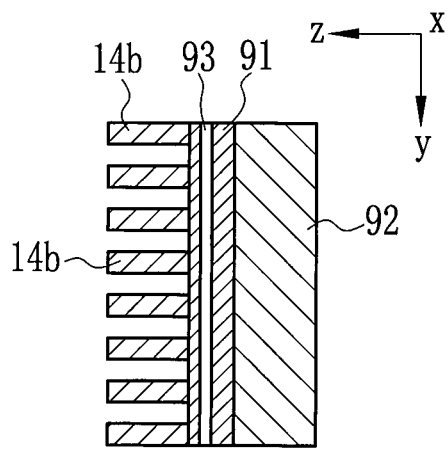
FIGS. 27B and 27C are cross-sectional views showing the seed layer provided with a plurality of linear concave portions in the $11^{th}$ embodiment.
Figure 27B:
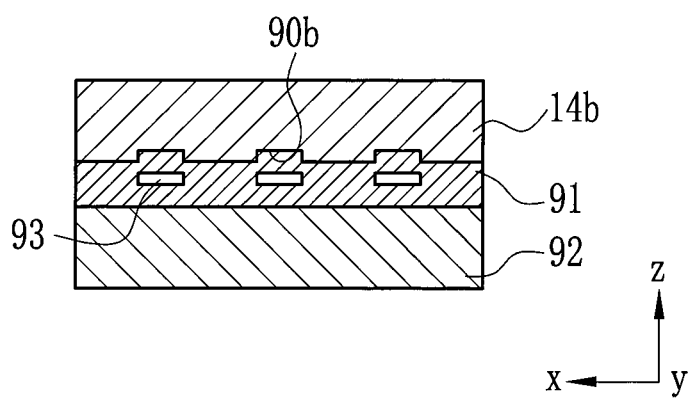

In this embodiment, the voids formed between the first and second conductive thin-layers 95 and 96 at the bonding of the etching substrate 90 and the support substrate 92 are dispersed and included in a plurality of the depression portions 93. Thereby, coming off of the etching substrate 90 and the distortion of the X-ray transmitting sections 14b caused by the voids are prevented, and bonding strength between the etching substrate 90 and the support substrate 92 increases. FIG. 27A is a plan view showing that the grooves 90a and the X-ray transmitting sections 14b are formed on the etching substrate 90. FIG. 27B is a cross-section taken along a line A-A in FIG. 27A. FIG. 27C is a cross-section taken along a line B-B in FIG. 27A. As shown in the above drawings, the seed layer 91 is embedded in the depression portions 90b provided on the X-ray transmitting section 14b. Thus, the seed layer 91 also functions as an anchor layer for preventing the X-ray absorbing sections 14a and the X-ray transmitting sections 14b from coming off from the seed layer 91.

Figure 28:
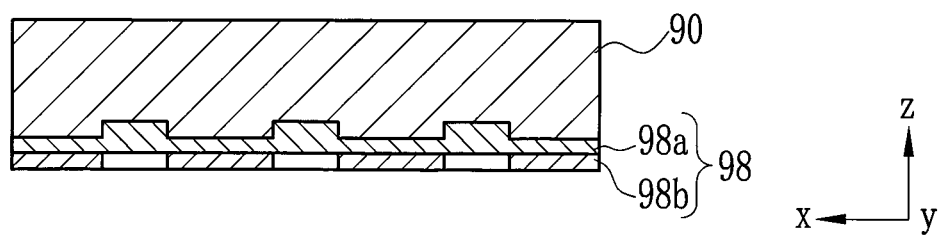
FIG. 28 is a cross-sectional view showing that the conductive thin-layer is composed of two layers in the $11^{th}$ embodiment.

When the seed layer 91 is made of the Au, the seed layer 91 may not have sufficient rigidity as the anchor layer for preventing the X-ray absorbing sections 14a and the X-ray transmitting sections 14b from coming off. In this case, as shown in FIG. 28, a first conductive thin-layer 98 formed on the etching substrate 90 may be composed of a first layer 98a with high rigidity such as Ni and a second layer 98b made of the Au to improve the anchor effect of the seed layer.

12th Embodiment

Figure 29:
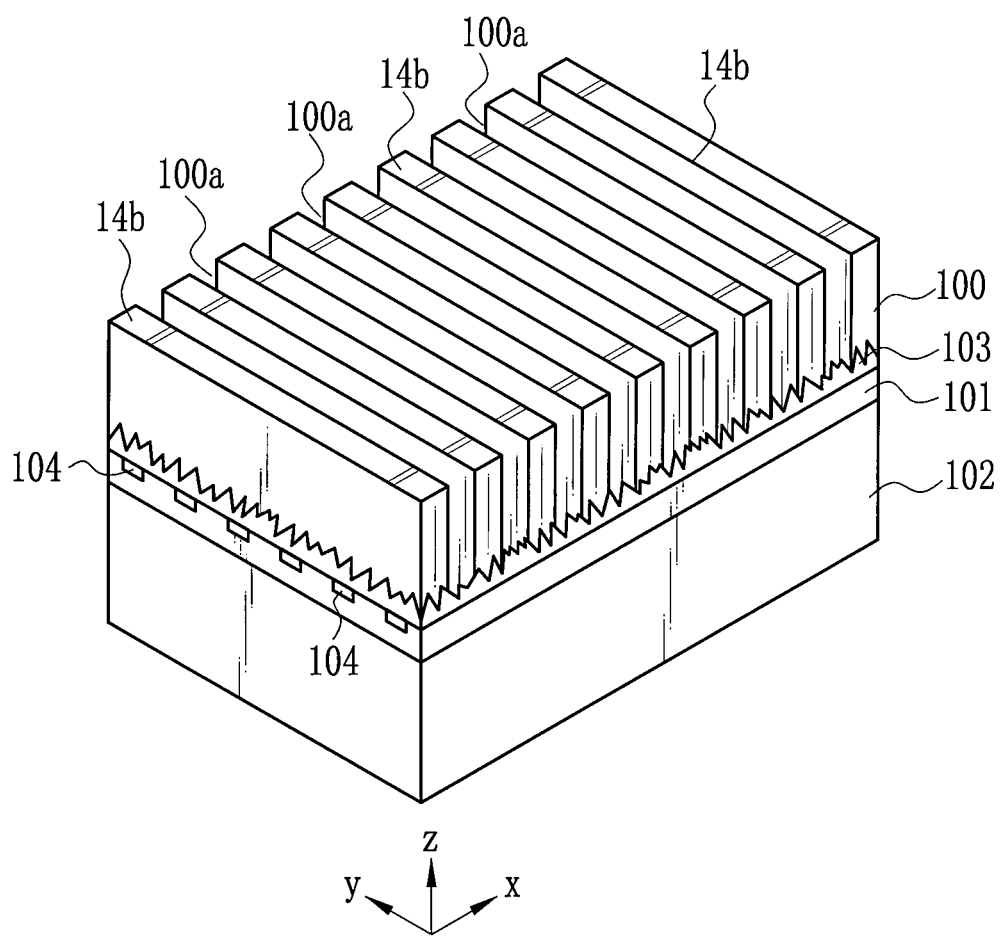
FIG. 29 is a perspective view showing an anchor layer for preventing coming off of the X-ray absorbing section and the X-ray transmitting section in a $12^{th}$ embodiment.

FIG. 29 shows a layer structure of an etching substrate 100, a seed layer 101 and a support substrate 102, and grooves 100a and the X-ray transmitting sections 14b are formed in the etching substrate 100. In this embodiment, instead of the seed layer 91 of the 10th embodiment, an anchor layer 103 with a rough surface is provided between the etching substrate 100 and the seed layer 101. The anchor layer 103 is provided entirely under the etching substrate 100. The rough surface is useful to increase bonding areas between the anchor layer 103 and the X-ray absorbing sections 14a and between the anchor layer 103 and the X-ray transmitting sections 14b. As a result, a higher anchor effect is provided as compared to the seed layer 91 of the 10th embodiment.

Figure 30A:
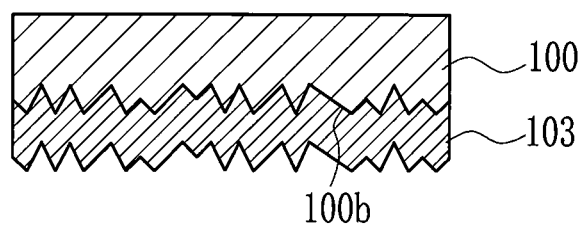
FIGS. 30A to 30D are cross-sectional views showing steps for producing a grid in the $12^{th}$ embodiment.

The anchor layer 103 is produced by the following steps. As shown in FIG. 30A, a rough surface 100b is formed on the bottom face of the etching substrate 100. The rough surface has projections and depressions with the height difference of the order of 0.1 μm to 10 μm. The anchor layer 103 is formed on the rough surface 100b using sputtering, plating, or the like. The anchor layer 103 is made of a conductive material that has low X-ray absorption properties and high rigidity, and is resistant to etching liquid and gas used for the dry etching of the etching substrate 100. The material of the anchor layer 103 is preferably, for example, Ni, stainless steel, or the like.

Figure 30B:
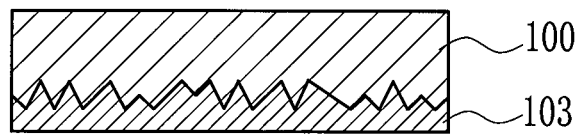
Figure 30C:
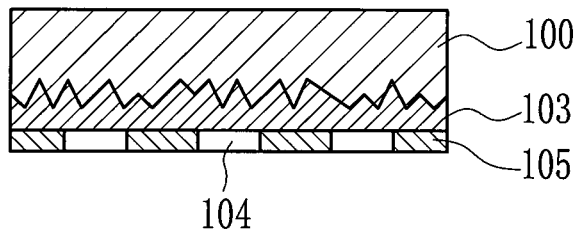
Figure 30D:
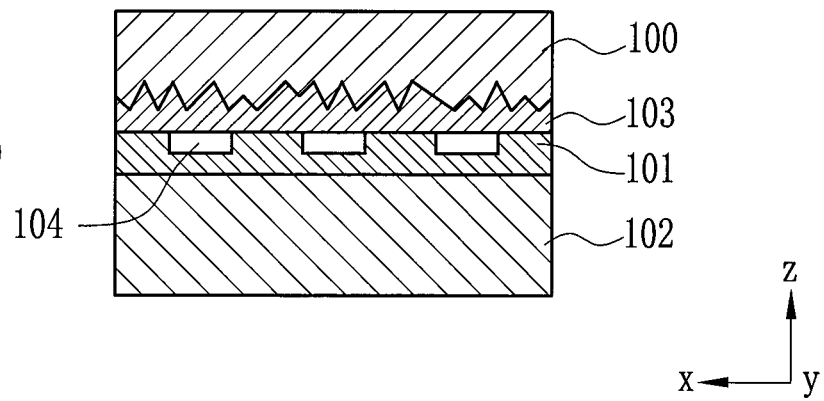

As shown in FIG. 30B, in a next step, the bottom face of the anchor layer 103 is polished using CMP or the like to be smoothed. As shown in FIG. 30C, in a next step, under the anchor layer 103, a first conductive thin-layer 105 with depression portions 104 is formed. As shown in FIG. 30D, in a next step, the etching substrate 100 and the support substrate 102 having the second conductive thin-layer are bonded together. Thus, the seed layer 101 is formed. Thereafter, as shown in FIG. 29, as with the above embodiments, the grooves 100a and the X-ray transmitting sections 14b are formed in the etching substrate 100. The grooves 100a are filled with the Au by electroplating. Thus, the X-ray absorbing sections 14a are formed. The anchor layer 103 and the seed layer 101 are used as the electrodes during the electroplating.

Figure 31:
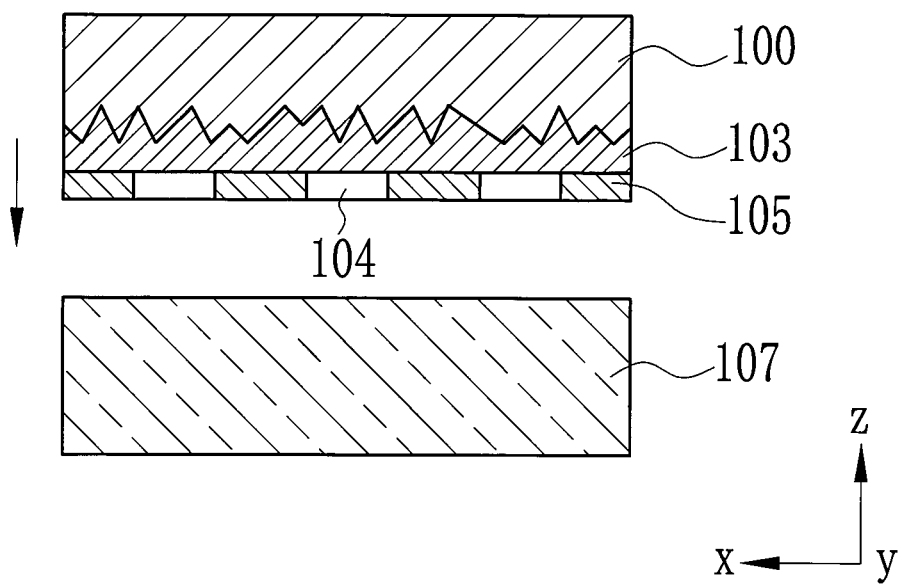
FIG. 31 is a cross-sectional view showing joining by anodization.

In the case where the diffusion bonding is used for bonding the etching substrate and the support substrate, a metal layer is required for each of bonding surfaces of the etching substrate and the support substrate. To perform anodic bonding, on the other hand, a metal layer is required only on one of the bonding surfaces. To perform the anodic bonding of the etching substrate and the support substrate, as shown in FIG. 31, the seed layer 101 may be provided only on the etching substrate 100 side. In the anodic bonding, however, the substrate to be bonded to the metal layer needs to contain Na, so it is preferable that the support substrate 107 is made of borosilicate glass such as TEMPAX glass or Pyrex glass. Alternatively, a support substrate 107 having a layer of borosilicate glass formed on the bonding surface may be used.

13th Embodiment

Figure 32A:
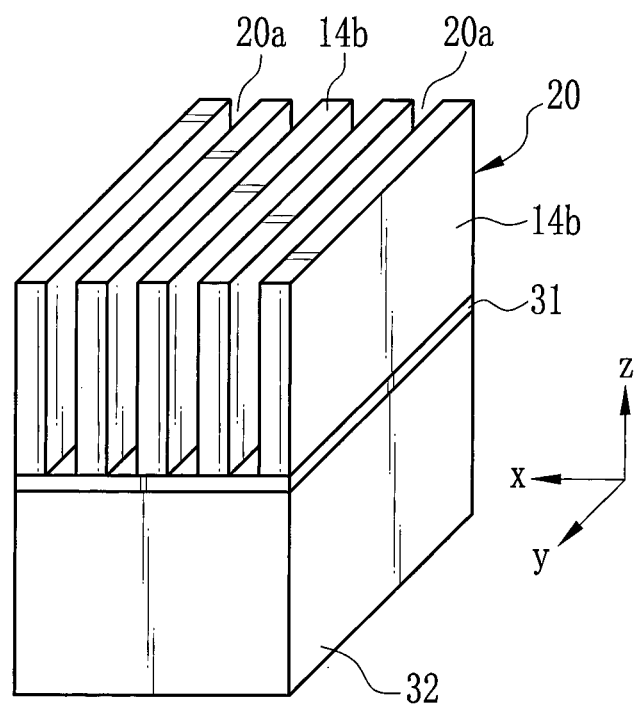
FIGS. 32A and 32B are perspective views showing the etching substrate after being etched.

FIG. 32A shows the etching substrate 20 formed with the grooves 20a and the X-ray transmitting sections 14b as in the second embodiment. The second grid has a microstructure with a high aspect ratio. The pitch between the X-ray transmitting sections 14b is several μm. The thickness of the X-ray transmitting section 14b in the X-ray traveling direction is several tens to a hundred and several tens of μm. After the grooves 20a are formed in the etching substrate 20, the etching substrate 20 has a plurality of plate-like X-ray transmitting sections 14b arranged in the x-direction.

Figure 32B:
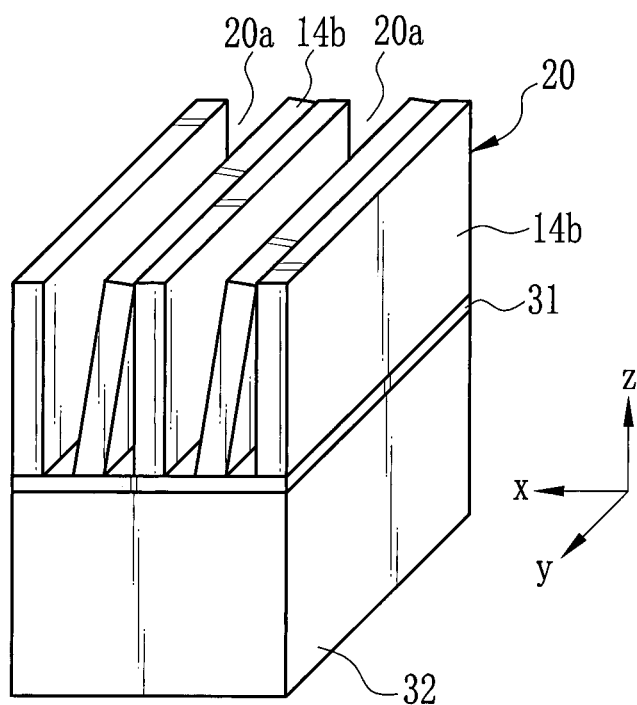

For example, when the grooves 20a are formed using the X-ray lithography, sticking is likely to occur as shown in FIG. 32B. The sticking refers to falling of the X-ray transmitting section 14b to come in contact with the adjacent X-ray transmitting section 14b due to the swinging or vibration of the solution during development, surface tension of water during drying, or the like. The sticking of the X-ray transmitting sections 14b may be caused by uneven plating growth. For example, when an area with high plating growth and an area with low plating growth are adjacent with each other, the area with the high plating growth makes the X-ray transmitting section 14b fall down. When the groove 20a is deformed, the pitches of the X-ray absorbing sections 14a and the X-ray transmitting sections 14b become nonuniform. As a result, the performance of the second grid is degraded.

Figure 33B:
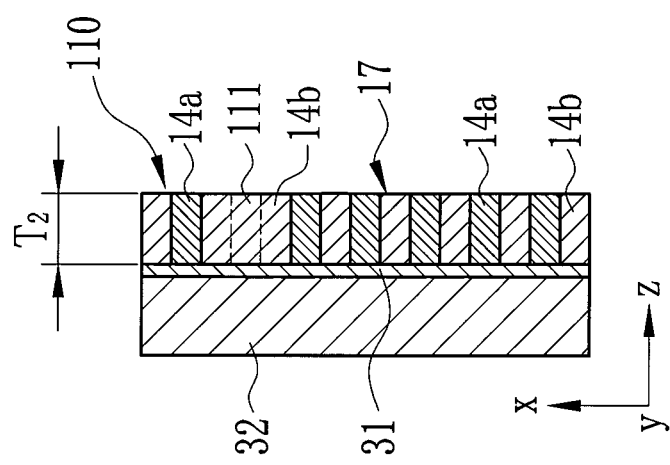
FIG. 33B is a cross-sectional view showing the second grid on which the transmitting-section bridge members are formed according to the 13th embodiment.
Figure 33A:
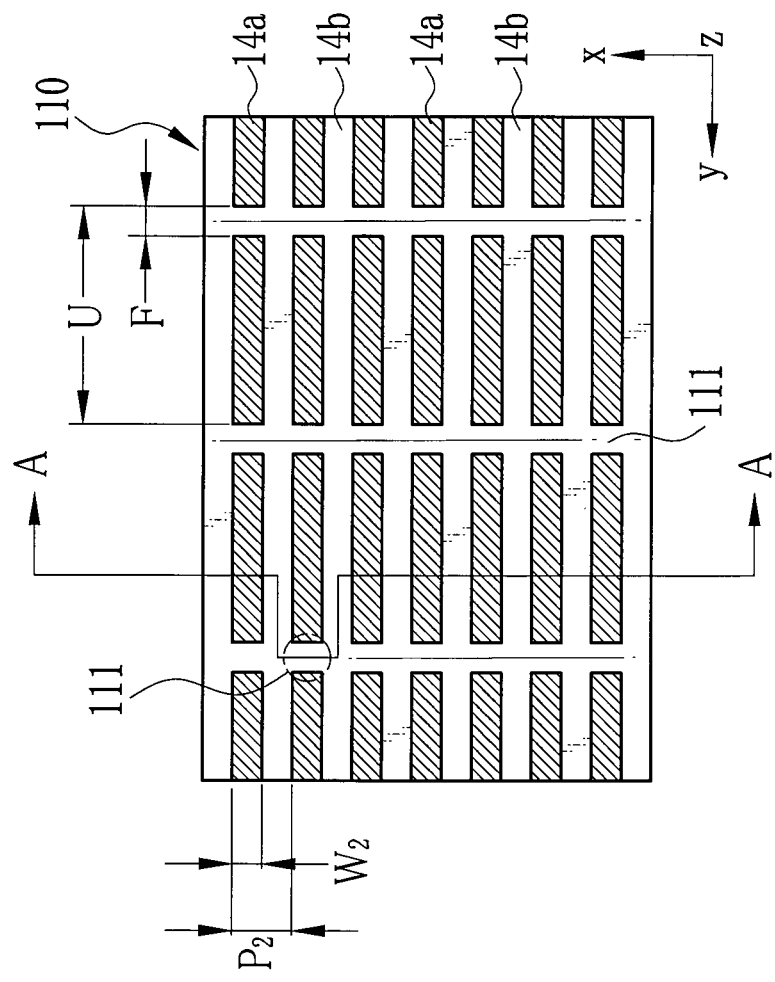
FIG. 33A is a plan view showing a second grid on which transmitting-section bridge members are formed according to a 13th Embodiment.

To solve the above problems, as shown in FIGS. 33A and 33B, a second grid 110 of the present invention is provided with a plurality of transmitting-section bridging portions 111 within or across the groove 20a for coupling the adjacent X-ray transmitting sections 14b. The transmitting-section bridging portion 111 is formed by the etching substrate 20, integrally with the X-ray transmitting section 14b. The transmitting-section bridging portion 111 is at the same height as the groove 20a so as to partition the X-ray absorbing section 14a. The transmitting-section bridging portion 111 maintains the spacing between the X-ray transmitting sections 14b. Thus, the strength of the second grid 110 is increased.

Figure 34:
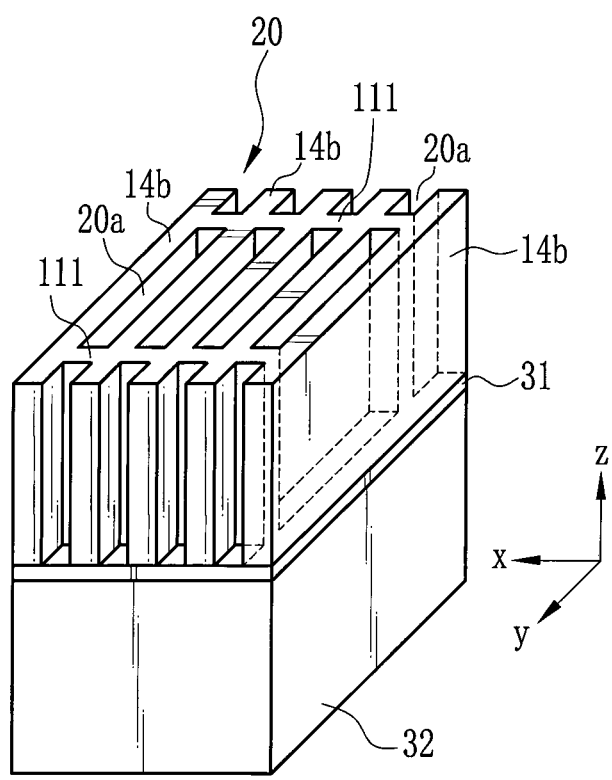
FIG. 34 is a perspective view showing an etching substrate of the 13th embodiment after being etched.

The transmitting-section bridging portion 111 is formed using the etch mask 25 as shown in FIG. 5D. In this case, the etch mask 25 has a pattern of the X-ray transmitting sections 14b together with a bridge pattern defining the shape of the transmitting-section bridging portions 111. The etching substrate 20 is etched through the etch mask 25. As shown in FIG. 34, on the etching substrate 20 after being etched, a plurality of the grooves 20a, a plurality of the X-ray transmitting sections 14b, and a plurality of the transmitting-section bridging portions 111 are formed integrally.

After the etching substrate 20 has been completely etched, as with the second embodiment, the groove 20a is filled with the Au 27 using electroplating. Thus, the second grid 110 shown in FIG. 33A is formed. The X-ray transmitting sections 14b are coupled to each other by the transmitting-section bridging portion 111. This prevents the X-ray transmitting sections 14b from sticking to each other during the electroplating.

It is preferable that a width F of the transmitting-section bridging portion 111 and a width W2 of the groove 20a satisfy F≥W2. When a pitch U between the transmitting-section bridging portions 111 in the y direction is too small, the number of the transmitting-section bridging portions 111 increases, which reduces the X-ray absorption properties of the X-ray absorbing sections 14a. It is preferable that the pitch U between the transmitting-section bridging portions 111 is, for example, five or more times as wide as the width W2 of the groove 20a.

14th Embodiment

Figure 35B:
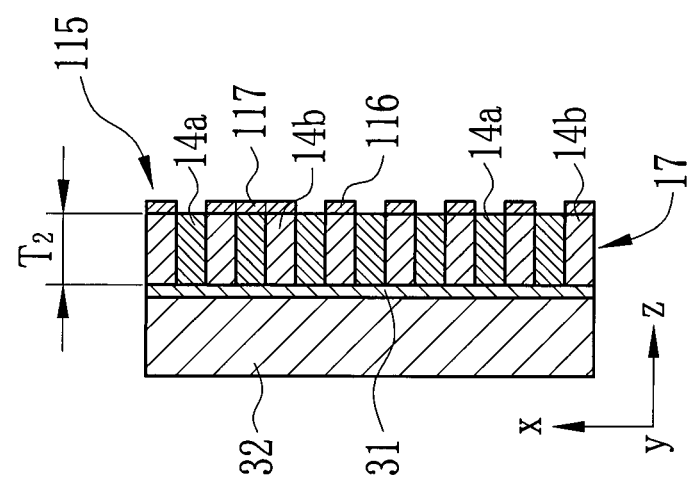
FIG. 35B is a cross-sectional view showing the second grid on which the transmitting-section bridge members are formed according to the 14th embodiment.
Figure 35A:
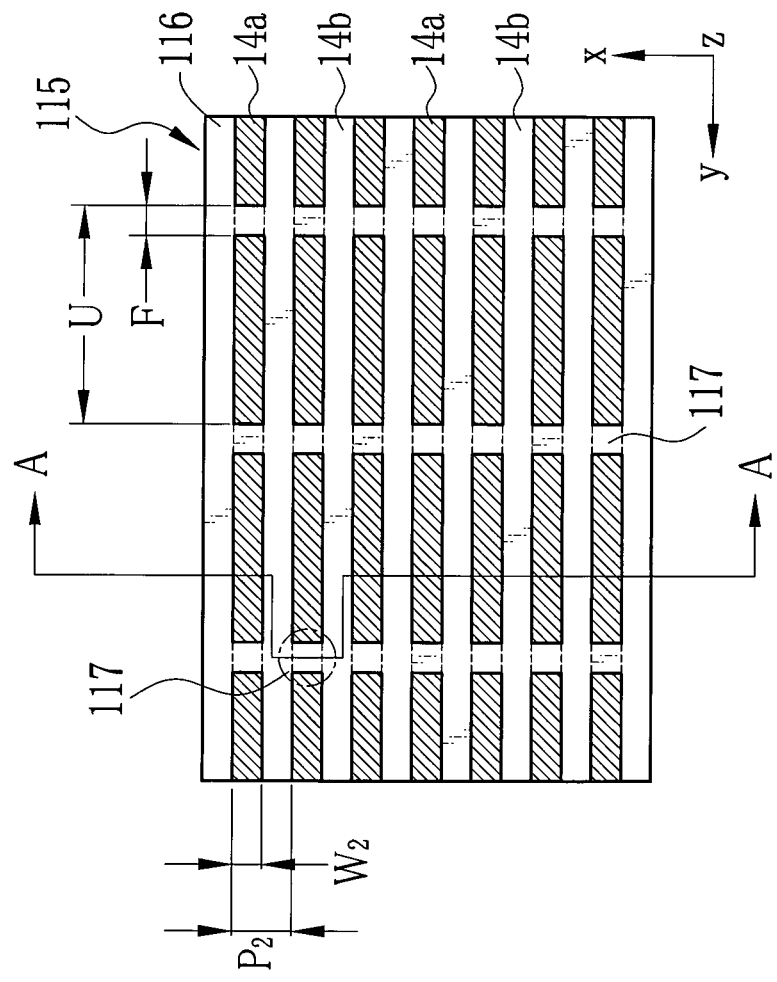
FIG. 35A is a plan view showing a second grid on which transmitting-section bridge members are formed according to a 14th Embodiment.

In the 13th embodiment, the transmitting-section bridging portion 111 has the same height as the groove 20a. Alternatively, the transmitting-section bridging portion 111 may be provided only to the top portion or on the opening side of the groove 20a. As shown in FIG. 35, a second grid 115 of this embodiment is provided with an etch mask 116 on each of the X-ray transmitting sections 14b. The etch mask 116 is used for etching the etching substrate 20. On the etch mask 116, bridge patterns 117 that become the transmitting-section bridging portions for coupling the adjacent X-ray transmitting sections 14b are formed integrally. The width F of each bridge pattern 117 and the pitch U between the bridge patterns 117 are same as those in the 13th embodiment. The bridge pattern 117 maintains the spacing between the X-ray transmitting sections 14b. Thus, the strength of the second grid 115 is increased.

A method for forming the bridge pattern 117 is described. As shown in FIG. 36, after the support substrate 32 and the etching substrate 20 are bonded together, liquid resist is applied to the etching substrate 20 and then exposed and developed. Thus, the etch mask 116 is formed. On the etch mask 116, a plurality of line patterns 118 extending in the y direction and arranged in the x direction and a plurality of bridge patterns 117 each provided between the line patterns 118 to couple the line patterns 118 are provided. FIG. 36 shows a minimum configuration of the etch mask 116. Actually, the etch mask 116 is provided with a plurality of the bridge patterns 117 and a plurality of the line patterns 118.

FIGS. 37A and 37C shown on the left-sides are the cross-sections taken along a line A-A in FIG. 36, and FIGS. 37B and 37D shown on the right sides are the cross-sections taken along a line B-B in FIG. 36. In FIGS. 37A and 37B, the cross-sections taken along the lines A-A and B-B after the etch mask 116 has been formed are shown. In the next step, as shown in FIGS. 37C and 37D, the etching substrate 20 is etched through the etch mask 116 using the Bosch process or the cryo process. Thus, a plurality of the grooves 20a and a plurality of the X-ray transmitting sections 14b both arranged in the x direction are formed.

Figure 38:
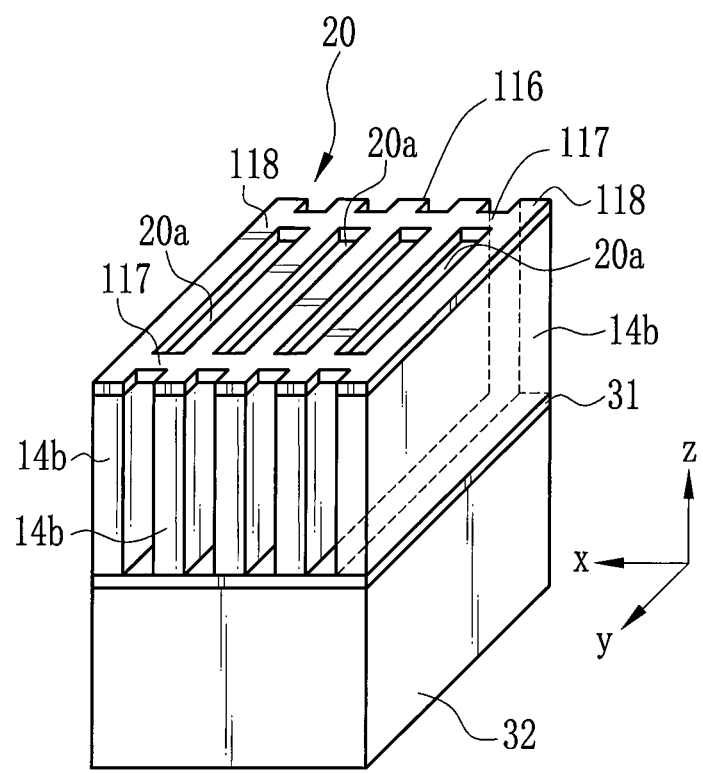
FIG. 38 is a perspective view showing the etching substrate of the 14th embodiment after being etched.

The Bosch process or the cryo process forms a highly vertical shape, but a certain degree of side etching occurs. For example, when the etching substrate 20 is etched 100 μm in depth, a side etching of the order of 0.5 μm occurs. Accordingly, silicon under the bridge pattern 117 is removed by appropriately setting the width F of the bridge pattern 117 in the y direction. As shown in FIG. 38, the etching substrate 20 after being etched is formed with a plurality of the grooves 20a and a plurality of the X-ray transmitting sections 14b integrally. The adjacent X-ray transmitting sections 14b are coupled to each other by the bridge patterns 117 from above.

After the etching of the etching substrate 20 has been completed, as with the first embodiment, the grooves 20a are filled with the Au 27 by the electroplating. Thus, the second grid 115 shown in FIG. 35 is formed. The X-ray transmitting sections 14b are coupled to each other by bridge patterns 117. This prevents the X-ray transmitting sections 14b from sticking to each other during the electroplating.

15th Embodiment

Figure 39:
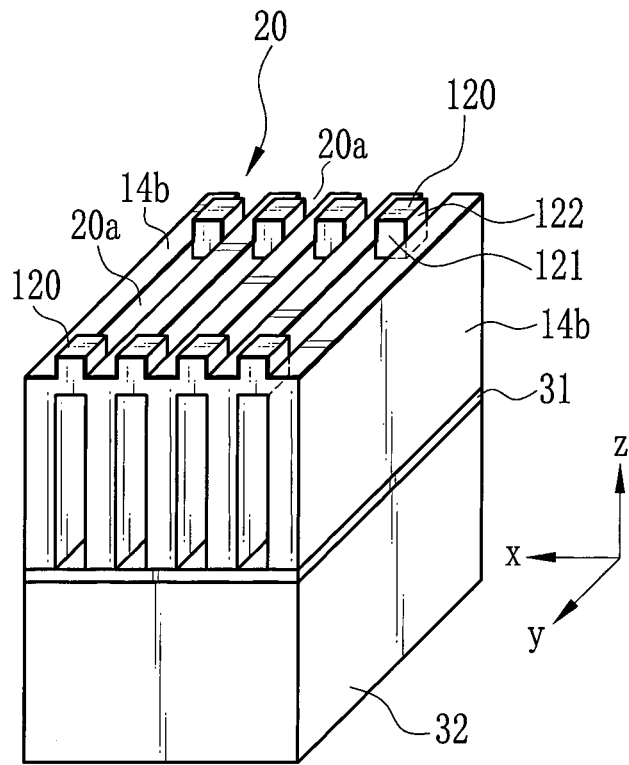
FIG. 39 is a perspective view showing an etching substrate of a 15th embodiment after being etched.

In the 14th embodiment, the X-ray transmitting sections 14b are coupled to each other using bridge patterns 117 of the etch mask 116. The resist of the etch mask, however, may be insufficient in strength. A transmitting-section bridging portion composed of the etching substrate and the etch mask may be provided. As shown in FIG. 39, a transmitting-section bridging portion 120 of this embodiment includes a coupling portion 121 formed integrally with the X-ray transmitting section 11b and a bridge pattern 122 that is a reinforcement member provided above the coupling portion 121.

Figure 40:
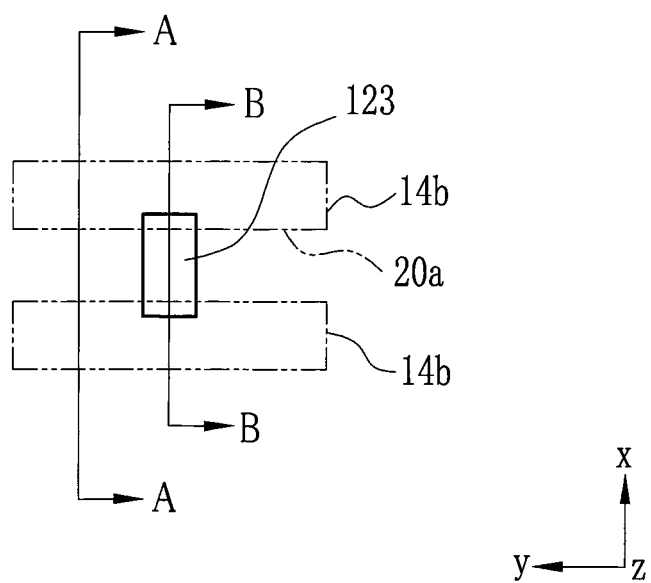
FIG. 40 is a plan view showing a bridge mask used for producing a transmitting-section bridge member of the 15th embodiment.

Hereinafter, a method for forming the transmitting-section bridging portion 120 is described. As shown in FIG. 40, on the etching substrate 20 after being bonded to the support substrate 32, a plurality of belt-like bridge masks 123 extending in the x direction and arranged in the y direction are formed by the application of liquid resist, exposure, development, and the like. The bridge mask 123 is arranged to couple the X-ray transmitting sections 14b across the groove 20a, shown in two-dot chain lines, formed on the etching substrate 20 by etching. FIG. 40 shows only one bridge mask 123. Actually, a number of bridge masks 123 are formed on the etching substrate 20.

Figure 41A:
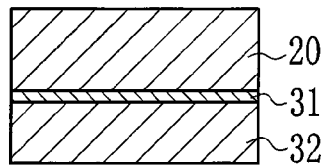
FIGS. 41A to 41J are cross-sectional views showing steps for producing a transmitting-section bridge member of the 15th embodiment.
Figure 41B:
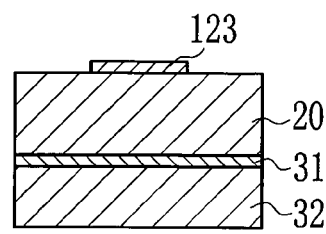
Figure 41C:
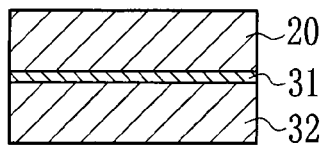
Figure 41D:
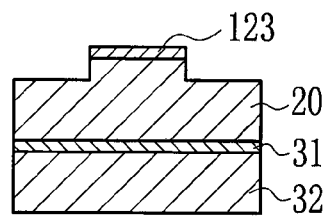

Of FIGS. 41A to 41J, those shown on the left side are the cross-sections taken along a line A-A on FIG. 40 and those shown on the right side are the cross-sections taken along a line B-B. FIGS. 41A and 41B show the cross-sections taken along the lines A-A and B-B after the bridge mask 123 is formed. As shown in FIGS. 41C and 41D, in a next step, the etching substrate 20 is etched halfway in the thickness direction by the Bosch process through the bridge mask 123.

Figure 41E:
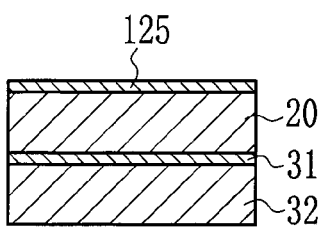
Figure 41F:
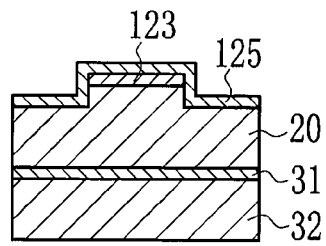
Figure 41G:
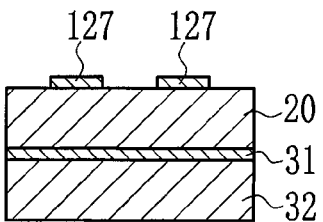
Figure 41H:
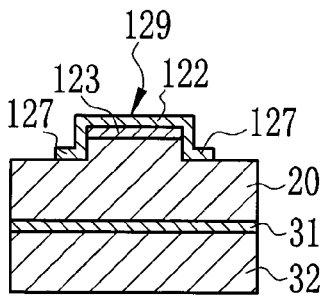
Figure 42:
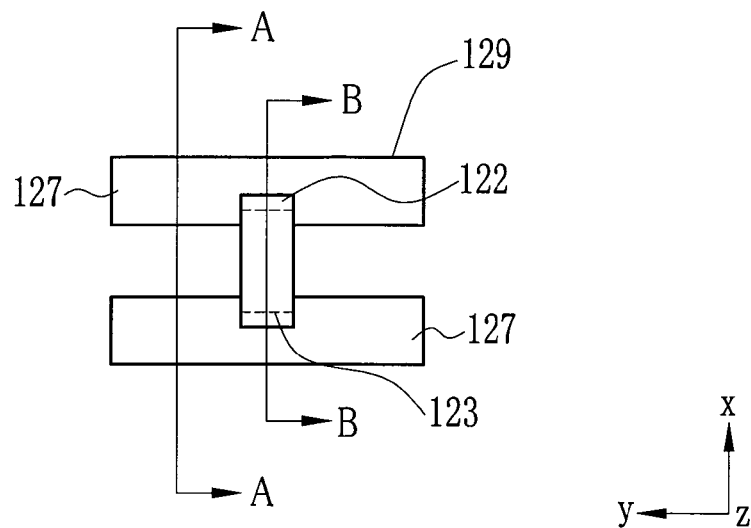
FIG. 42 is a plan view showing an etch mask used for producing the transmitting-section bridge member of the 15th embodiment.

Then, as shown in FIGS. 41E and 41F, an insulating layer 125 of $SiO_2$ or the like is formed on the etching substrate 20 using the vapor deposition or the like. As shown in FIGS. 41G and 41H, the insulating layer 125 is etched using an etch mask (not shown). Thereby, as shown in FIG. 42, on the etching substrate 20, an etch mask 129 composed of a plurality of line patterns 127 and a plurality of the bridge patterns 122 is formed. The line patterns 127 extend in the x direction and are arranged in the y direction. Each bridge pattern 122 couples the line patterns 127 and covers the bridge mask 123.

Figure 41I:
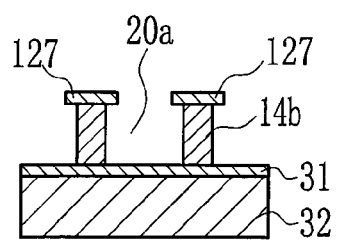
Figure 41J:
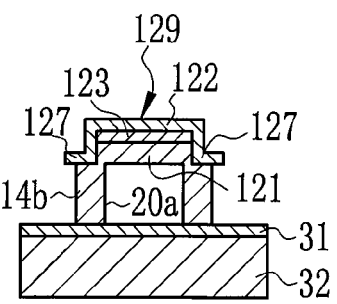

As shown in FIGS. 41I and 41J, the etching substrate 20 is etched by the Bosch process through the etch mask 129. Thereby, a plurality of the grooves 20a and a plurality of the X-ray transmitting sections 14b, both arranged in the y direction, are formed. Because the bridge mask 123 and the line pattern 127 overlap with each other, the side etching in the overlapped portion is suppressed. The silicon under the bridge mask 123 remains unremoved and functions as the coupling portion 121 for coupling the X-ray transmitting sections 14b. Thus, the coupling portion 121, the bridge pattern 122 for reinforcing the coupling portion 121, and the bridge mask 123 function as the transmitting-section bridging portion 120 for coupling the X-ray transmitting sections 14b.

16th Embodiment

Figure 43:
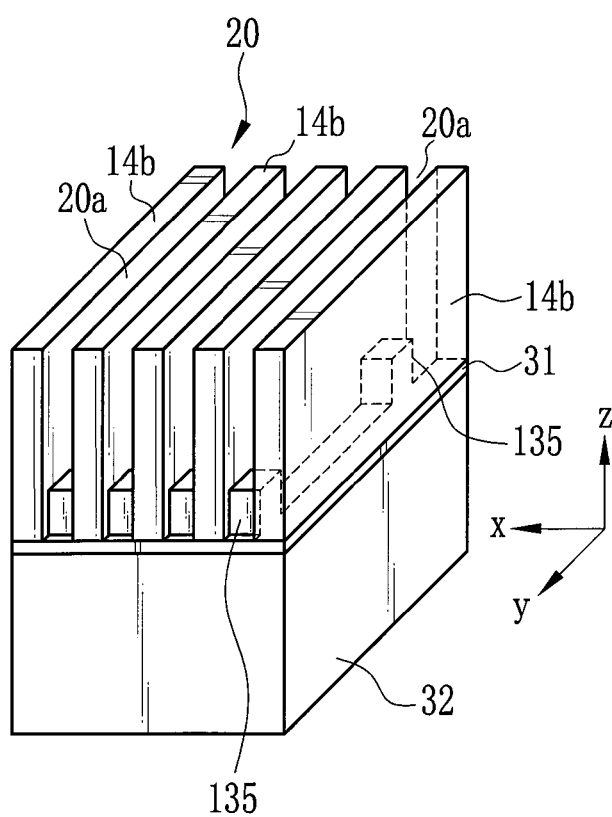
FIG. 43 is a perspective view showing the etching substrate of a 16th embodiment after being etched.

In the 13$^{th}$ and 14$^{th}$ embodiments, transmitting-section bridging portions are provided on the opening sides of the grooves 20a. As shown in FIG. 43, transmitting-section bridging portions 135 may be disposed on the bottom of the grooves 20a.

Figure 44:
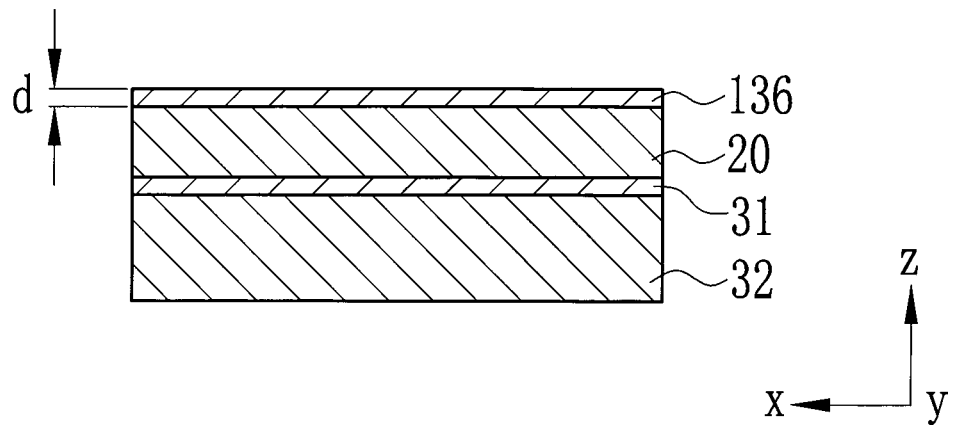
FIG. 44 is a cross-sectional view showing that an insulating layer is formed on the etching substrate in the 16th embodiment.
Figure 45:
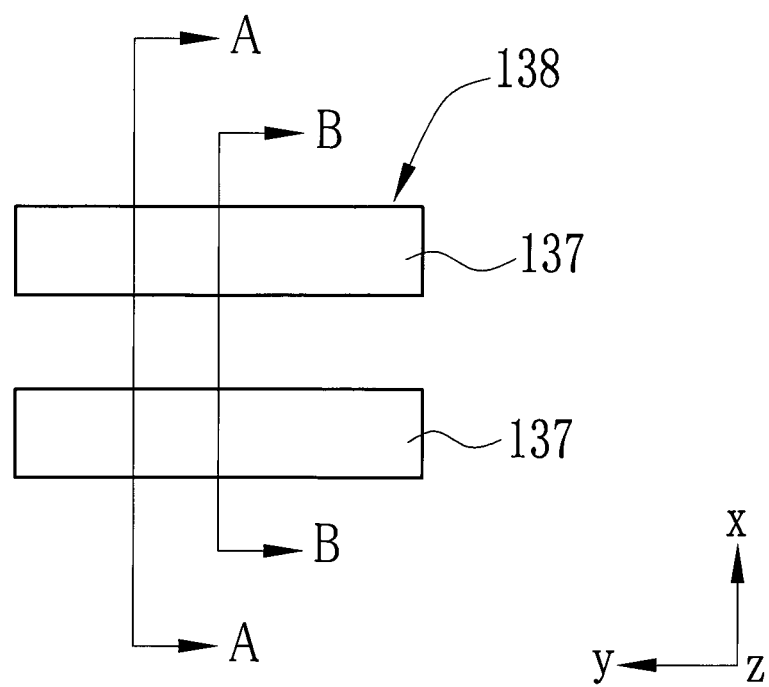
FIG. 45 is a plan view showing a first etch mask used in the 16th embodiment.

Hereinafter, a method for forming the transmitting-section bridging portions 135 is described. As shown in FIG. 44, in this embodiment, a first insulating layer 136 of $SiO_2$ or the like is formed with the width "d" using the vapor deposition or the like on the top face of the etching substrate 20 after the support substrate 32 is bonded thereto. Next, as shown in FIG. 45, a first etch mask 138 is formed on the first insulating layer 136 by application of liquid resist, exposure, and development. The first etch mask 138 has a plurality of line patterns 137 extending in the y direction and arranged in the x direction.

Figure 46A:
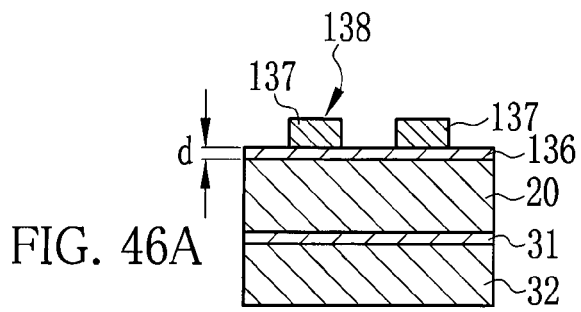
FIGS. 46A to 46H are explanatory views showing the first half of steps for forming a groove and a transmitting-section bridge member according to a 16th embodiment.
Figure 46B:
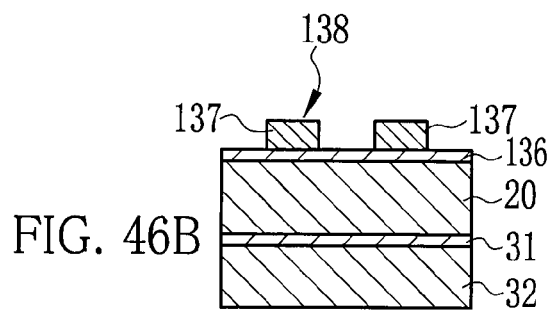

Of FIGS. 46A to 46H, those shown on the left side are the cross-sections taken along a line A-A in FIG. 45, and those shown on the right side are the cross-sections taken along a line B-B in FIG. 45. FIGS. 46A and 46B show the cross-sections taken along the lines A-A and B-B, respectively, after the first etch mask 138 is formed. The cross-section taken along the line B-B is in a position on which the above transmitting-section bridging portion 135 is formed. The cross-section taken along the line A-A is in a position on which the transmitting-section bridging portion 135 is not provided.

Figure 46C:
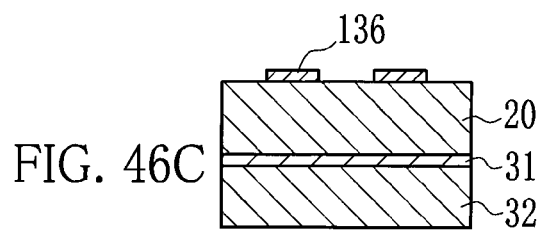
Figure 46D:
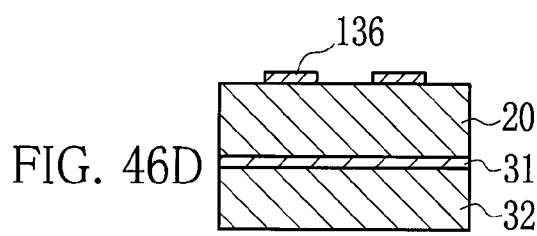
Figure 46E:
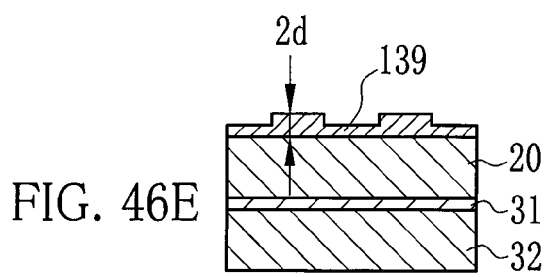
Figure 46F:
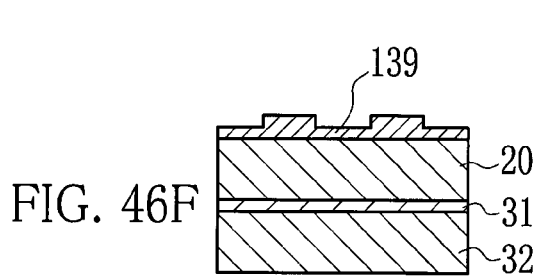

As shown in FIGS. 46C and 46D, in a next step, the first insulating layers 136 are etched through the first etch mask 138. Thereby, a line pattern composed of the first insulating layers 136 is formed. The first etch mask 138 is removed after the etching of the first insulating layer 136. Then, as shown in FIGS. 46E and 46F, in the same manner as the first insulating layer 136, a second insulating layer 139 with the width "d" is formed on the first insulating layer 136 after being etched and the etching substrate 20. Thus, the total thickness of the first and second insulating layers 136 and 139 becomes "2d". Alternatively, the thickness of the first insulating layer 136 may be set to "2d", and perform half etching, namely, the etching is stopped when the thickness of the first insulating layer 136 is reduced to half ("d").

Figure 46G:
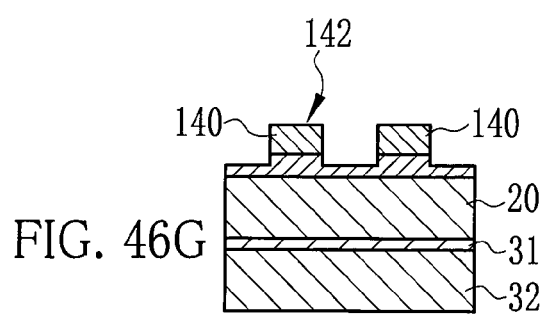
Figure 46H:
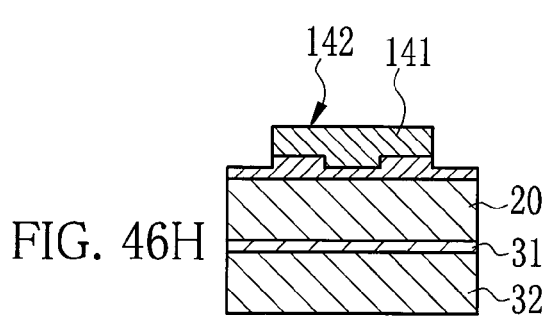
Figure 48:
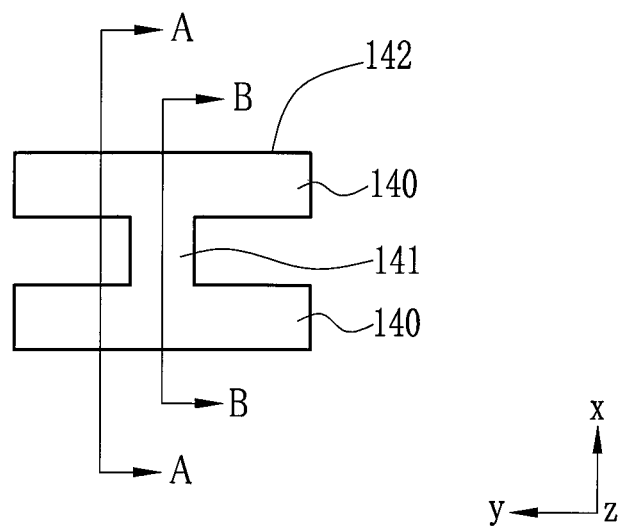
FIG. 48 is a plan view showing a second etch mask used in the 16th embodiment.

As shown in FIGS. 46G, 46H, and 48, in a next step, on the second insulating layer 139, a second etch mask 142 having line patterns 140 and bridge patterns 141 are formed in the same manner as the first etch mask 138. The line pattern 140 has the same or similar pattern to the first etch mask 138. The bridge pattern 141 couples the line patterns 140 in a position along the line B-B.

Figure 47A:
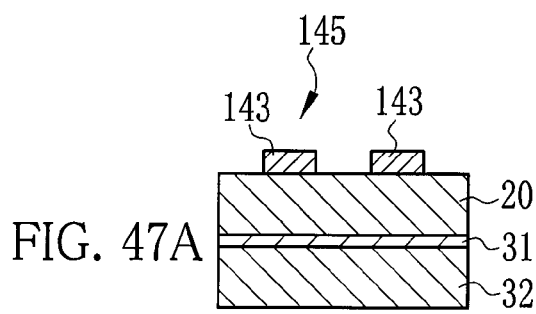
FIGS. 47A to 47F are explanatory views showing the second half of the steps for forming a groove and a transmitting-section bridge member.
Figure 47B:
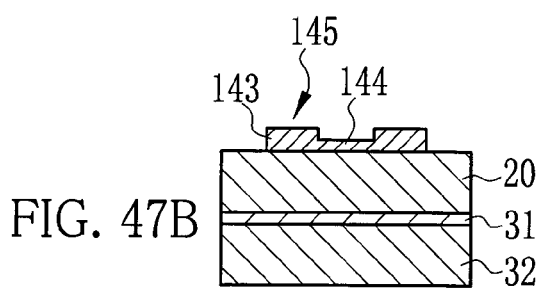
Figure 47C:
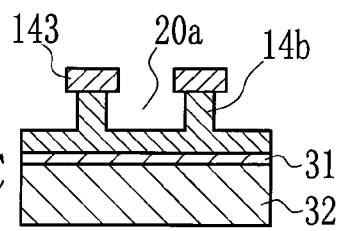
Figure 47D:
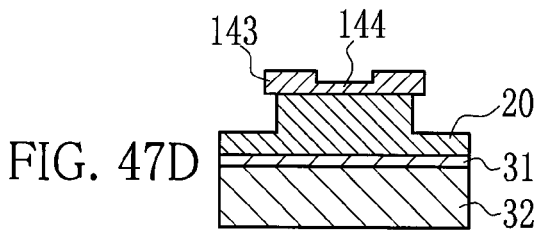
Figure 47E:
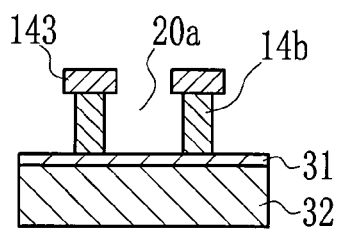
Figure 47F:
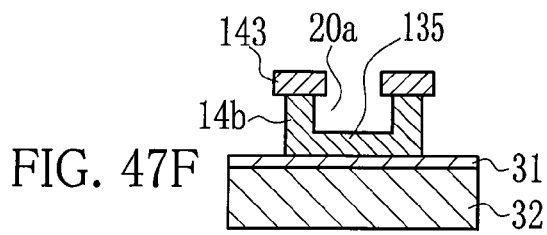

As shown in FIGS. 47A and 47B, in a next step, the second insulating layer 139 is etched through the second etch mask 142. Thereby, on the top face of the etching substrate 20, a third etch mask 145 composed of line patterns 143 and bridge patterns 144 is formed. The line pattern 143 has the first insulating layer 136 and the second insulating layer 139 formed on the first insulating layer 136. The bridge pattern 144 is composed of the second insulating layer 139. The second etch mask 142 is removed after the third etch mask 145 is formed.

As shown in FIGS. 47C to 47F, in a next step, the etching substrate 20 is etched using the Bosch process through the third etch mask 145. In this etching, in addition to the etching substrate 20, the third etch mask 145 is etched or thinned to a certain extent. Using a difference between the etching rates due to the difference between the thicknesses of the line pattern 143 and the bridge pattern 144, the bridge pattern 144 is completely removed earlier than the line pattern 143 to form the transmitting-section bridging portion 135 under the bridge pattern 144.

Conditions for completely removing the bridge pattern 144 when the etch substrate 20 is etched by a predetermined depth is represented by a mathematical expression "d=B×t/A", where "A" denotes a selection ratio between the silicon as the material of the etching substrate 20 and $SiO_2$ as the material of the third etch mask 145, and "t" denotes a depth of the silicon to be etched, and "B" denotes an etching ratio of the $SiO_2$ when the silicon is etched by the depth t, and "d" denotes the thickness of the bridge pattern 144.

For example, the thickness "d" of the bridge pattern 144 is d=30 nm where the selection ratio A=1000, the depth t=100 μm, and the etching ratio B=0.3. With this setting, when the etching substrate 20 is etched to the depth of 30 μm, the bridge pattern 144 disappears, and the etching of the silicon under the bridge pattern 144 is started. As a result, the transmitting-section bridging portion 135 of 30 μm in height is formed in the groove 20a.

17$^{th}$ Embodiment

Figure 49:
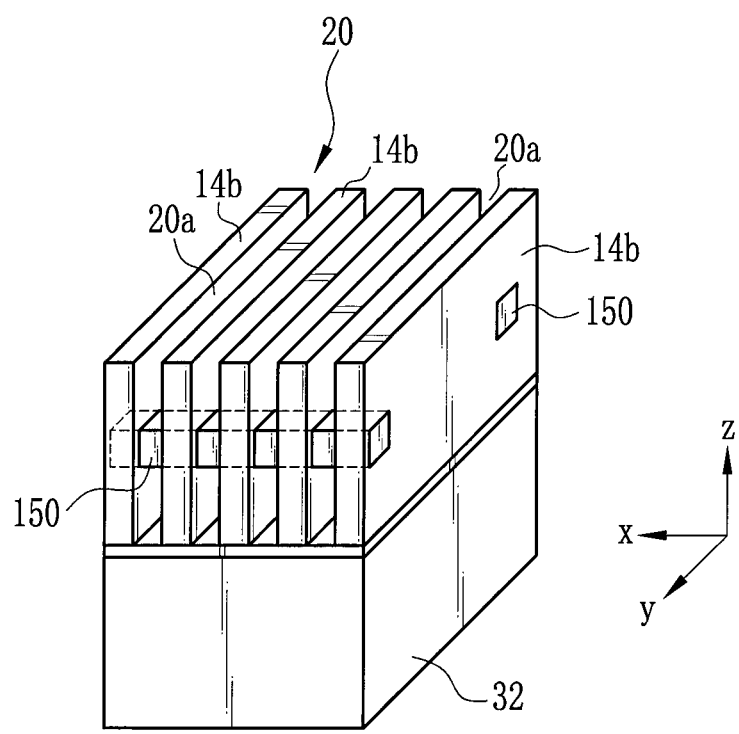
FIG. 49 is a perspective view showing the etching substrate 20 with transmitting-section bridge members formed in middle portions of the grooves according to a 17th embodiment.

En the 16$^{th}$ embodiment, the transmitting-section bridging portions 135 are provided at the bottom portion of the grooves 20a. As shown in FIG. 49, transmitting-section bridging portions 150 may be provided in the middle of the grooves 20a.

Figure 50:
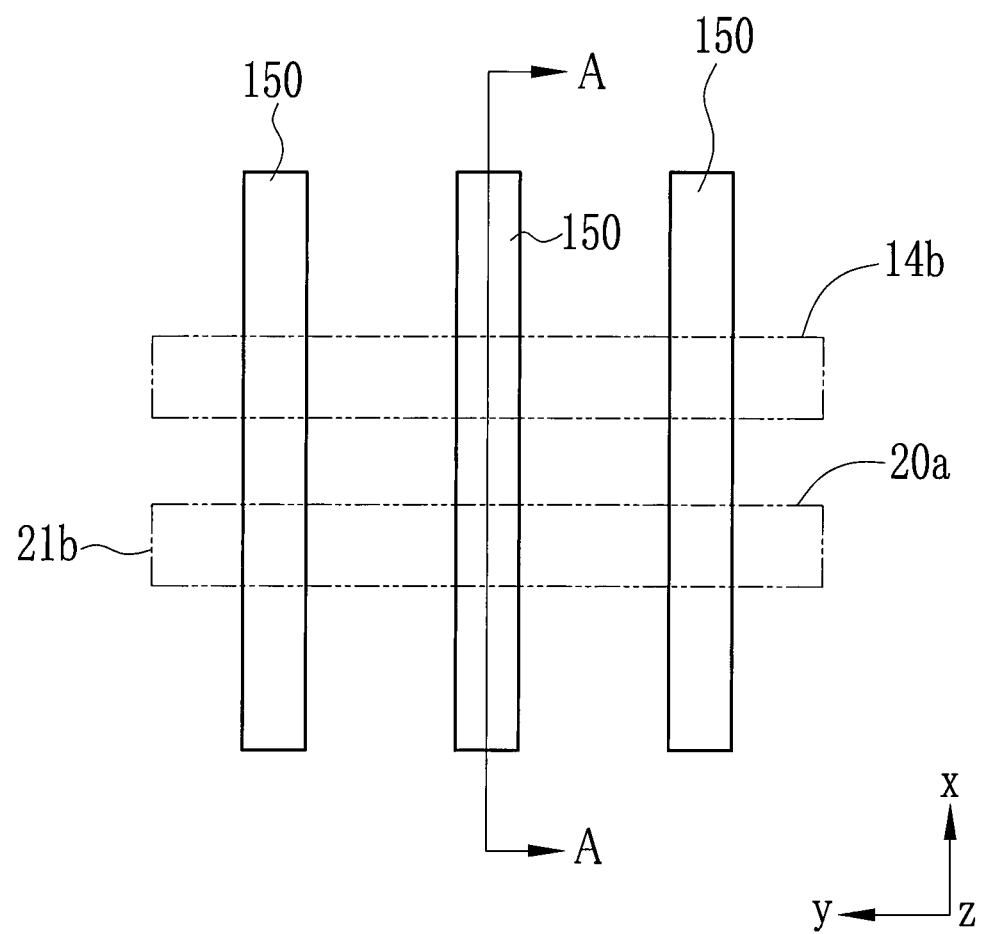
FIG. 50 is a plan view showing the transmitting-section bridge members formed on the etching substrate in the 17th embodiment.

Hereinafter, a method for forming the transmitting-section bridging portions 150 is described. As shown in FIG. 50, in this embodiment, on the top face of the etching substrate 20, a plurality of the transmitting-section bridging portions 150 are made of the $SiC_2$. The transmitting-section bridging portions 150 extend in the x direction and are arranged in the y direction. To form the transmitting-section bridging portions 150, for example, an $SiO_2$ layer is formed on the top face of the etching substrate 20, and then the $SiO_2$ layer is etched through the etch mask having the same shape pattern as the transmitting-section bridging portions 150. Two-dot chain lines denote the groove 20a and the X-ray transmitting section 14b formed on the etching substrate 20. The transmitting-section bridging portions 150 are formed through the grooves 20a and the X-ray transmitting sections 14b.

Figure 51A:
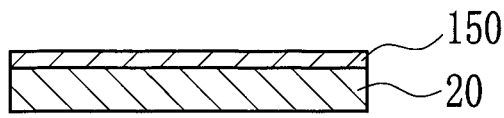
FIGS. 51A to 51E are explanatory views showing steps for forming the groove and the transmitting-section bridge member according to the 17th embodiment.
Figure 51B:
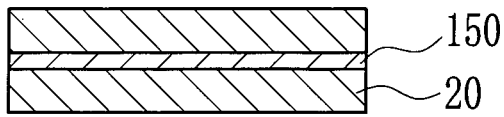
Figure 51C:
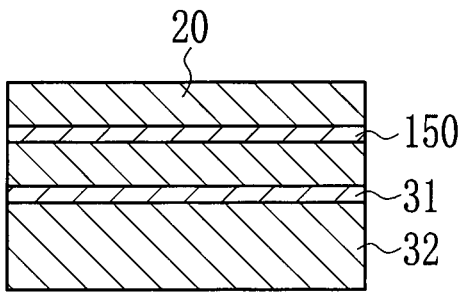

FIGS. 51A to 51E show cross-sections taken along a line A-A in FIG. 50. FIG. 51A shows the cross-section taken along the line A-A after the transmitting-section bridging portion 150 is formed. As shown in FIG. 51B, in a next step, the transmitting-section bridging portion 150 is embedded in the etching substrate 20 using a layer growing process (for example, CVD), or bonding and polishing of the silicon substrates. As shown in FIG. 51C, in a next step, the support substrate 32 is bonded to the bottom face of the etching substrate 20.

Figure 51D:
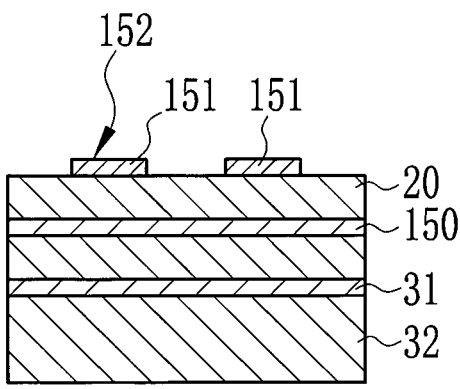
Figure 51E:
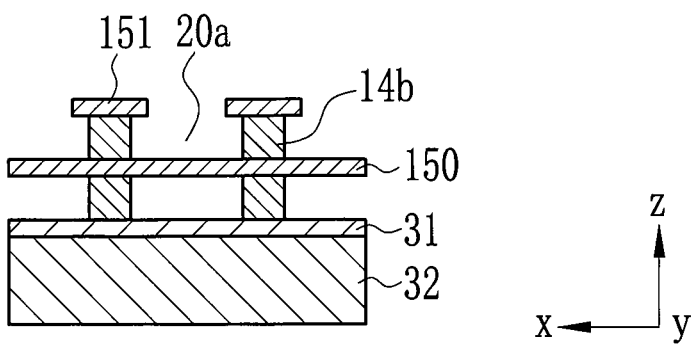
Figure 52:
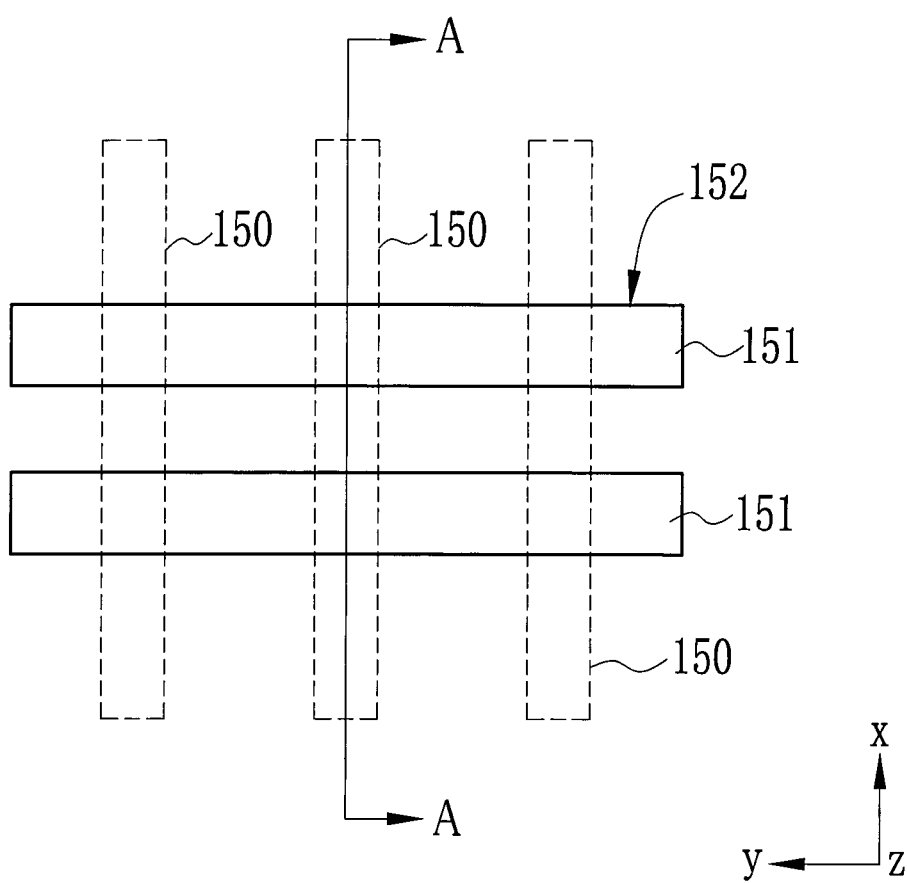
FIG. 52 is a plan view showing an etch mask used in the 17th Embodiment.

As shown in FIGS. 51D and 52, in a next step, on the top face of the etching substrate 20, an etch mask 152 is formed by the application of the liquid resist, exposure, and development, and the like. The etch mask 152 has a plurality of line patterns extending in the y direction and arranged in the x direction. Next, as shown in FIG. 51E, the etching substrate 20 is etched by the Bosch process through the etch mask 152. Thus, a plurality of the grooves 20a and a plurality of the X-ray transmitting sections 14b arranged in the x direction are formed.

As with the 16$^{th}$ embodiment, the silicon under the transmitting-section bridging portions 150 is removed using the side etching. Thereby, the transmitting-section bridging portions 150 are arranged through the X-ray transmitting sections 14b. A width of the transmitting-section bridging portion 150 is preferably, for example, 0.8 μm where the side etching is 0.5 μm.

The transmitting-section bridging portion 150 remains without being removed by the etching of the etching substrate 20. For example, when the selection ratio between the silicon as the material of the etching substrate 20 and the $SiO_2$ as the material of the transmitting-section bridging portion 150 is 1000, setting the thickness of the transmitting-section bridging portion 150 equal to or larger than 100 nm prevents the removal of the transmitting-section bridging portion 150 even if the etching substrate 20 is etched to the depth of 100 μm.

18$^{th}$ Embodiment

Figure 53A:
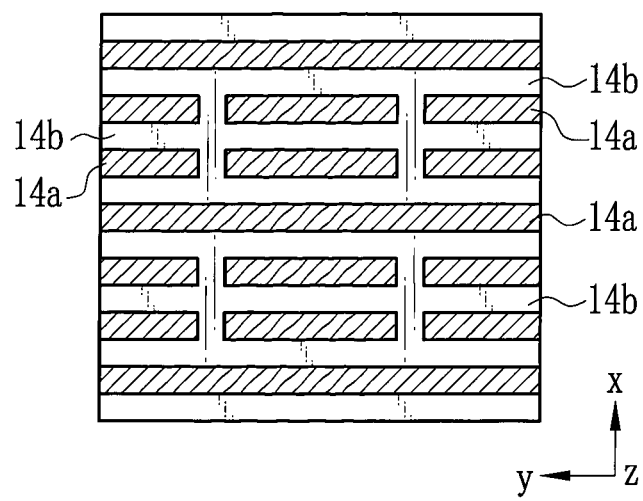
FIGS. 53A and 53B are plan views showing transmitting-section bridge members each coupling several X-ray transmitting sections in an 18th embodiment.
Figure 53B:
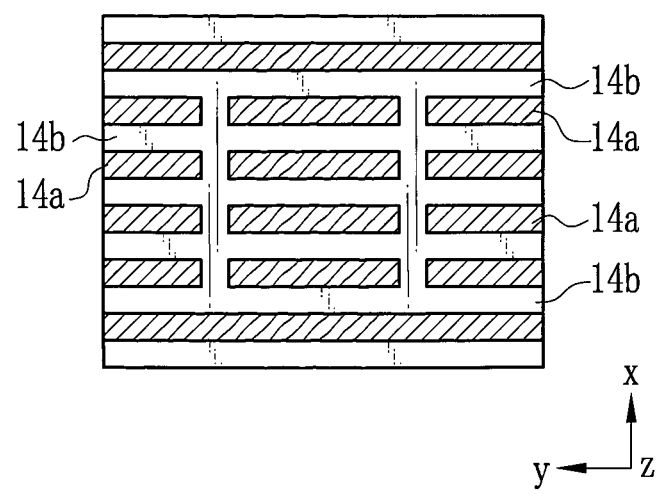

In each of the above embodiments, all the X-ray transmitting sections 14b are coupled using the transmitting-section bridging portions. Alternatively, each transmitting-section bridging portion may couple several X-ray transmitting sections 14b in the x direction. For example, in the second grid 110 of the 13th embodiment, as shown in FIG. 53A, each transmitting-section bridging portion 111 couples three X-ray transmitting sections 14b, or as shown in FIG. 53B, five X-ray transmitting sections 14b. The number of the X-ray transmitting sections 14b coupled by each transmitting-section bridging portion 111 is not limited to three or five. Two, four, or more than five X-ray transmitting sections 14b may be coupled by each transmitting-section bridging portion 111.

Figure 54:
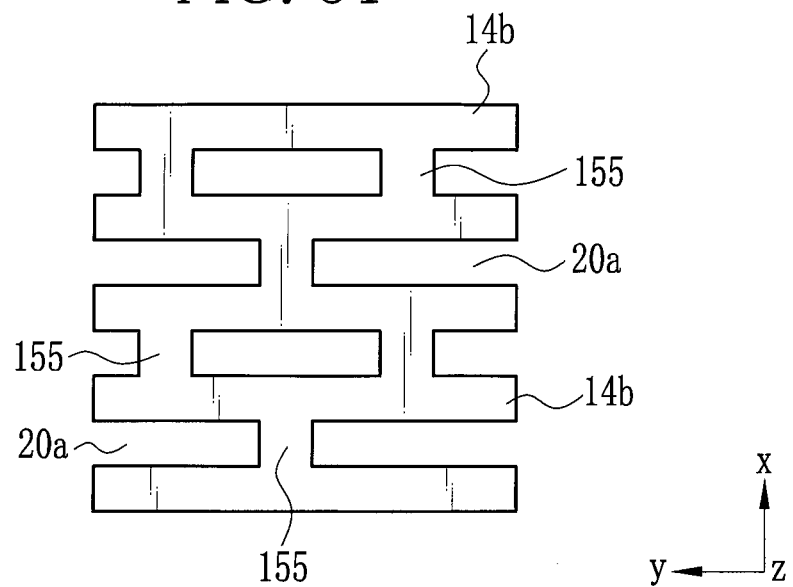
FIG. 54 is a plan view showing the etching substrate with transmitting-section bridge members in a staggered arrangement in the 18th embodiment.
Figure 55:
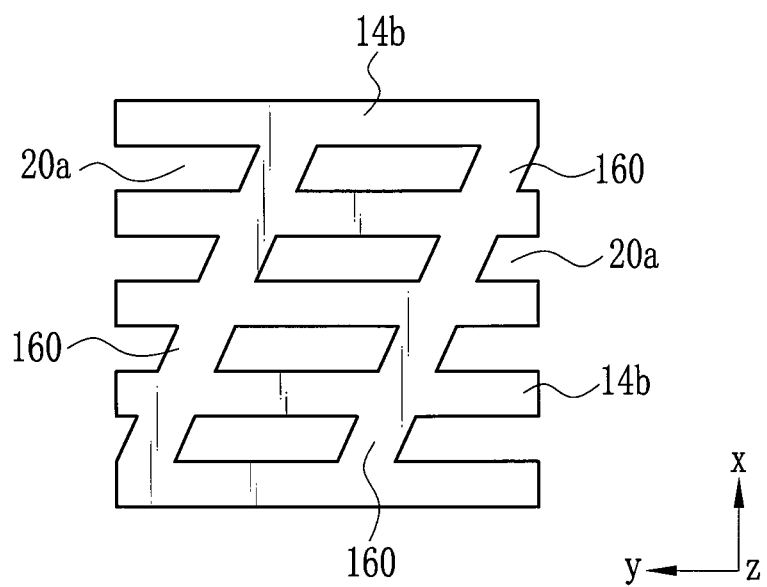
FIG. 55 a plan view showing the etching substrate of $18^{th}$ embodiment with the transmitting-section bridge members arranged in a slanting direction.

In the above embodiments, the transmitting-section bridging portions are aligned in parallel with the x direction, that is, the arranging direction of the X-ray transmitting sections 14b. As shown in FIG. 54, transmitting-section bridging portions 155 may be arranged in a staggered arrangement in the x direction. As shown in FIG. 55, transmitting-section bridging portions 160 may be arranged in a slanting direction relative to the x direction.

Figure 56:
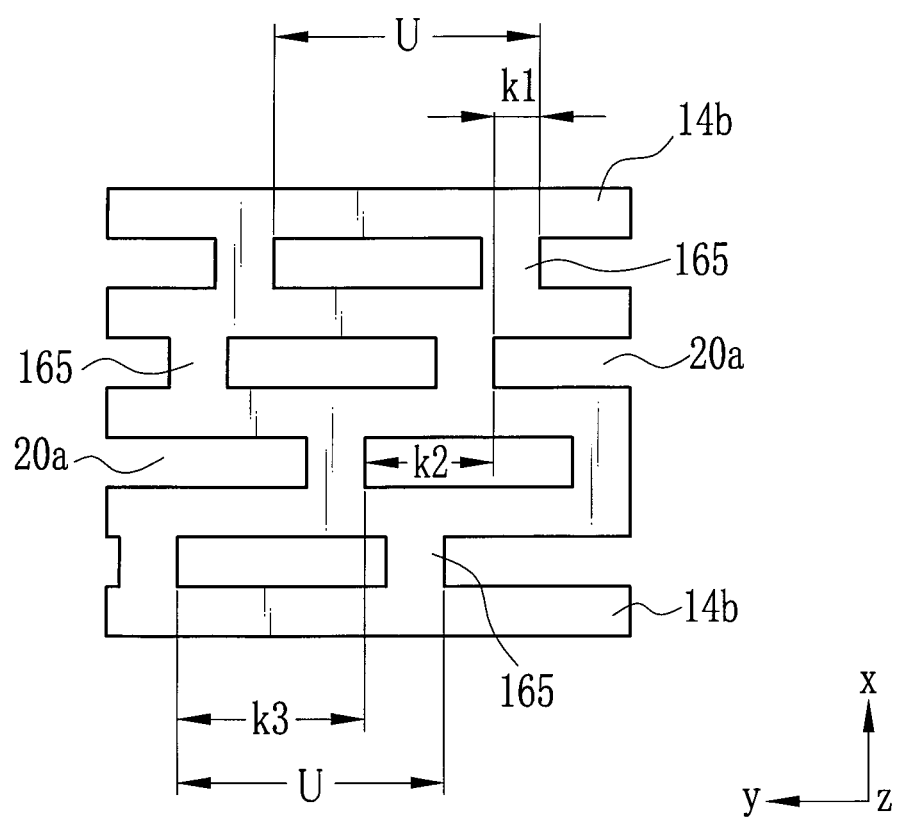
FIG. 56 is a plan view showing the etching substrate with the transmitting-section bridge members arranged randomly.

As shown in FIG. 56, transmitting-section bridging portions 165 may be arranged at a constant bridge pitch U in the y direction and at random intervals (k1 to k3) in the y direction between the transmitting-section bridging portions 165 adjacent in the x direction. To minimize the reduction in the performance of the second grid, it is preferable to arrange the transmitting-section bridging portions 165 randomly, because the areas with low X-ray shield properties are dispersed. Alternatively, the bridge pitch U may be set randomly.

As shown in FIG. 56, the bridge pitch U of the transmitting-section bridging portions 165 may be a value (a±b/2) distributed within a range "b" from a predetermined central value "a". For example, the bridge pitch U is in a range from 25 μm to 35 μm where the central value "a" is 30 μm, and a range b is 10 μm. The bridge pitch U may be a prime number which is not an integral multiple of an integer. In this case, for example, prime numbers equal to or larger than 25 μm and equal to or smaller than the pixel dimension (for example, 150 μm per side) in the x and y directions in the X-ray image detector may be used in order or at random. For example, 0, 1, and the prime numbers 3, 5, 7, 11, 13, 17, and 19 may be added to the reference bridge pitch U of 25 μm, and the added values 25, 26, 28, 30, 32, and so forth may be used in this order or at random.

19th Embodiment

In the above 13th to 18th embodiments, the transmitting-section bridging portions for coupling the X-ray transmitting sections 14b of the grid are described. One or more absorbing-section bridging portions may be provided in the grid.

Figure 58:
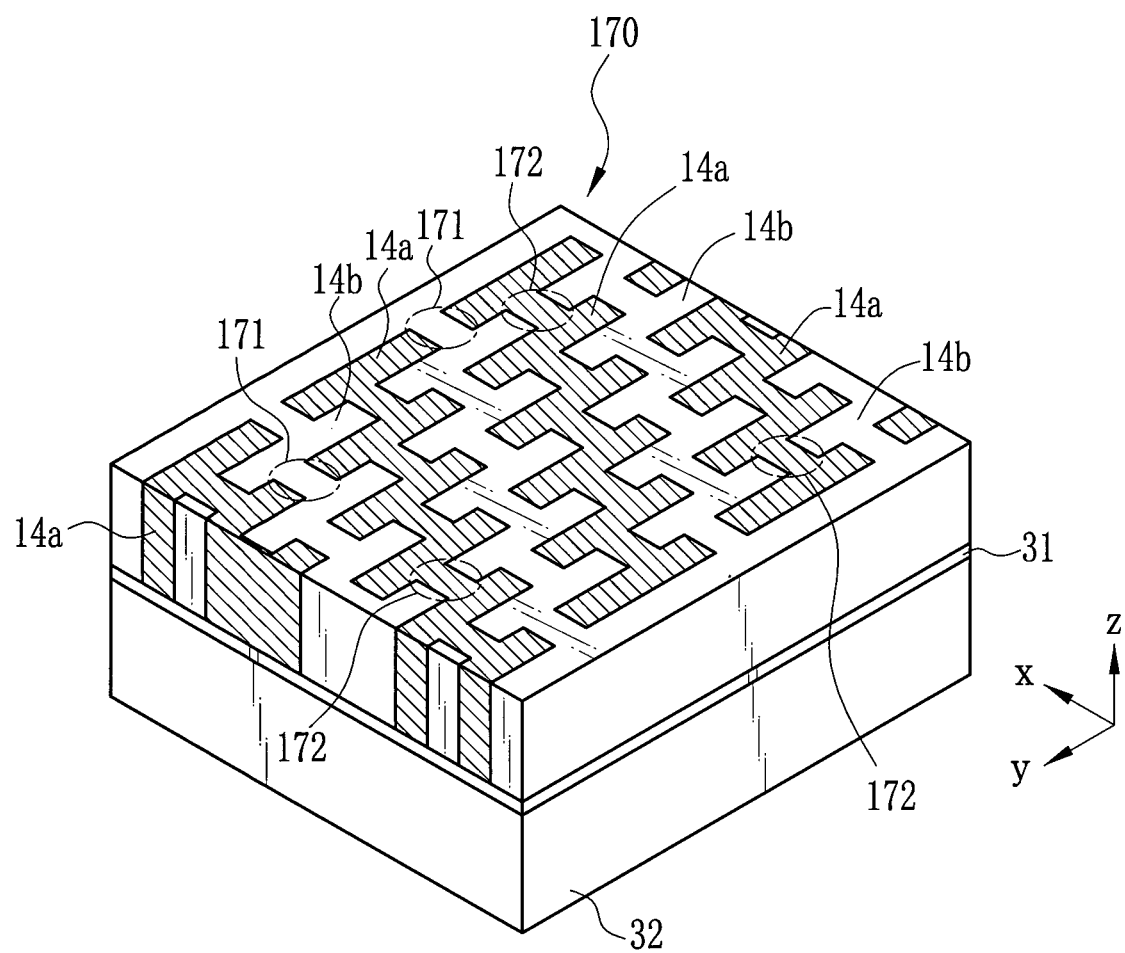
FIG. 58 is a perspective view showing a second grid of the $19^{th}$ embodiment.

FIG. 57A is a plan view of a second grid 170 of this embodiment, viewed from the X-ray image detector 15 side. FIG. 57B is a cross-section taken along a line A-A in FIG. 57A. FIG. 58 is a perspective view showing the second grid 170. The second grid 170 is provided with a plurality of transmitting-section bridging portions 171 for coupling the X-ray transmitting sections 14b and a plurality of absorbing-section bridging portions 172 for coupling the X-ray absorbing sections 14a. The transmitting-section bridging portions 171 and the X-ray transmitting sections 14b are made of the same material and formed integrally to strengthen the second grid 170. As with the transmitting-section bridging portions 171, the absorbing-section bridging portions 172 and the X-ray absorbing sections 14a are formed integrally from the same material to strengthen the second grid 170. The transmitting-section bridging portions 171 have the same configuration as in the 13th embodiment, so detailed descriptions thereof are omitted.

A width E of the absorbing-section bridging portion 172 in the y direction is the same as or larger than the width W2 of the X-ray absorbing section 14a. The arrangement pith S of the absorbing-section bridging portions 172 in the y direction is, for example, equal to or smaller than the pixel dimension (for example, 150 μm) of the X-ray image detector 15, and more preferably, five or more times as wide as the width W2 of the X-ray absorbing section 14a. This minimizes the influence of the absorbing-section bride portions 172 on the phase contrast image. A percentage of an area of the absorbing-section bridging portions 172 occupied in a pixel of the X-ray image detector 15 is equal to or smaller than 20%. If the area of the absorbing-section transmitting portion becomes too large relative to the area of one pixel, the X-ray transmission properties decrease. The transmitting-section bridging portions 171 and the absorbing-section bridging portions 172 are arranged in a staggered arrangement, for example.

Next, a method for producing the second grid 170 is described. As with the second embodiment, the second grid 170 is produced by steps of bonding the etching substrate 20 and the support substrate 32, forming the etch mask, forming the grooves 20a and the X-ray transmitting sections 14b, and forming the X-ray absorbing section 14a by the electroplating. In performing these steps, a main difference from the second embodiment is the shape of the etch mask. The etch mask is provided with, as with the etch mask of the 13th embodiment, a pattern for defining the shape of the transmitting-section bridging portion 171 and a pattern for defining the shape of the absorbing-section bridging portion 172.

Figure 59:
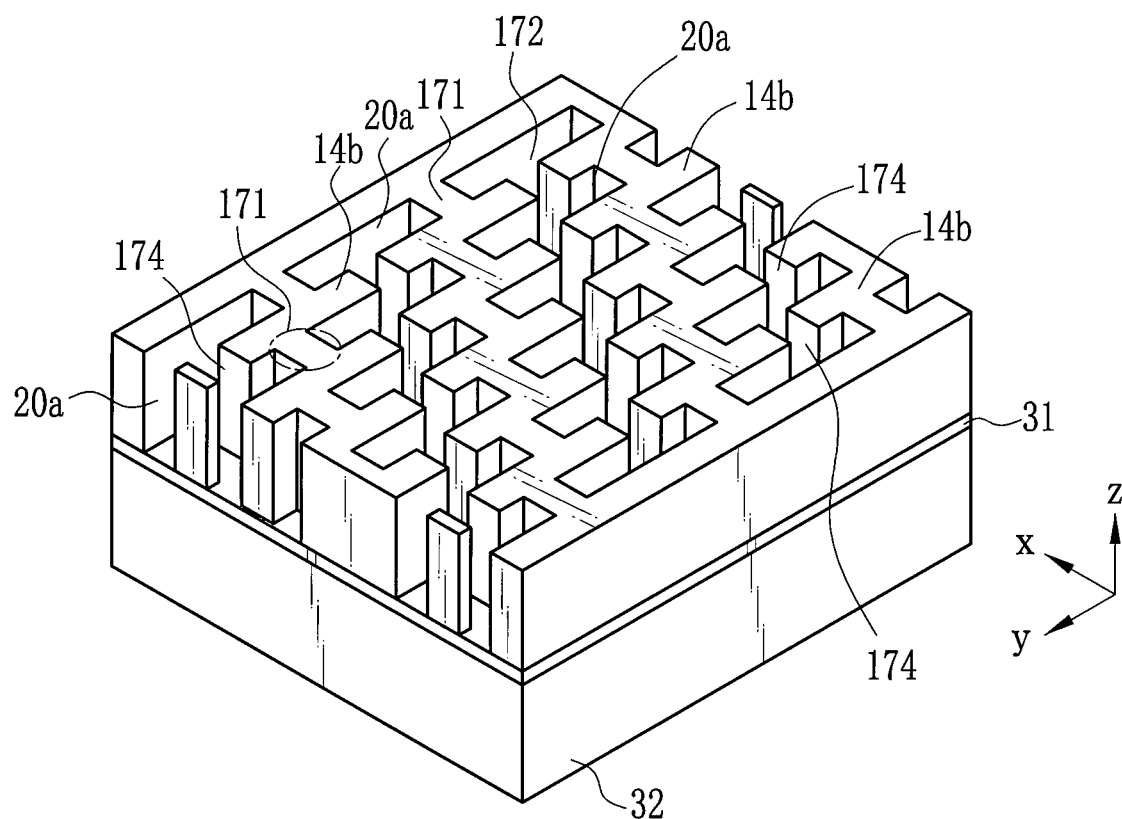
FIG. 59 is a perspective view showing the etching substrate of the $19^{th}$ embodiment after being etched.

FIG. 59 shows the etching substrate 20 after being etched. The etching substrate 20 is formed with the grooves 20a, the X-ray transmitting sections 14b, transmitting-section bridging portions 171, and coupling grooves 174 for forming the absorbing-section bridging portions 172. By filling the coupling groove 174 with the Au by the electroplating, the X-ray absorbing section 14a is formed. The coupling groove 174 couples the grooves 20a. Thereby, fluidity of the plating liquid in the grooves 20a improves, preventing uneven growth of the plating caused by retention of the plating liquid in the grooves 20a.

Figure 60A:
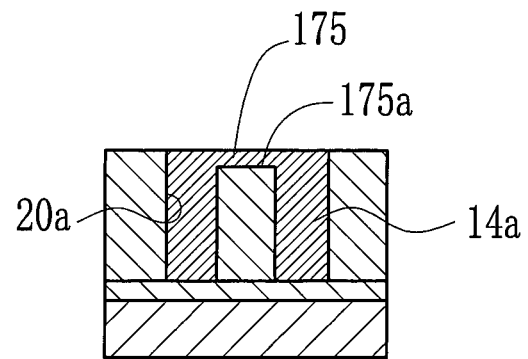
FIGS. 60A to 60D are cross-sectional views showing variations of absorbing-section bridge members in the $19^{th}$ embodiment.

In this embodiment, the absorbing-section bridging portion 172 has the same height as the X-ray absorbing section 14a. As shown in FIG. 60A, an absorbing-section bridging portion 175 for coupling only the upper portion of the X-ray absorbing sections 14a may be provided. To form the absorbing-section bridging portion 175, coupling grooves 175a for forming the absorbing-section bridging portions 175 are formed simultaneously with the formation of the grooves 20a, and then the coupling grooves 175a and the grooves 20a are filled with the Au simultaneously.

Figure 60B:
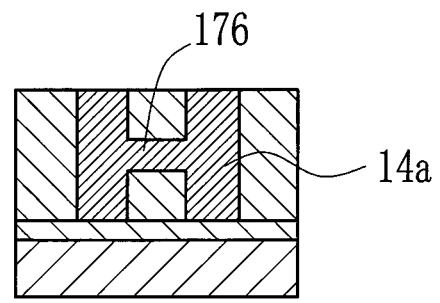

As shown in FIG. 60B, an absorbing-section bridging portion 176 may couple the middle portions of the X-ray absorbing sections 14a in the X-ray emission direction. The absorbing-section bridging portion 176 may be formed by combination of formation of grooves by etching, filling of the Au by the electroplating, and deposition of silicon by vapor deposition, and the like.

Figure 60C:
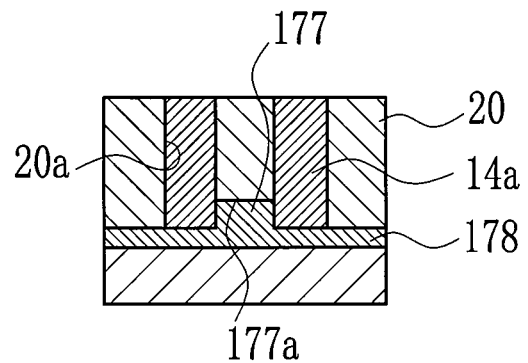

As shown in FIG. 60C, an absorbing-section bridging portion 177 may couple the bottom portions of the X-ray absorbing sections 14a. To form the absorbing-section bridging portion 177, a coupling groove 177a for forming the absorbing-section bridging portion 177 is formed in the bottom of the etching substrate 20 by etching, and then the Au is deposited on the bottom face of the etching substrate 20 by vapor deposition to form a seed layer 178. Thereafter, the groove 20a is formed in the etching substrate 20. The groove 20a is filled with the Au to form the X-ray absorbing section 14a. Thereby, the seed layer 178 and the X-ray absorbing section 14a are coupled together to form the absorbing-section bridging portion 177.

Figure 60D:
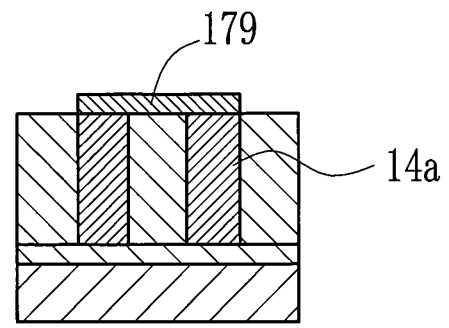

As shown in FIG. 60D, an absorbing-section bridging portion 179 may couple the upper portions, on the incident sides of the X-ray emission, of the X-ray absorbing sections 14b. To form the absorbing-section bridging portion 179, X-ray transmissive metal such as Ni, Cu, or Al is deposited by plating, vapor deposition, or the like, and then is etched in the shape of the absorbing-section bridging portion 179.

As described above, coupling the upper, middle, or bottom portions of the X-ray absorbing sections 14*a* by the absorbing-section bridging portion prevents the reduction in the X-ray absorption properties. This also reduces the amount of the Au used for the absorbing-section bridging portions. Thus cost of the grid is cut down.

Figure 61A:
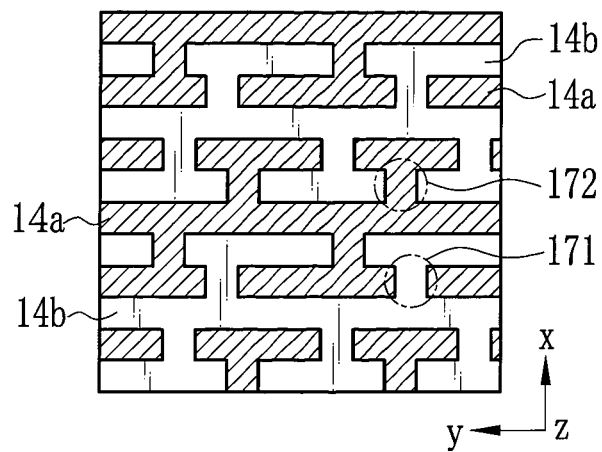
FIGS. 61A to 61C are plan views showing the transmitting-section bridge members each coupling several X-ray transmitting sections and the absorbing-section bridge members each coupling several X-ray absorbing sections in the $19^{th}$ embodiment.
Figure 61B:
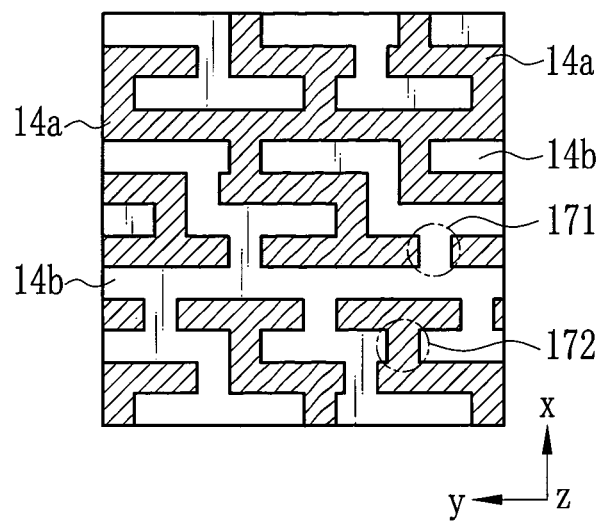

In this embodiment, the several X-ray absorbing sections 14*a* may be coupled by each of the absorbing-section bridging portions, and the several X-ray transmitting sections 14*b* may be coupled by each of the transmitting-section bridging portions. For example, in the second grid 170 shown in FIGS. 57A, 57B, and 58, the three X-ray absorbing sections 14*a* may be coupled as a group by the absorbing-section bridging portions 172, and the three X-ray transmitting sections 14*b* may be coupled as a group by the transmitting-section bridging portions 171 as shown in FIG. 61A. As shown in FIG. 61B, the five X-ray absorbing sections 14*a* may be coupled as a group by the absorbing-section bridging portions 172, and the five X-ray transmitting sections 14*b* may be coupled as a group by the transmitting-section bridging portions 171.

Figure 61C:
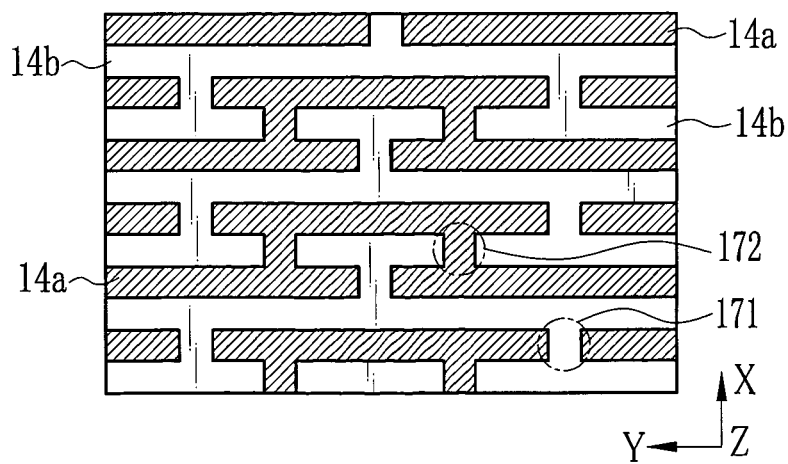

As shown in FIG. 61C, all the X-ray transmitting sections 14*b* may be coupled by the transmitting-section bridging portions 171, and every two X-ray absorbing sections 14*a* may be coupled by the absorbing-section bridging portions 172. Thereby, the reduction in the X-ray transmission properties due to the absorbing-section bridging portions 172 is prevented while the strength of the X-ray transmitting sections 14*b* is maintained. Two, four, or more than five X-ray absorbing sections 14*a* may be coupled by the absorbing-section bridging portions 172. Two, four, or more than five X-ray transmitting sections 14*b* may be coupled by the transmitting-section bridging portions 171.

Figure 62A:
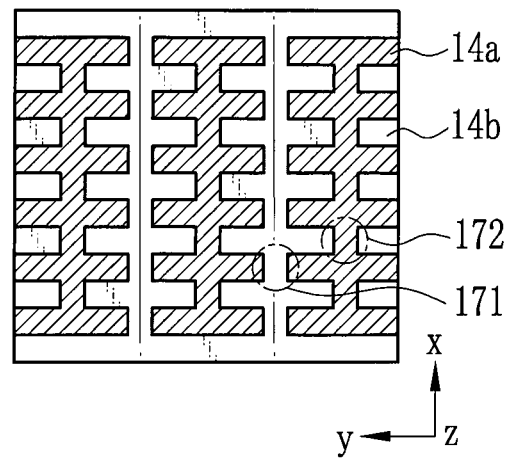
FIGS. 62A to 62C are plan views showing arrangement variations of the X-ray absorbing sections and the X-ray transmitting sections in the $19^{th}$ embodiment.
Figure 62B:
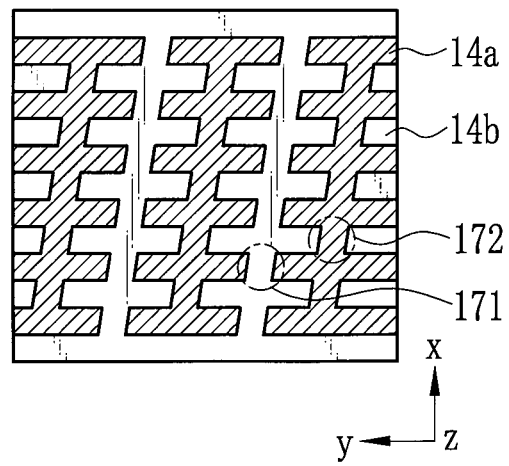
Figure 62C:
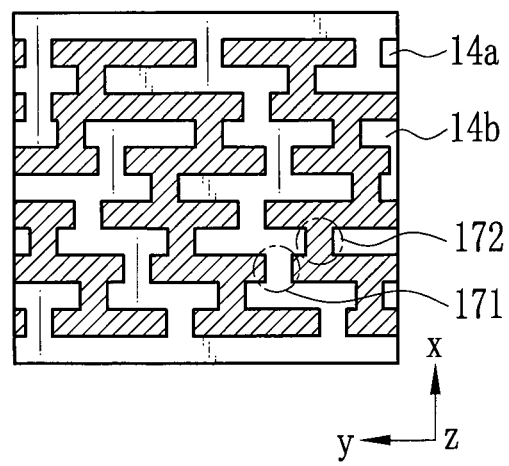

In the above embodiments, the transmitting-section bridging portions 171 and the absorbing-section bridging portions 172 are arranged in a staggered arrangement. As shown in FIG. 62A, the transmitting-section bridging portions 171 and the absorbing-section bridging portions 172 may be aligned in parallel with the x direction. As shown in FIG. 62B, the transmitting-section bridging portions 171 and the absorbing-section bridging portions 172 may be arranged in a slanting direction relative to the x direction. As shown in FIG. 62C, the transmitting-section bridging portions 171 and absorbing-section bridging portions 172 may be randomly arranged in the x direction with a random pitch in the y direction.

As with the transmitting-section bridging portion 165 of the 18$^{th}$ embodiment shown in FIG. 56, the transmitting-section bridging portions 171 may be arranged at random intervals in the y direction between the transmitting-section bridging portions 171 adjacent in the x direction while the pitch in the y direction is kept constant. The absorbing-section bridging portions 172 may be arranged at random intervals in the y direction between the absorbing-section bridging portions 172 adjacent in the x direction while the pitch in the y direction is kept constant. Each of the pitches of the transmitting-section bridging portions 171 and the absorbing-section bridging portions 172 may be a value (a±b/2) distributed within a range "b" from a predetermined central value "a". Each of the pitches may be a prime number which is not an integral multiple of an integer. In consideration of the reduction in the X-ray transmission properties of the transmitting-section bridging portions 171 and the X-ray absorption properties of the absorbing-section bridging portions 172, it is preferable to arrange the transmitting-section bridging portions 171 and the absorbing-section bridging portions 172 randomly.

20$^{th}$ Embodiment

In the above embodiments, the grid provided with the transmitting-section bridging portions and the grid provided with both the transmitting-section bridging portions and the absorbing-section bridging portions are described. Like a second grid 180 shown in FIGS. 63A and 63B, only absorbing-section bridging portions 181 may be provided to the X-ray absorbing sections 14*a*. This prevents the X-ray absorbing section 14*a* from being separated by the transmitting-section bridging portion. Thereby, the strength of the second grid 180 is further increased. A producing method, a width E, an arrangement pitch S, a configuration, and the like of the absorbing-section bridging portions 181 are similar to or the same as the absorbing-section bridging portions 172 of the 19th embodiment so the detailed descriptions are omitted.

21$^{st}$ Embodiment

The grid has a high aspect ratio, and is difficult to produce. Accordingly, it is preferable to examine the processing state at each step of the production. For example, in the etching step, in which the etching substrate is etched to form a plurality of the grooves, it is necessary to evaluate whether the etching reaches a predetermined depth and whether the width of the groove is uniform in the depth direction. In the electroplating step, in which the groove is filled with the Au, that is, the radiation absorbing material, it is necessary to evaluate whether the groove is filled with the Au uniformly (whether no void is formed).

For the examination in the etching step, a microscope observation method using visible reflecting light may be used. It is difficult, however, to observe the bottom of the groove with the width of several μm and the depth of 100 μm because light scattered by the surface of the groove interferes with the observation. For the examination in the electroplating step, X-ray transmission observation is applicable. This X-ray transmission observation uses a radiation source with a focal spot size of sub-μm order. The X-ray transmission observation, however, has a narrow observation field and needs a long time to take an image, resulting in a low throughput.

To solve the above problem, in this embodiment, after the etching step, first examination light that passes through the conductive substrate is emitted to examine the etching state. After the electroplating step, second examination light that passes through the conductive substrate and the etching substrate is emitted to examine the filling state of the Au in the groove. Hereinafter, the examination method is described.

Figure 64A:
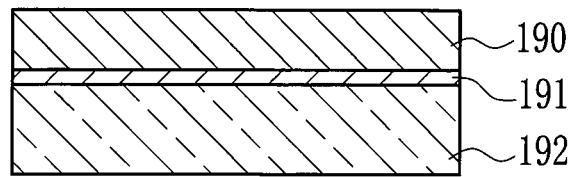
FIGS. 64A, 64B, and 64C are cross-sectional views showing an etching step and a method for examining an electroplating step in a $21^{st}$ embodiment.

As shown in FIG. 64A, for the production of the grid of this embodiment, as with the above-described second embodiment, an etching substrate 190, a conductive thin-layer 191, and a support substrate 192 are used, and the Au is used as the radiation absorbing material. To make the first examination light pass through the conductive substrate 191 and the support substrate 192, and to make the second examination light pass through the etching substrate 190, the conductive substrate 191, and the support substrate 192, an absorption wavelength λe of the etching substrate 190, an absorption wavelength λd of the conductive thin-layer 191, an absorption wavelength λs of the support substrate 192, a wavelength λm1 of the first examination light, and a wavelength λm2 of the second examination light are set so as to satisfy the following mathematical expressions (1) and (2) If the Au is sufficiently thick in the visible and infrared regions, the Au does not allow the first and second examination light to pass through (the first and second examination light is reflected by the Au).

$$\lambda d, \lambda s < \lambda m1 < \lambda e \quad (1)$$

$$\lambda d, \lambda s, \lambda e < \lambda m2 \quad (2)$$

To satisfy the conditions of the above mathematical expression (1), for example, the support substrate 192 is made of glass, and the conductive thin-layer 191 is made of a transparent conductive layer or film such as ITO, and the etching substrate 190 is made of silicon. For the first examination light, visible light with wavelengths from 0.4 μm to 0.7 μm, that is, the wavelengths longer than absorption wavelengths of the glass and the transparent conductive layer but shorter than absorption wavelengths of the silicon and the Au is used. Thereby, the first examination light passes through the conductive thin-layer 191 and the support substrate 192, but is reflected by the etching substrate 190 and the Au.

To satisfy the above mathematical expression (2), for the second examination light, infrared light with the wavelengths of equal to or longer than 0.7 μm, that is, the wavelengths longer than the absorption wavelengths of the glass, the transparent conductive layer, and the silicon, but shorter than the absorption wavelengths of the Au is used. Thereby, the second examination light passes through the etching substrate 190, the conductive thin-layer 191, and the support substrate 192, but is reflected by the Au.

Figure 64B:
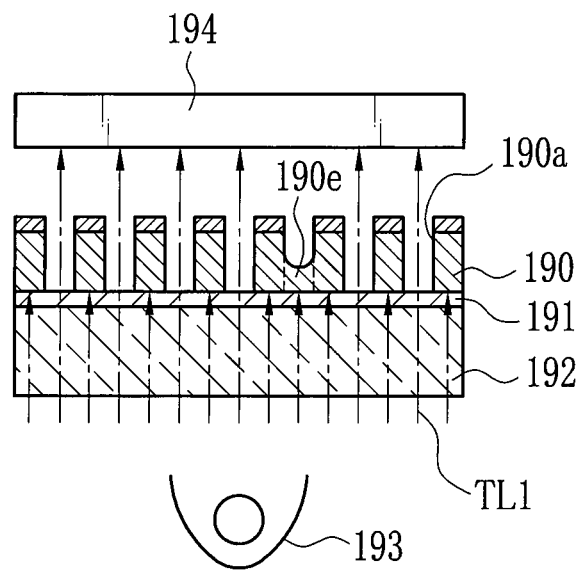

As shown in FIG. 64B, after the etching step, a first light source 193 emits first examination light TL1 from the support substrate 192 side. The etching step is the same or similar to that in the second embodiment, so detailed descriptions thereof are omitted. The first examination light TL1 passes through the support substrate 192 and the conductive thin-layer 191 and then absorbed by the etching substrate 190. The first examination light TL1 that passed through grooves 190a is detected by an image sensor 194 disposed above.

An image detected by the image sensor 194 shows the first examination light TL1 passed through the grooves 190a in a stripe pattern. When a silicon residue 190e remains in the groove 190a due to failure in the etching step, the silicon residue 190e is imaged as a shadow. Thus, by analyzing the image detected by the image sensor 194, a position and the size of the failure can be identified in addition to the presence or absence of the etching failure. For example, pass/failure judgment can be performed based on a pixel size (for example, 150 μm per side) in the x and y directions of the X-ray image detector 15. According to this embodiment, unlike the conventional microscope observation method, the observation is not interfered with the scattered light, and thus the microstructure of the etching substrate 190 with the high aspect ratio is examined appropriately.

Figure 64C:
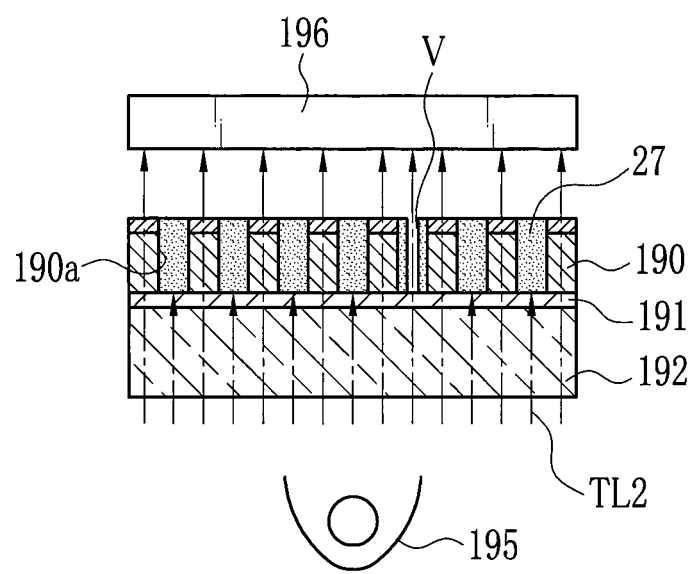

As shown in FIG. 64C, after the electroplating step, a second light source 195 emits second examination light TL2 from the support substrate 192 side. The electroplating step is the same or similar to that in the second embodiment, so detailed descriptions thereof are omitted. The second examination light TL2 passes through the support substrate 192, the conductive thin-layer 191, and then is absorbed by the Au 27. The second examination light TL2 that passed through the etching substrate 190 is detected by an image sensor 196 disposed above.

An image detected by the image sensor 196 shows the second examination light TL2 that passed through the etching substrate 190 in a stripe pattern. When a void V is formed in the groove 190a due to failure in the electroplating step or the like, widths of the stripes vary or the stripes are deformed or disappear. Thus, by analyzing the image detected by the image sensor 196, a position and the size of the failure can be identified in addition to the presence or absence of the electroplating failure. For example, pass/failure judgment can be performed based on a pixel size (for example, 150 μm per side) in the x and y directions of the X-ray image detector 15. This embodiment, unlike the conventional X-ray transmission observation, does not require expensive facilities such as the radiation source with a micro focal spot size, or the like. Thus, this embodiment is applicable at low cost. This embodiment provides a wide observation field, improving a throughput of the examination.

For the conductive thin-layer 191, a transparent conductive layer of ITO, IZO, ZnO or the like may be used, or a metal thin-layer of Au, Pd, Pt, Ni, Cr, Ti, or the like with the thickness equal to or smaller than 500 Å may be used. When used in the substrate bonding, the electroplating, or the like, the transparent conductive layer has intrinsic properties inferior to those of the metal, so the transparent conductive layer and the metal thin-layer may be used in combination.

To perform the substrate bonding or electroplating through the conductive thin-layer, it is necessary to consider the properties of the material. For example, in the diffusion bonding that is one of the methods used in the substrate bonding, the interdiffusion at the bonding surface is important. In the anodic bonding, activation energy is important. In electroplating, plating liquid resistance and adhesion with the plating material are important. Here, many of the transparent conductive layers are made of oxides. Such transparent conductive layers are inferior to the metal in the above properties. To compensate the above properties, it is preferable to provide a thin metal layer on the surface without impairing the transparency. The metal layer may be provided on the transparent conductive layer only on its bonding surface, or on both the bonding surface and the surface to be etched and plated when the etching is performed to the etching substrate. For example, when the thickness of the transparent electrode is 2000 Å, a thin Ni layer of approximately 250 Å is provided on both surfaces of the transparent electrode. Thereby, transparency, bonding, and plating performance are ensured. In the grid of this embodiment, sections or portions other than the Au 27 are transparent to visible light and infrared light even after the completion of the grid. Accordingly, the grid can be used for examination or inspection after the completion.

22nd Embodiment

A size of imaging field of view of the above-described X-ray imaging system is under constraint of a distance between the X-ray source and the first grid and a distance between the X-ray source and the second grid. The X-ray source is regarded as a point light source, so a spot size increases as the distance from the X-ray source increases. A wavefront, however, propagates radially maintaining equal distance from the light source, and therefore, forms a curved plane. In other words, an X-ray incident angle from the X-ray source at the center of the grid differs from that at the edge portion of the grid. When a flat grid (the same incident angles at the center and the edge portions) is used, the X-ray incident angle and the grid angle are not parallel at the edge portion of the grid due to the difference in the X-ray incident angles. This causes vignetting. As a result, an opaque area appears and thus limits the effective area. To increase the size of the imaging field of view of the X-ray imaging system, the sizes of the two grids should be enlarged. Using the large grids, however, is difficult because it requires to deal with vignetting at their edge portions and to control the convergence in the thickness direction of the grids. To pass the X-ray emitted from the X-ray source that is the point light source, the first and second grids should be bent into a convergence type. It is difficult, however, to bend the conventional grids because they are made of hard inorganic materials.

Figure 65:
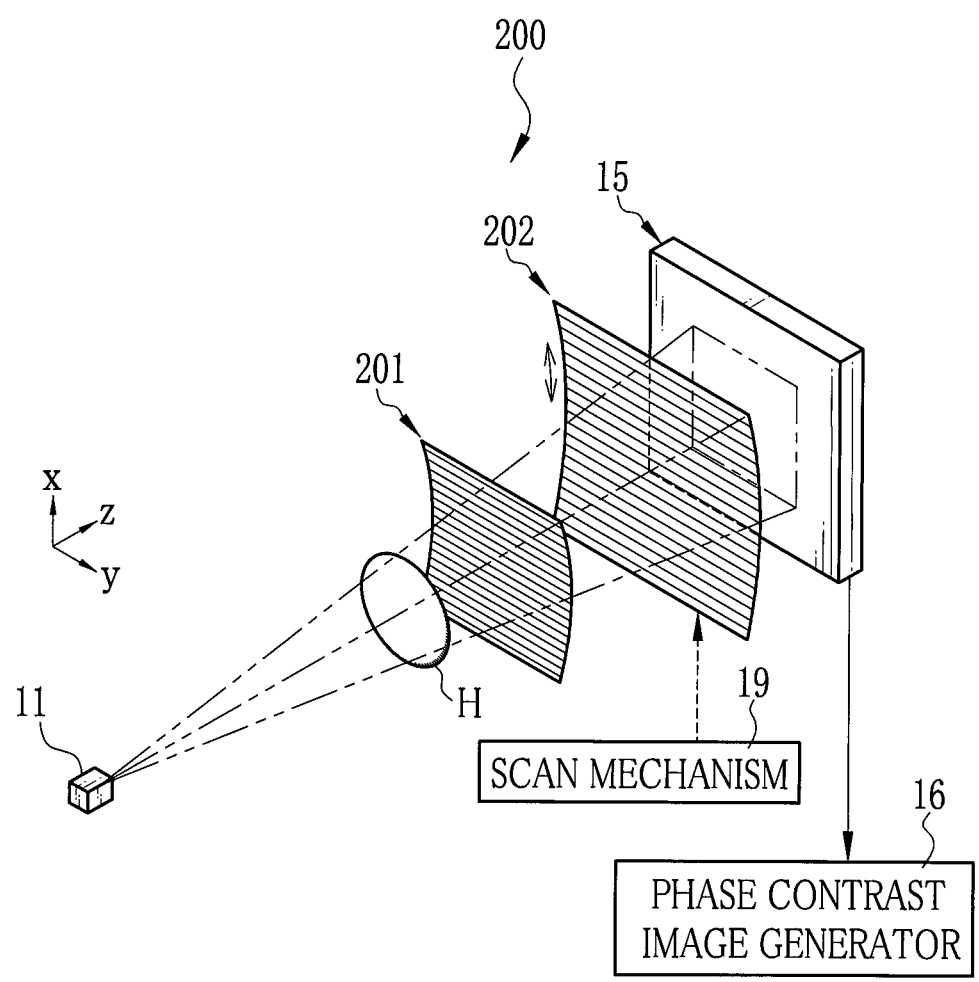
FIG. 65 is a schematic diagram of an X-ray imaging system employing concave grids in $22^{nd}$ to $24^{th}$ embodiments.

To solve the above problem, a flexible grid 202 may be used. Like an X-ray imaging system 200 shown in FIG. 65, a first grid 201 and a second grid 202 may be bent along a cylindrical shape with a center in the y direction. For example, when the grids of the first embodiment are used for the first and second grids 201 and 202, it is preferable that the thickness L1 of the etching substrate 20 is 20 µm to 150 µm, and the thickness L2 of the conductive substrate 18 is 50 µm to 150 µm, and the thickness of the second grid 14 after bonding the etching substrate 20 and the conductive substrate 18 is less than 200 µm.

Figure 66:
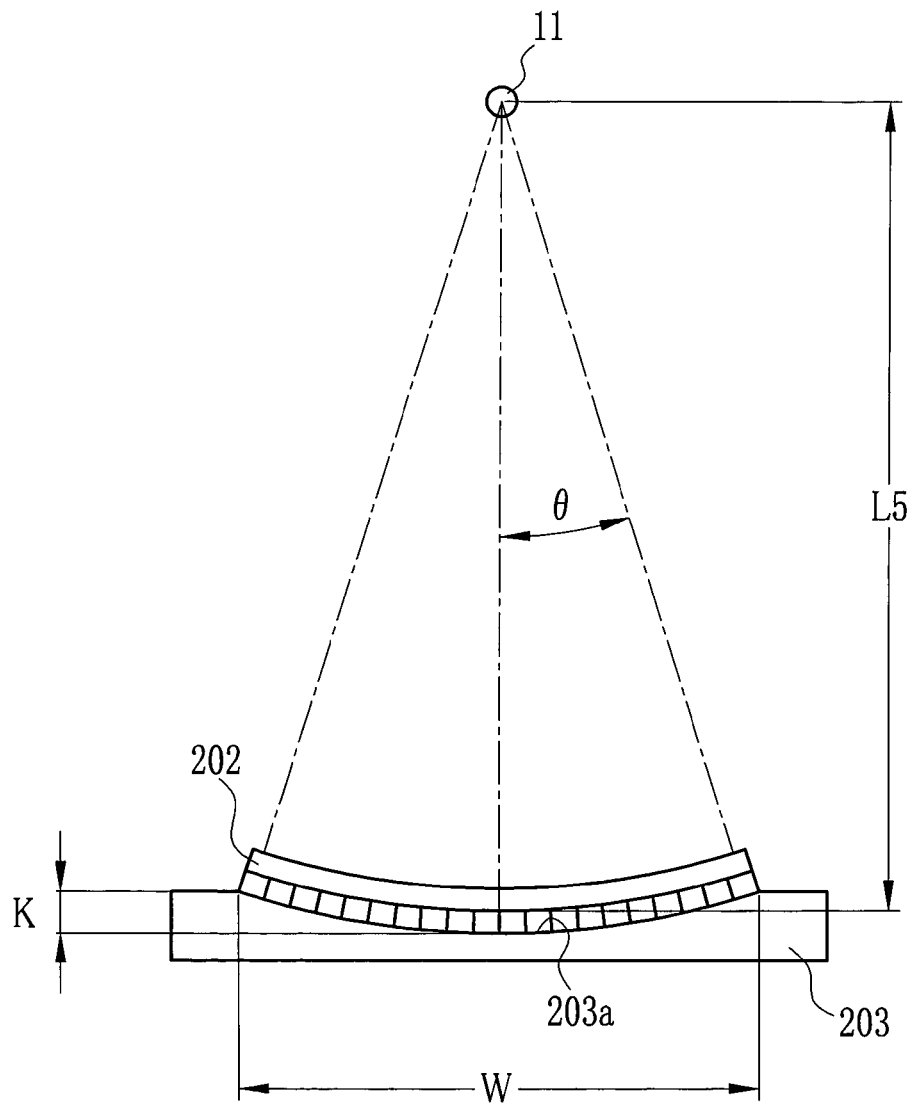
FIG. 66 is a cross-sectional view showing a curved structure of a second grid in the $22^{nd}$ to $24^{th}$ embodiments.

Hereinafter, a flexible structure of the grid is described using the second grid 202 as an example. It is necessary to bend the second grid 202 along a radiation angle of the X-ray to pass the cone-beam X-ray emitted from the X-ray source 11 that is a point light source. As shown in FIG. 66, for example, the radiation angle θ is approximately 2° where a distance L5 between the X-ray source 11 and the second grid 202 is from 200 cm to 230 cm, a length W of one of the sides of the rectangular second grid 202 is 15 cm. To pass the X-ray at the outer edge portion of the second grid 202, an amount of curvature K of the edge portion relative to the center of the second grid 202 is approximately 3 mm.

In this embodiment, to bend the second grid 202 appropriately, a curved concave portion 203a is formed on one of the faces of a plate like holding member 203 for convergence. The curved concave portion 203a has a cylindrical surface so as to bend the edge portions of the second grid 202 by approximately 3 mm. The second grid 202 is bent and placed on the curved concave portion 203a from the etching substrate 20 side. A position of the second grid 202 relative to the curved concave portion 203a may be aligned as necessary and the aligned position is fixed by adhesion or the like. Thereby, a bent grid that allows the cone-beam X-rays to pass through is formed with high accuracy. The second grid 202 may be bent in a circular shape instead of the cylindrical shape. The first grid 201 can be bent in the same manner as the second grid 202, so detailed descriptions thereof are omitted.

23$^{rd}$ Embodiment

To use the grid of the second embodiment as the second grid 202 to make it flexible, it is preferable that the support substrate 32 is made of a flexible organic material with low absorption properties. For the material of the support substrate 32 satisfying the above conditions, for example, polymer materials such as acryl, novolak resin, polyimide, polyethylene, or parylene. Unlike the conductive substrate 18 of the first embodiment, the support substrate 32 does not require conductivity. Accordingly, a highly X-ray transmissive and highly flexible material can be selected. Thus, a flexible grid with high X-ray transmission properties is obtained. The thickness of the conductive thin-layer 31 should be set so as not to reduce the flexibility of the support substrate 32.

To bond the support substrate 32 and the etching substrate 20, the bonding with the application of heat and pressure or the bonding using an adhesive may be used, or a solution dispersed in a solvent may be applied by spin coating or the like and then thermosetted. For example, when permanent photoresist SU-8 is used, a layer can be formed by the spin coating at the number of revolutions of 100 rpm and then by application of heat treatment at the order of 200° C. The thickness of the formed layer is from 10 µm to 200 µm. The second grid of this embodiment may be bent in the same manner as in the 22nd embodiment.

24$^{th}$ Embodiment

In the 23$^{rd}$ embodiment, a flexible organic material is used as the material of the support substrate 32. Alternatively, an inorganic material may be used. In this case, the inorganic material is made flexible by limiting its thickness. The inorganic material used for the support substrate 32 is preferably a material with low X-ray absorption properties, for example, borosilicate glass, soda-lime glass, quartz, alumina, GaAs, Ge, or the like. Further, silicon, also used as the material of the etching substrate 20, is preferable. Examples of the borosilicate glass include Pyrex (registered trademark) glass and TEMPAX (registered trademark) glass. The material of the conductive thin-layer 31 and the position of the conductive thin-layer 31 are the same or similar to those in the 23rd embodiment, so detailed descriptions thereof are omitted. The total thickness of the etching substrate 20 and the support substrate 32 after being bonded is preferably less than 200 µm in consideration of flexibility.

25$^{th}$ Embodiment

Figure 67:
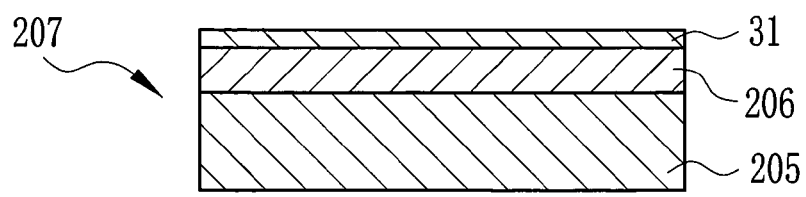
FIG. 67 is a cross-sectional view showing a support substrate in a $25^{th}$ embodiment.

In the above 23$^{rd}$ embodiment, the support substrate 32 made of the organic material may be deflected during the etching or the electroplating to deform the groove 20a. Thereby, the performance of the X-ray absorbing sections 14a may be degraded. To prevent this problem, as shown in FIG. 67, a support substrate 207 may be composed of a reinforcing substrate 205 having rigidity and an organic material layer 206 provided on the reinforcing substrate 205. The rigidity of the reinforcing substrate 205 prevents the deformation of the etching substrate 20 during the etching. The reinforcing substrate 205 may be removed by applying the above-described third embodiment after the electroplating of the Au in the grooves 20a. The reinforcing substrate 205 may be thinned to make the grid flexible enough to be bent. The grid using the support substrate 207 is produced by the steps the same or similar to those in the second embodiment, so detailed description thereof are omitted.

For the reinforcing substrate 205, it is preferable to use a material with rigidity which does not allow deformation during the etching or electroplating, for example, silicon, borosilicate glass, soda-lime glass, quartz, alumina, GaAs, Ge, or the like. For the organic material layer 206, it is preferable to use a polymer material, for example, acryl, novolak resin, polyimide, parylene, or the like. It is preferable that the thickness of the organic material layer 206 be, for example, of the order of 5 µm.

26$^{th}$ Embodiment

Figure 68:
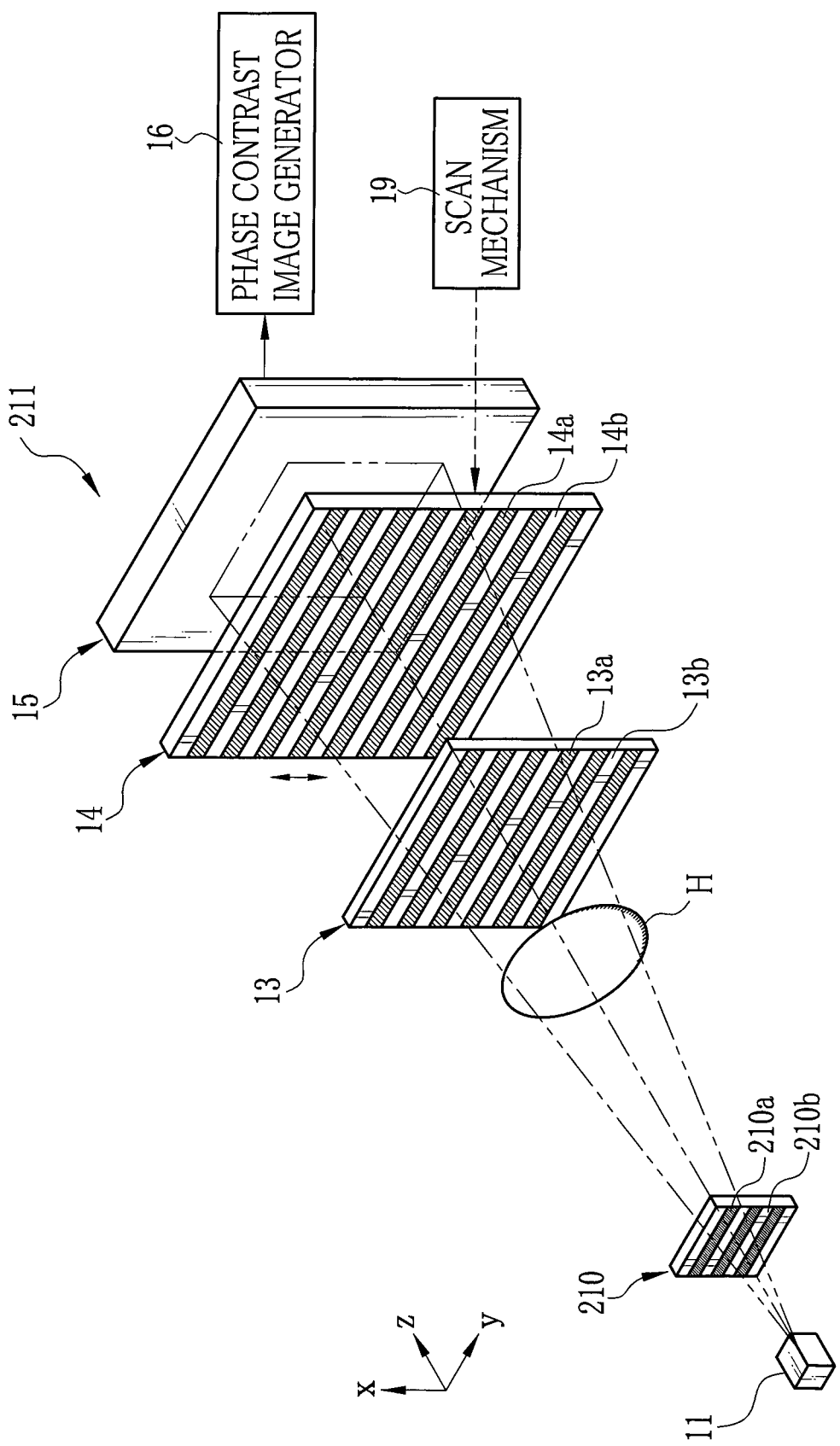
FIG. 68 is a schematic diagram showing an X-ray imaging system employing an X-ray source grating in a $26^{th}$ embodiment.

In the above embodiments, the X-ray imaging system using the first and second grids is described as an example. As shown in FIG. 68, the present invention is applicable to an X-ray imaging system 211 in which an X-ray source grid 210 is disposed downstream of the X-ray source 11 in the X-ray emission direction. Like the first and second grids 13 and 14, the X-ray source grid 210 is an absorbing-type grid provided with X-ray absorbing sections 210a and X-ray transmitting sections 210b. The X-ray source grid 210 partly shields the X-ray emitted from the X-ray source 11 to reduce an effective focal spot size and to form a set of a plurality of linear light sources (scattered light source) with small widths. The structure and the producing method of the X-ray source grid 210 may be those of the above embodiments described above.

27th Embodiment

Figure 69B:
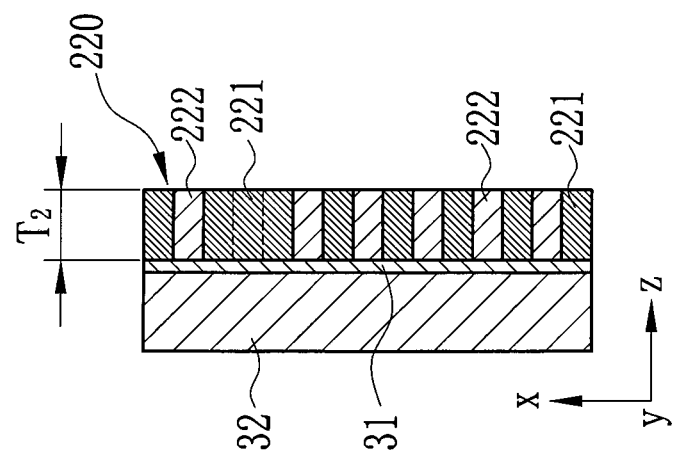
FIG. 69B is a cross-sectional view taken along a line A-A in FIG. 69A.
Figure 69A:
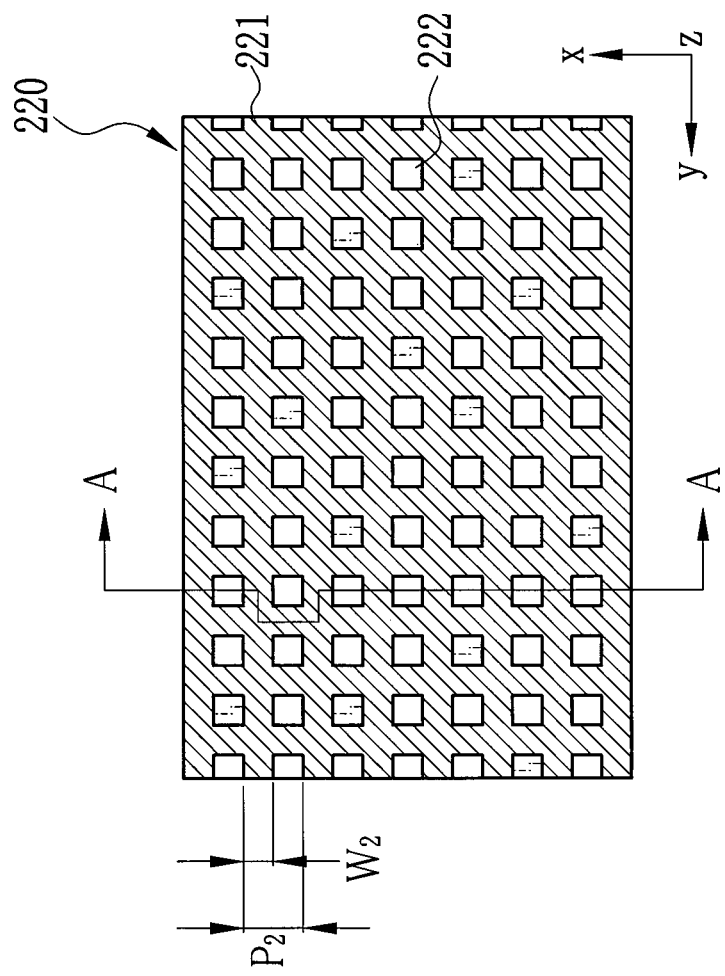
FIG. 69A is a plan view of a second grid with X-ray absorbing sections arranged in a cross-like pattern in a $27^{th}$ embodiment.

In the above embodiments, the grid with the stripe pattern in which the X-ray absorbing sections and the X-ray transmitting sections are alternately arranged is described as an example. The embodiments other than those related to the bridging portions are applicable to a grid having cross-like shaped X-ray absorbing sections. As shown in FIGS. 69A and 69B, a second grid 220 of this embodiment is composed of X-ray absorbing sections 221 disposed in cross-like shape to intersect with one another in the x and y directions and X-ray transmitting sections 222 surrounded by the X-ray absorbing sections 221. The width W2, the pitch P2, the thickness T2, and the like of the X-ray absorbing sections 221 are the same or similar to those in the above embodiments, so detailed descriptions are omitted.

To produce the second grid 220 of this embodiment, for example, as with the above-described the second embodiment, the etch mask is formed on the etching substrate. The grooves and the X-ray transmitting sections 222 are formed on the etching substrate through the etch mask. To form the grooves, an etch mask with cross-like shaped mask patterns is used so as to form cross-like shaped grooves. Then, as with the second embodiment, the grooves are filled with the Au by electroplating using the conductive thin-layer 31 as the seed layer.

According to the second grid 220 of this embodiment, the strength of the grid is improved without providing the bridging portions. During the production of the second grid 220, the grooves for forming the X-ray absorbing sections 221 are also used as flow channels of the plating liquid. The grooves prevent the plating liquid from retention. As a result, formation of the voids or the like is prevented. The X-ray absorbing sections 221 are arranged to intersect one another in the x and y directions. Alternatively, the X-ray absorbing sections 221 may be arranged in a slanting direction in the xy plane. The X-ray absorbing sections 221 are arranged in the cross-like shape. Alternatively, the X-ray transmitting sections may be arranged in the cross-like shape, and the X-ray absorbing section may be surrounded by the X-ray transmitting sections.

In the above embodiments, the configuration and the producing method of the grid are described using the second grid 14 as an example. The above embodiments may also be used for the first grid or the X-ray source grid. The first and second grids are configured to linearly project the X-ray passed through their X-ray transmitting sections. The present invention is not limited to the above configuration. A configuration (disclosed in PCT International Publication No. WO 2004/058070) in which the X-ray transmitting sections diffract the X-ray to generate so-called Talbot effect may be used. In this case, however, a distance between the first and second grids needs to be set at a Talbot length. In addition, instead of the absorbing-type grid, a phase-type grid may be used. The phase-type grid used instead of the first grid projects a fringe image (self image) generated by the Talbot effect to the second grid.

In the above embodiments, the fringe image whose intensity is changed by the second grid is detected using the fringe scanning method to generate the phase contrast image. An X-ray imaging system for generating a phase contrast image per image capture is known. For example, in an X-ray imaging system disclosed in PCT International Patent Publication No. WO 2010/050483 corresponding to U.S. Patent Application Publication No. 2010/0290590, an X-ray detector detects a moiré generated by the first and second grids. Intensity distribution of the detected moiré is transformed by Fourier-transform. Thereby, spatial frequency spectrum is obtained. A spectrum corresponding to a carrier frequency is separated from the spatial frequency spectrum to perform inverse Fourier-transform. Thus, a differential phase image is obtained. The grid of the present invention may be used for at least one of the first and second grids of such X-ray imaging system.

There is an X-ray imaging system for generating a phase contrast image per image-capture which uses a direct conversion type X-ray image detector composed of a conversion layer and charge collection electrodes as the intensity modulator instead of the second grid. In the X-ray imaging system, for example, the charge collection electrode in each pixel is composed of linear electrode groups arranged to have mutually different phases. Each linear electrode group is composed of linear electrodes arranged at the period substantially coinciding with the periodic pattern of the fringe image formed using the first grid and electrically connected to each other. Each linear electrode group is controlled individually, and thereby the charge is collected. Thereby, two or more fringe images are obtained per image capture. The phase contrast image is generated based on the obtained fringe images (see configuration disclosed in Japanese Patent Laid-Open Publication No. 2009-133823 corresponding to U.S. Pat. No. 7,746,981). The grid of the present invention may be used as the first grid of this X-ray imaging system.

In another X-ray imaging system for generating a phase contrast image per image-capture, first and second grids may be disposed such that extending directions of the X-ray absorbing sections and X-ray transmitting sections are relatively inclined at a predetermined angle. A moiré period in the extending directions caused by the inclination is divided and the images are captured. Thereby, two or more fringe images at the different relative positions of the first and second grids are obtained. A phase contrast image may be generated using such fringe images. The grid of the present invention may be used as at least one of the first and second grids in the X-ray imaging system.

An X-ray imaging system which uses an X-ray image detector of an optical reading type to omit the second grid may be used. In this system, a first electrode layer, an optical conductive layer, a charge accumulation layer, and a second electrode layer are layered in this order. The first electrode layer passes a periodic pattern image formed by the first grid. The optical conductive layer captures emission of the periodic image passed through the first grid to generate charge. The charge accumulation layer accumulates the charge generated by the optical conductive layer. The second electrode layer is provided with a plurality of linear electrodes which pass the reading light. The X-ray image detector of the optical reading type is used as the intensity modulator. The X-ray image detector of the optical reading type reads an image signal per pixel corresponding to each liner electrode by scanning of the reading light. By forming the charge accumulation layer in a grid shape in a pitch smaller than an arrangement pitch of the linear electrodes, the charge accumulation layer functions as the second grid. The grid of the present invention may be used as the first grid of such X-ray imaging system.

In the above embodiments, the object H is disposed between the X-ray source and the first grid. The phase contrast image is generated in the same manner when the object H is disposed between the first grid and the second grid. The above embodiments may be combined as long as the combination does not include contradiction.

INDUSTRIAL APPLICABILITY

The above described embodiments are applicable to radiation imaging systems used for medical diagnoses and other radiation imaging systems for industrial use, nondestructive inspections, and the like. The present invention is applicable to grids for removing scattered radiation in X-ray imaging. The present invention is capable of using gamma rays and the like as radiation in addition to the X-rays.

The invention claimed is:

1. A method for producing a grid for radiation imaging comprising:
    bonding a radiation-transmissive first substrate and an electrically conductive and radiation-transmissive second substrate;
    etching the first substrate through an etch mask to form grooves and a plurality of radiation transmitting sections disposed between the grooves; and
    plating the grooves by filling of a radiation absorbing material to form a plurality of radiation absorbing sections by an electroplating method using the second substrate as an electrode.

2. The method of claim 1, wherein deep dry etching is used for the etching.

3. The method of claim 1, wherein the second substrate has substantially the same thermal expansion coefficient as the first substrate.

4. The method of claim 1, wherein the second substrate comprises a conductive thin-layer used as the electrode and a support substrate provided with the conductive thin-layer.

5. The method of claim 1, wherein the second substrate comprises a semiconductor, a same material as the first substrate.

6. The method of claim 5, wherein the second substrate comprises the semiconductor used as the electrode and a support substrate comprising an insulator.

7. The method of claim 5, wherein the first substrate comprises a semiconductor of one conductivity type doped with an impurity, and the second substrate comprises a semiconductor of a conductivity type opposite to the one conductivity type, doped with another impurity.

8. The method of claim 7, wherein the semiconductor of one conductivity type comprises an n-type semiconductor.

9. The method of claim 1, wherein at least a surface of the first substrate includes an insulation property after the etching.

10. The method of claim 9, wherein the first substrate includes a specific resistance equal to or larger than 100 Ω·cm.

11. The method of claim 10, further including forming an insulating layer on a part or an entire of the surface of the first substrate after the etching.

12. The method of claim 11, wherein the insulating layer is hydrophilic.

13. The method of claim 9, wherein the specific resistance is increased by ion implantation to the first substrate after the etching step.

14. The method of claim 1, wherein the first substrate is removed by a predetermined thickness from at least one of faces of the first substrate after the plating.

15. The method of claim 14, wherein the second substrate is removed when the first substrate is removed by the predetermined thickness from the face to which the second substrate is bonded.

16. The method of claim 15, wherein the first substrate is removed by the predetermined thickness from the face to which the second substrate is bonded, after the first substrate is removed by the predetermined thickness from and a protective layer is formed on the face not bonded to the second substrate.

17. The method of claim 1, wherein etching is performed to the first substrate after the plating to remove the radiation transmitting sections between the radiation absorbing sections.

18. The method of claim 1, further including forming a plurality of depression portions on at least one of bonding surfaces of the first and second substrates before the bonding.

19. The method of claim 1, further including:
    making the bonding surface of the first substrate into a rough surface before the bonding;
    forming a radiation-transmissive and electrically conductive anchor layer on the rough surface; and
    polishing the anchor layer to improve smoothness of the anchor layer.

20. The method of claim 1, further including a bending the grid by bonding the grid to a curved surface provided in radiation-transmissive holding member.

* * * * *